(12) United States Patent
Shen et al.

(10) Patent No.: US 10,980,222 B2
(45) Date of Patent: Apr. 20, 2021

(54) GENETICALLY MODIFIED NON-HUMAN ANIMAL WITH HUMAN OR CHIMERIC CD27

(71) Applicant: Biocytogen Pharmaceuticals (Beijing) Co., Ltd., Beijing (CN)

(72) Inventors: Yuelei Shen, Beijing (CN); Yang Bai, Beijing (CN); Rui Huang, Beijing (CN); Chengzhang Shang, Beijing (CN); Yanan Guo, Beijing (CN); Meiling Zhang, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/435,198

(22) Filed: Jun. 7, 2019

(65) Prior Publication Data

US 2019/0343096 A1    Nov. 14, 2019

Related U.S. Application Data

(63) Continuation of application No. PCT/CN2017/117984, filed on Dec. 22, 2017.

(30) Foreign Application Priority Data

Dec. 23, 2016 (CN) .......................... 201611206266.7
Dec. 22, 2017 (CN) .......................... 201711402264.X

(51) Int. Cl.
| | | |
|---|---|---|
| *A01K 67/027* | (2006.01) | |
| *C07H 21/04* | (2006.01) | |
| *C07K 16/28* | (2006.01) | |
| *G01N 33/50* | (2006.01) | |

(52) U.S. Cl.
CPC ...... *A01K 67/0278* (2013.01); *C07K 16/2878* (2013.01); *G01N 33/5011* (2013.01); *A01K 2207/15* (2013.01); *A01K 2217/052* (2013.01); *A01K 2227/105* (2013.01); *A01K 2267/0331* (2013.01)

(58) Field of Classification Search
CPC ............ A01K 67/0278; A01K 2207/15; A01K 2217/15; A01K 2227/105; C07H 21/04
USPC ................... 800/18; 536/23.4, 23.5
See application file for complete search history.

(56) References Cited

U.S. PATENT DOCUMENTS

| | | |
|---|---|---|
| 4,683,195 A | 7/1987 | Mullis et al. |
| 2010/0173324 A1 | 7/2010 | Mori et al. |
| 2012/0093805 A1 | 4/2012 | Kubota |
| 2015/0106961 A1 | 4/2015 | Rojas et al. |

FOREIGN PATENT DOCUMENTS

| | | |
|---|---|---|
| CN | 104561095 | 4/2015 |
| WO | WO 2009100942 | 8/2009 |
| WO | WO 2011130434 | 10/2011 |
| WO | WO 2018001241 | 1/2018 |
| WO | WO 2018041118 | 3/2018 |
| WO | WO 2018041119 | 3/2018 |
| WO | WO 2018041120 | 3/2018 |
| WO | WO 2018041121 | 3/2018 |
| WO | WO 2018086583 | 5/2018 |
| WO | WO 2018086594 | 5/2018 |
| WO | WO 2018068756 | 4/2019 |

OTHER PUBLICATIONS

Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Yang et al., 2016, PNAS, 113(41), E6209-E6218, p. 1-10.*
Guo et al., 2015, Cell Research, vol. 25, p. 767-768.*
Lee et al., 2016, Drug Discovery Today: Disease Models, vol. 20, p. 13-20.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Keler et al., 2011, US 20110274685 A1.*
Furuya et al., 2010, GeneSeq Accession No. AXU72721, computer printout, p. 7-9 (For SEQ ID No. 18).*
Furuya et al., 2010, GeneSeq Accession No. AXU72721, computer printout, pp. 16-18 (For SEQ ID No. 24).*
GenBank Accession No. BC012160, "*Homo sapiens* CD27 molecule, mRNA (cDNA clone MGC:20393 IMAGE:4575359), complete cds," GenBank, Aug. 2, 2001, 4 pages.
GenBank Accession No. XM006505898.3, "PREDICTED: Mus musculus CD27 antigen (Cd27), transcript variant X1, mRNA," GenBank, Jun. 22, 2016, 4 pages.
Akiba et al., "CD27, a member of the tumor necrosis factor receptor superfamily, activates NF-kB and stress-activated protein kinase/c-Jun N-terminal kinase via TRAF2, TRAF5, and NF-kB-inducing kinase," Journal of Biological Chemistry, 1998, 273(21):13353-13358.

(Continued)

*Primary Examiner* — Shin Lin Chen
(74) *Attorney, Agent, or Firm* — Fish & Richardson P.C.

(57) ABSTRACT

The present disclosure relates to genetically modified non-human animals (e.g., genetically-modified mice) that express a human or chimeric (e.g., humanized) CD27. The present disclosure also relates to methods of generating the genetically-modified animals (e.g., genetically modified mice), and methods of using the genetically modified non-human animals (e.g., genetically modified mice) described herein.

12 Claims, 23 Drawing Sheets

Specification includes a Sequence Listing.

(56) References Cited

OTHER PUBLICATIONS

Auerbach et al., "Establishment and Chimera Analysis of 129/SvEv- and C57CL/6-Derived Mouse Embryonic Stem Cell Lines," 2000.
Festing et al., "Revised nomenclature for strain 129 mice," Mammalian Genome, 1999, 10:836.
He et al., "Agonist anti-human CD27 monoclonal antibody induces T-cell activation and tumor immunity in Human CD27-transgenic mice," The Journal of Immunology, 2013, 191(8):4174-4183.
International Search Report and Written Opinion in International Appln. No. PCT/CN2017/117984, dated Mar. 14, 2018, 9 pages.
Ito, M. et al., NOD/SCID/ γcnull mouse: an excellent recipient mouse model for engraftment of human cells, Blood 100(9):3175-3182, 2002.
Nemunaitis et al., "Phase 1 dose escalation of ONT-10, a therapeutic MUC1 vaccine, in patients with advanced cancer," Breast, 2013, 1(2):3.
Prasad et al., "CD27, a member of the tumor necrosis factor receptor family, induces apoptosis and binds to Siva, a proapoptotic protein," Proceedings of the National Academy of Sciences, 1997, 94(12):6346-6351.
Yamamoto et al., "Nf-kB activation in CD27 signaling: involvement of TNF receptor-associated factors in its signaling and identification of functional region of CD27," Journal of Immunology, 1998, 161(9):4753-4759.
Yin et al., "Delivery technologies for genome editing," Nature Reviews Drug Discovery, 2017, 16(6):387-399.

\* cited by examiner

FIG. 14

```
          Score       Expect    Method                         Identities        Positives      Gaps
         333 bits (855) 4e-121  Compositional matrix adjust.   168/260(65%)      190/260(73%)   10/260(3%)

Mouse      1    MAWPPPYWLCMLGTLVGLSATLAPNSCPDKHYWTGGGLCCRMCEPGTFFVKDCEQDRTAA   60
                MA P P+WLC+LGTLVGLSAT AP SCP+HYW  G LCC+MCEPGTF VKDC+Q R AA
Human      1    MARPHPWWLCVLGTLVGLSATPAPKSCPERHYWAQGKLCCQMCEPGTFLVKDCDQHRKAA   60

Mouse     61    QCDPCIPGTSFSPDYHTRPHCESCRHCNSGFLIRNCTVTANAECSCSKNWQCRDQECTEC  120
                QCDPCIPG SFSPD+HTRPHCESCRHCNSG L+RNCT+TANAEC+C    WQCRD+ECTEC
Human     61    QCDPCIPGVSFSPDHHTRPHCESCRHCNSGLLVRNCTITANAECACRNGWQCRDKECTEC  120

Mouse    121    DPPLNPALTRQPSETPSPQPPPTHLPHGTE------KPSWPLHRQLPNSTVYSQRSS     171
                DP  NP+LT + S+  SP P PTHLP+ +E         RQLP  T+ +
Human    121    DPLPNPSLTARSSQALSPHPQPTHLPYVSEMLEARTAGHMQTLADFRQLPARTLSTHWPP  180

Mouse    172    HRPLCSSDCIRIFVTFSSMFLIFVLGAILFFHQRRNHGPNEDRQAV-PEEPCPYSCPREE  230
                 R LCSSD IRI V FS MFL+F L  LF HQRR + N+   V P EPC YSCPREE
Human    181    QRSLCSSDFIRILVIFSGMFLVFTLAGALFLHQRRKYRSNKGESPVEPAEPCRYSCPREE  240

Mouse    231    EGSAIPIQEDYRKPEPAFYP  250
                EGS IPIQEDYRKPEPA  P
Human    241    EGSTIPIQEDYRKPEPACSP  260
```

GENETICALLY MODIFIED NON-HUMAN ANIMAL WITH HUMAN OR CHIMERIC CD27

CLAIM OF PRIORITY

This application is a continuation of and claims priority to international Application No. PCT/CN2017/117984, filed Dec. 22, 2017, which claims the benefit of Chinese Patent Application No. 201611206266.7, filed on Dec. 23, 2016, and Chinese Patent Application No. 20171 1402264.X, filed on Dec. 22, 2017. The entire contents of the foregoing are incorporated herein by reference.

TECHNICAL FIELD

This disclosure relates to genetically modified animal expressing human or chimeric (e.g., humanized) CD27, and methods of use thereof.

BACKGROUND

The immune system has developed multiple mechanisms to prevent deleterious activation of T cells. One such mechanism is the intricate balance between positive and negative costimulatory signals delivered to T cells. Targeting the stimulatory or inhibitory pathways for the immune system is considered to be a potential approach for the treatment of various diseases, e.g., cancers, and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human CD27 or chimeric CD27. The animal model can express human CD27 or chimeric CD27 (e.g., humanized CD27) protein in its body. It can be used in the studies on the function of CD27 gene, and can be used in the screening and evaluation of anti-human CD27 antibodies. In addition, the animal models prepared by the methods described herein can be used in drug screening, pharmacodynamics studies, treatments for immune-related diseases (e.g., autoimmune disease), and cancer therapy for human CD27 target sites; in addition, they can be used to facilitate the development and design of new drugs, and save time and cost. In summary, this disclosure provides a powerful tool for studying the function of CD27 protein and a platform for screening cancer drugs.

The disclosure also provides CD27 gene knockout mice. In addition, the mice described in the present disclosure can be mated with the mice containing other human or chimeric genes (e.g., chimeric CTLA-4, chimeric PD-1, chimeric PD-L1, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In one aspect, the disclosure relates to genetically-modified, non-human animals whose genome comprises at least one chromosome comprising a sequence encoding a human or chimeric CD27. In some embodiments, the sequence encoding the human or chimeric CD27 is operably linked to an endogenous regulatory element at the endogenous CD27 gene locus in the at least one chromosome. In some embodiments, the sequence encoding a human or chimeric CD27 comprises a sequence encoding an amino acid sequence that is at least 50%, 55%, 65%, 70%, 75%, 80%, 85%, 90%, 95%, 99%, or 100% identical to human CD27 (NP_001233.1 (SEQ ID NO: 18)). In some embodiments, the sequence encoding a human or chimeric CD27 comprises a sequence encoding an amino acid sequence that is at least 50%, 55%, 65%, 70%, 75%, 80%, 85%, 90%, 95%, 99%, or 100% identical to SEQ ID NO: 24. In some embodiments, the sequence encoding a human or chimeric CD27 comprises a sequence encoding an amino acid sequence that corresponds to amino acids 1-183 of SEQ ID NO: 18.

In some embodiments, the animal is a mammal, e.g., a monkey, a rodent or a mouse. In some embodiments, the animal is a C57BL/6 mouse. In some embodiments, the animal does not express endogenous CD27. In some embodiments, the animal has one or more cells expressing human or chimeric CD27. In some embodiments, the expressed human or chimeric CD27 can bind to or interact with human protein CD70. In some embodiments, the expressed human or chimeric CD27 can bind to or interact with endogenous CD70.

In one aspect, the disclosure relates to genetically-modified, non-human animals, wherein the genome of the animals comprises a replacement, at an endogenous CD27 gene locus, of a sequence encoding a region of endogenous CD27 with a sequence encoding a corresponding region of human CD27. In some embodiments, the sequence encoding the corresponding region of human CD27 is operably linked to an endogenous regulatory element at the endogenous CD27 locus, and one or more cells of the animal expresses a chimeric CD27. In some embodiments, the animal does not express endogenous CD27. In some embodiments, the locus of endogenous CD27 is the extracellular region of CD27. In some embodiments, the animal has one or more cells expressing a chimeric CD27 having an extracellular region, a transmembrane region, and a cytoplasmic region, wherein the extracellular region comprises a sequence that is at least 50%, 60%, 70%, 80%, 90%, 95%, or 99% identical to the extracellular region of human CD27. In some embodiments, the extracellular region of the chimeric CD27 has a sequence that has at least 10, 20, 30, 40, 50, 60, 70, 80, 90, or 100 contiguous amino acids that are identical to a contiguous sequence present in the extracellular region of human CD27. In some embodiments, the animal is a mouse, and the sequence encoding the region of endogenous CD27 is exon 1, exon 2, exon 3, exon 4, exon 5, and/or exon 6 of the endogenous mouse CD27 gene. In some embodiments, the animal is heterozygous with respect to the replacement at the endogenous CD27 gene locus. In some embodiments, the animal is homozygous with respect to the replacement at the endogenous CD27 gene locus.

In one aspect, the disclosure relates to methods for making a genetically-modified, non-human animal. The methods involve replacing in at least one cell of the animal, at an endogenous CD27 gene locus, a sequence encoding a region of an endogenous CD27 with a sequence encoding a corresponding region of human CD27. In some embodiments, the sequence encoding the corresponding region of human CD27 comprises exon 1, exon 2, exon 3, exon 4, exon 5, and/or exon 6 of a human CD27 gene. In some embodiments, the sequence encoding the corresponding region of CD27 comprises exon 1, exon 2, exon 3, exon 4, and/or exon 5 (or part thereof, e.g., part of exon 5) of a human CD27 gene. In some embodiments, the sequence encoding the corresponding region of human CD27 encodes amino acids 1-183 of SEQ ID NO: 18. In some embodiments, the region is located within the extracellular region of CD27. In some embodiments, the animal is a mouse, and the sequence encoding the region of the endogenous CD27 locus is exon 1, exon 2, exon 3, exon 4, and part of exon 5 of mouse CD27 gene.

In one aspect, the disclosure relates to non-human animals comprising at least one cell comprising a nucleotide sequence encoding a chimeric CD27 polypeptide, wherein the chimeric CD27 polypeptide comprises at least 50 contiguous amino acid residues that are identical to the corresponding contiguous amino acid sequence of a human CD27, wherein the animal expresses the chimeric CD27. In some embodiments, the chimeric CD27 polypeptide has at least 50 contiguous amino acid residues that are identical to the corresponding contiguous amino acid sequence of a human CD27 extracellular region. In some embodiments, the chimeric CD27 polypeptide comprises a sequence that is at least 90%, 95%, or 99% identical to amino acids 1-183 of SEQ ID NO: 18. In some embodiments, the nucleotide sequence is operably linked to an endogenous CD27 regulatory element of the animal. In some embodiments, the chimeric CD27 polypeptide comprises an endogenous CD27 transmembrane region and/or an endogenous CD27 cytoplasmic region. In some embodiments, the nucleotide sequence is integrated to an endogenous CD27 gene locus of the animal. In some embodiments, the chimeric CD27 has at least one mouse CD27 activity (e.g., interacting with mouse CD70, and promoting immune responses in mice) and/or at least one human CD27 activity (e.g., interacting with human CD70, and promoting immune responses in human).

In one aspect, the disclosure relates to methods of making a genetically-modified mouse cell that expresses a chimeric CD27, the method including: replacing, at an endogenous mouse CD27 gene locus, a nucleotide sequence encoding a region of mouse CD27 with a nucleotide sequence encoding a corresponding region of human CD27, thereby generating a genetically-modified mouse cell that includes a nucleotide sequence that encodes the chimeric CD27, wherein the mouse cell expresses the chimeric CD27. In some embodiments, the chimeric CD27 comprises a signal peptide sequence (e.g., a mouse signal peptide sequence or a human signal peptide sequence), an extracellular region of mouse CD27, an extracellular region of human CD27, a transmembrane and/or a cytoplasmic region of a mouse CD27. In some embodiments, the nucleotide sequence encoding the chimeric CD27 is operably linked to an endogenous CD27 regulatory region, e.g., promoter.

In some embodiments, the animals further comprise a sequence encoding an additional human or chimeric protein. In some embodiments, the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), TNF Receptor Superfamily Member 9 (4-1BB), CD28, CD47, T-Cell Immunoreceptor With Ig And ITIM Domains (TIGIT), Glucocorticoid-Induced TNFR-Related Protein (GITR), T-cell immunoglobulin and mucin-domain containing-3 (TIM-3), or TNF Receptor Superfamily Member 4 (TNFRSF4 or OX40).

In one aspect, the disclosure relates to methods of determining effectiveness of an anti-CD27 antibody for the treatment of cancer, including: administering the anti-CD27 antibody to the animal as described herein, wherein the animal has a tumor, and determining the inhibitory effects of the anti-CD27 antibody to the tumor. In some embodiments, the animal comprises one or more cells (e.g., T cells or B cells) that express CD70.

In some embodiments, the tumor comprises one or more cancer cells that are injected into the animal. In some embodiments, determining the inhibitory effects of the anti-CD27 antibody to the tumor involves measuring the tumor volume in the animal. In some embodiments, the tumor cells are melanoma cells (e.g., advanced melanoma cells), non-small cell lung carcinoma (NSCLC) cells, small cell lung cancer (SCLC) cells, bladder cancer cells, non-Hodgkin lymphoma cells, and/or prostate cancer cells (e.g., metastatic hormone-refractory prostate cancer). In some embodiments, the tumor cells are hepatocellular, ovarian, colon, or cervical tumor cells. In some embodiments, the tumor cells are breast cancer cells, ovarian cancer cells, and/or refractory solid tumor cells.

In one aspect, the disclosure relates to methods of determining effectiveness of an anti-CD27 antibody for the treatment of various immune-related disorders, e.g., autoimmune diseases.

In one aspect, the disclosure relates to methods of determining effectiveness of an anti-CD27 antibody and an additional therapeutic agent for the treatment of a tumor, including administering the anti-CD27 antibody and the additional therapeutic agent to the animal as described herein, wherein the animal has a tumor, and determining the inhibitory effects on the tumor. In some embodiments, the animal or mouse further comprises a sequence encoding an additional human or chimeric protein. In some embodiments, the additional human or chimeric protein is programmed cell death protein 1 (PD-1), CTLA-4, LAG-3, BTLA, PD-L1, 4-1BB, CD28, CD47, TIGIT, TIM-3, GITR, or OX40. In some embodiments, the animal further comprises a sequence encoding a human or chimeric PD-1, PD-L1, or CTLA-4.

In some embodiments, the additional therapeutic agent is an anti-PD-1 antibody or an anti-PD-L1 antibody. In some embodiments, the additional therapeutic agent is an MUC1 vaccine (e.g., ONT-10). A detailed description of ONT-10 can be found, e.g., in Nemunaitis et al. "Phase 1 dose escalation of ONT-10, a therapeutic MUC1 vaccine, in patients with advanced cancer." Breast 1.2 (2013): 3, which is incorporated by reference in its entirety.

In some embodiments, the animal comprises one or more cells (e.g., T cells or B cells) that express CD70. In some embodiments, the tumor comprises one or more tumor cells that express PD-L1 or PD-L2. In some embodiments, the tumor comprises one or more tumor cells that express CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells).

In one aspect, the disclosure relates to proteins comprising an amino acid sequence, wherein the amino acid sequence is one of the following: (a) an amino acid sequence set forth in SEQ ID NO: 24; (b) an amino acid sequence that is at least 90% identical to SEQ ID NO: 24; (c) an amino acid sequence that is at least 91%, 92%, 93%, 94%, 95%, 96%, 97%, 98%, or 99% identical to SEQ ID NO: 24; (d) an amino acid sequence that is different from the amino acid sequence set forth in SEQ ID NO: 24 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 24. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein as described herein; (b) SEQ ID NO: 22; (c) SEQ ID NO: 23; (d) a sequence that is at least 90% identical to SEQ ID NO: 22 or SEQ ID NO: 23; (e) a sequence that is at least 91%, 92%, 93%, 94%, 95%, 96%, 97%, 98%, or 99% identical to SEQ ID NO: 22; and (f) a sequence that is at least 91%, 92%, 93%, 94%, 95%, 96%, 97%, 98%, or 99% identical to SEQ ID NO: 23. In some embodiments, provided herein are cells comprising the nucleic acids disclosed herein. In some embodiments, provided herein are animals having the nucleic acids disclosed herein.

In one aspect, the disclosure relates to a targeting vector, including a) a DNA fragment homologous to the 5' end of a region to be altered (5' arm), which is selected from the CD27 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD27 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000072.6; c) the DNA fragment homologous to the 3' end of the region to be altered (3' arm/receptor) is selected from the nucleotide sequences that have at least 90% homology to the NCBI accession number NC_000072.6.

In some embodiments, a) the DNA fragment homologous to the 5' end of a region to be altered (5' arm/receptor) is selected from the nucleotides from the position 125241195 to the position 125236893 of the NCBI accession number NC_000072.6; c) the DNA fragment homologous to the 3' end of the region to be altered (3' arm/receptor) is selected from the nucleotides from the position 125232413 to the position 125227672 of the NCBI accession number NC_000072.6.

In some embodiments, a length of the selected genomic nucleotide sequence is about 3 kb, 3.5 kb, 4 kb, 4.5 kb, or 5 kb. In some embodiments, the length is about 4303 bp or 4742 bp. In some embodiments, the region to be altered is exon 1, exon 2, exon 3, exon 4, and/or exon 5 of CD27 gene.

In some embodiments, the sequence of the 5' arm is shown in SEQ ID NO: 19. In some embodiments, the sequence of the 3' arm is shown in SEQ ID NO: 20.

In some embodiments, the targeting vector further includes a selectable gene marker.

In some embodiments, the target region is derived from human. In some embodiments, the target region is a part or entirety of the nucleotide sequence of a humanized CD27. In some embodiments, the nucleotide sequence is shown as one or more of the first exon, the second exon, the third exon, the fourth exon, the fifth exon, and the sixth exon of the DNA sequence of the human CD27.

In some embodiments, the nucleotide sequence of the human CD27 encodes the human CD27 protein with the NCBI accession number NP_001233.1 (SEQ ID NO: 18). In some emboldens, the nucleotide sequence of the human CD27 is selected from the nucleotides from the position 6445096 to the position 6450905 of NC_000012.12 (SEQ ID NO:21).

The disclosure also relates to a cell including the targeting vector as described herein.

The disclosure also relates to a method for establishing a genetically-modified non-human animal expressing two human or chimeric (e.g., humanized) genes. The method includes the steps of (a) using the method for establishing a CD27 gene humanized animal model to obtain a CD27 gene genetically modified humanized mouse;

(b) mating the CD27 gene genetically modified humanized mouse obtained in step (a) with another humanized mouse, and then screening to obtain a double humanized mouse model.

In some embodiments, in step (b), the CD27 gene genetically modified humanized mouse obtained in step (a) is mated with a PD-1 or PD-L1 humanized mouse to obtain a CD27 and PD-1 double humanized mouse model or a CD27 and PD-L1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized CD27 gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a CD27 amino acid sequence of a humanized mouse, wherein the amino acid sequence is selected from the group consisting of:

a) an amino acid sequence shown in SEQ ID NO: 24;

b) an amino acid sequence having a homology of at least 90% with the amino acid sequence shown in SEQ ID NO: 24;

c) an amino acid sequence encoded by a nucleic acid sequence, wherein the nucleic acid sequence is able to hybridize to a nucleotide sequence encoding the amino acid shown in SEQ ID NO: 24 under a low stringency condition or a strict stringency condition;

d) an amino acid sequence having a homology of at least 90%, 91%, 92%, 93%, 94%, 95%, 96%, 97%, 98%, or at least 99% with the amino acid sequence shown in SEQ ID NO: 24;

e) an amino acid sequence that is different from the amino acid sequence shown in SEQ ID NO: 24 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 24.

The disclosure also relates to a CD27 nucleic acid sequence of a humanized mouse, wherein the nucleic acid sequence is selected from the group consisting of:

a) a nucleic acid sequence that encodes the CD27 amino acid sequence of a humanized mouse;

b) a nucleic acid sequence that is set forth in SEQ ID NO: 23;

c) a nucleic acid sequence having a coding DNA sequence (CDS) as shown in SEQ ID NO: 22;

d) a nucleic acid sequence that is able to hybridize to the nucleotide sequence as shown in SEQ ID NO: 22 or SEQ ID NO: 23 under a low stringency condition or a strict stringency condition;

e) a nucleic acid sequence that has a homology of at least 90%, 91%, 92%, 93%, 94%, 95%, 96%, 97%, 98%, or at least 99% with the nucleotide sequence as shown in SEQ ID NO: 22 or SEQ ID NO: 23;

f) a nucleic acid sequence that encodes an amino acid sequence, wherein the amino acid sequence has a homology of at least 90% with the amino acid sequence shown in SEQ ID NO: 24;

g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 24;

h) a nucleic acid sequence that encodes an amino acid sequence, wherein the amino acid sequence is different from the amino acid sequence shown in SEQ ID NO: 24 by no more than 10, 9, 8, 7, 6, 5, 4, 3, 2 or no more than 1 amino acid; and/or i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 24.

The disclosure further relates to a CD27 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CD27 gene function, human CD27 antibodies, the drugs or efficacies for human CD27 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

In FIGS. 11A-11B, M indicates the marker, + indicates a positive control mouse that is homozygous for humanized CD27, and − indicates a control wildtype mouse; In FIGS. 9C-9D, WT indicates wildtype mouse; +/− indicates a control mouse that is heterozygous for humanized PD-1; and −/− indicates a control mouse that is homozygous for humanized PD-1.

FIGS. 12A and 12D show the results of a C57BL/6 wildtype mouse without mouse anti-CD3 antibody stimulation. FIGS. 12B and 12E show the results of a C57BL/6 wildtype mouse with mouse anti-CD3 antibody stimulation. FIGS. 12C and 12F show the results of a humanized mouse that is homozygous for both humanized CD27 and humanized PD-1 with mouse anti-CD3 antibody stimulation. The spleen cells were stained with 1) antibody against mouse CD27 (anti-mCD27 (APC)) and antibody against mouse TcRβ (anti-mTcRβ) (FIGS. 12A-12C); and 2) antibody against human CD27 (anti-hCD27 (PE)), and antibody against mouse TcRβ (anti-mTcRβ) (FIGS. 12D-12F).

FIGS. 13A and 13D show the results of a C57BL/6 wildtype mouse without mouse anti-CD3 antibody stimulation. FIGS. 13B and 13E show the results of a C57BL/6 wildtype mouse with mouse anti-CD3 antibody stimulation. FIGS. 13C and 13F show the results of a humanized mouse that is homozygous for both humanized CD27 and humanized PD-1 with mouse anti-CD3 antibody stimulation. The spleen cells were stained with 1) antibody against mouse PD-1 (anti-mPD-1 (PE)) and antibody against mouse TcRβ (anti-mTcRβ) (FIGS. 13A-13C); and 2) antibody against human PD-1 (anti-hPD-1 (FITC)), and antibody against mouse TcRβ (anti-mTcRβ) (FIGS. 13D-13F).

FIG. 14 shows results from RT-PCR. +/+ indicates wildtype C57BL/6 mice; H/H indicates mice that are homozygous for both humanized CD27 and humanized PD-1; and GAPDH was used as a control.

In FIGS. 16A-16B, M indicates the marker, + indicates a positive control mouse that is homozygous for humanized CD27, and − indicates a control wildtype mouse; In FIGS. 16C-16D, + indicates a positive control mouse that is heterozygous for humanized PD-1, and − indicates a control wildtype mouse.

FIG. 23 shows the alignment between mouse CD27 amino acid sequence (NP_001028298.1; SEQ ID NO: 16) and human CD27 amino acid sequence (NP_001233.1; SEQ ID NO: 18).

DETAILED DESCRIPTION

Figure 1:
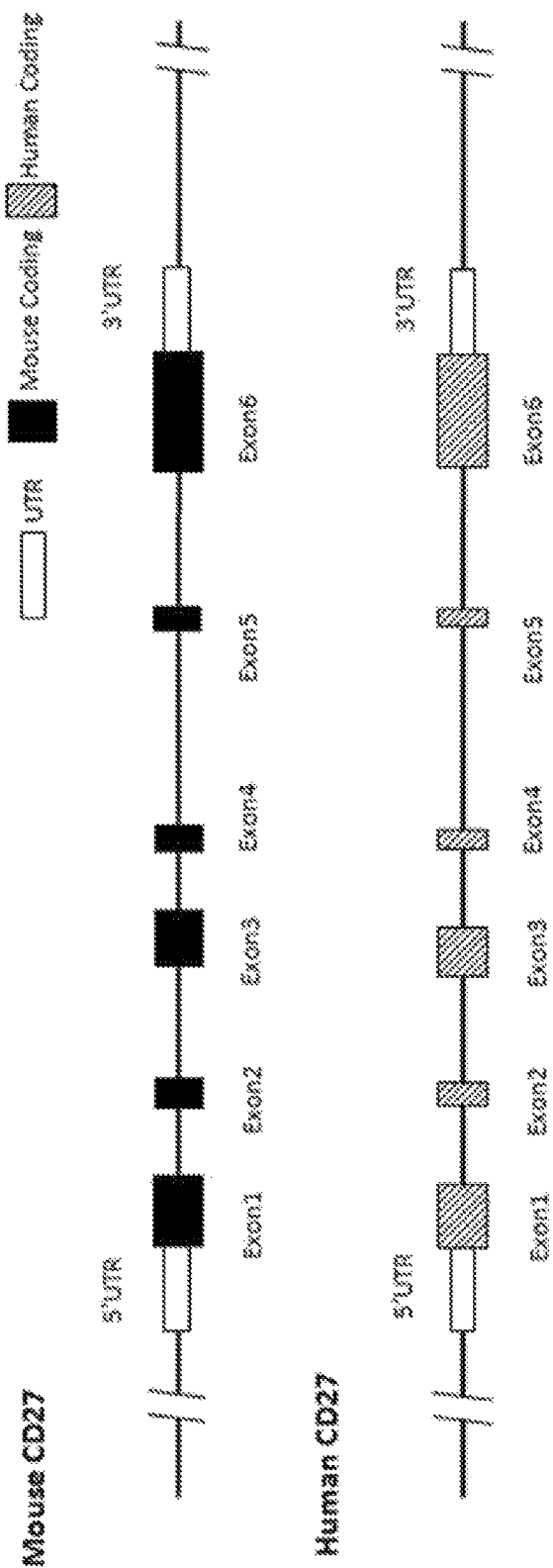
FIG. 1 is a schematic diagram showing human and mouse CD27 genes.

This disclosure relates to transgenic non-human animal with human or chimeric (e.g., humanized) CD27, and methods of use thereof.

CD27 (also known as Tumor Necrosis Factor Receptor Superfamily Member 7 or TNFRSF7) is a member of the tumor necrosis factor receptor superfamily. It is a co-stimulatory immune checkpoint receptor. This receptor is required for generation and long-term maintenance of T cell immunity. It binds to ligand CD70, and plays a key role in regulating B-cell activation and immunoglobulin synthesis. This receptor transduces signals that lead to the activation of NF-κB and MAPK8/JNK. Adaptor proteins TRAF2 and TRAF5 have been shown to mediate the signaling process of this receptor. Certain anti-CD27 antibodies can activate T-cells and promote immune response. These antibodies (e.g., Varlilumab) can be used to treat various cancers, e.g., advanced breast or ovarian cancer, or advanced refractory solid tumors. However, not all antibodies have the same effects. Some anti-CD27 antibodies may inhibit immune response instead.

Experimental animal models are an indispensable research tool for studying the effects of these antibodies. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullis et al U.S. Pat. No. 4,683,195; Nucleic Acid Hybridization (B. D. Hames& S. J. Higginseds. 1984); Transcription And Translation (B. D. Hames& S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

CD27

CD27 is a glycosylated, type I transmembrane protein of about 55 kDa and exists as homodimers with a disulfide bridge linking the two monomers. The disulfide bridge is in the extracellular domain close to the membrane. The ligand for CD27 is CD70, which belongs to the TNF family of ligands, and is a type II transmembrane protein with an apparent molecular mass of 50 kDa.

Because of CD70's homology to TNFα and TNFβ, especially in β strands C, D, H, and I, CD70 is predicted to have a trimeric structure, made up of three identical subunits, possibly interacting with three CD27 homodimers.

Expression of both CD27 and its ligand, CD70, is restricted to discrete populations of both T and B cells. Although CD27 is expressed on the surface of resting T cells, CD70 appears only on activated T and B cells. Within the T cell subsets, CD27 is stably expressed on the CD45RA+ population of T cells even after activation, whereas on CD45RO+ cells, it is weakly expressed and lost after activation. On CD45RA+ cells, activation by various means results in the up-regulation of CD27 expression.

Although CD70 is not detectable on either CD45RA+ or CD45RO+ resting T cells, activation through the TcR-CD3 complex results in the expression of CD70 predominantly on CD45RO+ CD4+ T cells. The reciprocal expression of CD27 and CD70 on subsets of helper cells suggested an important role for the molecules in T cell-T cell interactions, T cell activation, and regulation of Ig synthesis. Significant amounts of CD27 can also be detected on a subpopulation of B cells present in peripheral blood and tonsils, and the expression can be enhanced after activation with phorbol 12-myristate 13-acetate/ionomycin. CD27 is also expressed on the CD3-bright thymocytes and can be induced in low CD3, CD4+, and CD8+(double-positive) cells after activation with ConA and phorbol 12-mysristate 13-acetate/ionomycin. In contrast, in murine systems, CD27 is constitutively expressed on all thymocytes. CD27 is also highly expressed in most of the B cell non-Hodgkin lymphomas and B cell chronic lymphocytic leukemias. The B cell lines Ramos and Raji express significant levels of both CD27 and its ligand, CD70.

CD27 is functionally similar to other co-stimulatory receptors OX40, 4-1BB, and the herpesvirus entry mediator (HVEM). Similar to HVEM, CD27 can activate both NF-κB and SAPK/JNK pathways, which are mediated by TRAF2 and TRAF5. It has also been determined that the 13-amino acid region of the CD27 molecule (e.g., residues 238-250 amino acids of human CD27 SEQ ID NO: 18) is needed for the NF-κB-activating signal, and also for its interaction with TRAFs.

CD27/CD70 interaction can result in the generation of cytolytic T cells. Ligation of CD27 with CD70 on B cells significantly enhances IgG production, with a less pronounced effect on cell proliferation. The CD27-mediated costimulatory effect can be specifically inhibited by the addition of anti-CD27 antibody, or recombinant sCD27 (soluble) or anti-CD70 antibody. Thus, anti-CD27 antibody can be used to inhibit CD27-mediated costimulatory effect. However, in some cases, certain anti-CD27 antibodies can promote the CD27-mediated costimulatory effect. These antibodies presumably target different epitopes on CD27, and can be potentially used to treat various cancers.

A detailed description of CD27 and its function can be found, e.g., in Prasad et al. "CD27, a member of the tumor necrosis factor receptor family, induces apoptosis and binds to Siva, a proapoptotic protein." Proceedings of the National Academy of Sciences 94.12 (1997): 6346-6351; Akiba, et al. "CD27, a member of the tumor necrosis factor receptor superfamily, activates NF-κB and stress-activated protein kinase/c-Jun N-terminal kinase via TRAF2, TRAF5, and NF-κB-inducing kinase." Journal of Biological Chemistry 273.21 (1998): 13353-13358; Yamamoto et al. "NF-κB activation in CD27 signaling: involvement of TNF receptor-associated factors in its signaling and identification of functional region of CD27." The Journal of Immunology 161.9 (1998): 4753-4759; each of which is incorporated by reference in its entirety.

In human genomes, CD27 gene locus has six exons, exon 1, exon 2, exon 3, exon 4, exon 5, and exon 6 (FIG. 1). The CD27 protein also has an extracellular region, a transmembrane region, and a cytoplasmic region, and the signal peptide is located at the extracellular region of CD27. The nucleotide sequence for human CD27 mRNA is NM_001242.4 (SEQ ID NO: 17), and the amino acid sequence for human CD27 is NP_001233.1 (SEQ ID NO: 18). The location for each exon and each region in human CD27 nucleotide sequence and amino acid sequence is listed below:

TABLE 1

| Human CD27 (approximate location) | NM_001242.4 1320 bp (SEQ ID NO: 17) | NP_001233.1 260 aa (SEQ ID NO: 18) |
| --- | --- | --- |
| Exon 1 | 1-347 | 1-45 |
| Exon 2 | 348-479 | 46-89 |
| Exon 3 | 480-659 | 90-149 |
| Exon 4 | 660-749 | 150-179 |
| Exon 5 | 750-869 | 180-219 |
| Exon 6 | 870-1320 | 220-260 |
| Signal peptide | 212-268 | 1-19 |
| Extracellular region (excluding signal peptide region) | 269-784 | 20-191 |
| Transmembrane region | 785-847 | 192-212 |
| Cytoplasmic region | 848-991 | 213-260 |
| Donor region | 212-760 | 1-183 |

Similarly, in mice, CD27 gene locus has six exons, exon 1, exon 2, exon 3, exon 4, exon 5, and exon 6 (FIG. 1). The CD27 protein also has an extracellular region, a transmembrane region, and a cytoplasmic region, and the signal peptide is located at the extracellular region of CD27. The nucleotide sequence for mouse CD27 cDNA is NM_001033126.2 (SEQ ID NO: 15), the amino acid sequence for mouse CD27 is NP_001028298.1 (SEQ ID NO: 16). The location for each exon and each region in the mouse CD27 nucleotide sequence and amino acid sequence is listed below:

TABLE 2

| Mouse CD27 (approximate location) | NM_001033126.2 1576 bp (SEQ ID NO: 15) | NP_001028298.1 250 aa (SEQ ID NO: 16) |
| --- | --- | --- |
| Exon 1 | 1-271 | 1-45 |
| Exon 2 | 272-403 | 46-89 |
| Exon 3 | 404-583 | 90-149 |
| Exon 4 | 584-646 | 150-170 |
| Exon 5 | 647-766 | 171-210 |
| Exon 6 | 767-1576 | 211-250 |
| Signal peptide | 136-198 | 1-21 |
| Extracellular region (excluding signal peptide region) | 199-675 | 22-180 |
| Transmembrane region | 676-741 | 181-202 |
| Cytoplasmic region | 742-885 | 203-250 |
| Replaced region in Example | 136-657 | 1-174 |

The mouse CD27 gene (Gene ID: 21940) is located in Chromosome 6 of the mouse genome, which is located from 125232620 to 125237027 of NC_000072.6 (GRCm38.p4 (GCF_000001635.24)). The 5'-UTR is from 125237010 to 125236893, exon 1 is from 125236892 to 125236757, the first intron is from 125236756 to 125236605, exon 2 is from 125236604 to 125236473, the second intron is from 125236472 to 125234695, exon 3 is from 125234694 to 125234515, the third intron is from 125234514 to 125234317, exon 4 is from 125234316 to 125234254, the fourth intron is from 125234253 to 125233762, exon 5 is from 125233761 to 125233642, the fifth intron is from 125233641 to 125233432, exon 6 is from 125233431 to 125233310, the 3'-UTR is from 125233309 to 125232622, based on transcript NM_001033126.2. All relevant information for mouse CD3 locus can be found in the NCBI website with Gene ID: 21940, which is incorporated by reference herein in its entirety.

FIG. 23 shows the alignment between mouse CD27 amino acid sequence (NP_001028298.1; SEQ ID NO: 16) and human CD27 amino acid sequence (NP_001233.1; SEQ ID NO: 18). Thus, the corresponding amino acid residue or region between human and mouse CD27 can also be found in FIG. 23.

CD27 genes, proteins, and locus of the other species are also known in the art. For example, the gene ID for CD27 in *Rattus norvegicus* is 500318, the gene ID for CD27 in *Macaca mulatta* (Rhesus monkey) is 712693, the gene ID for CD27 in *Canis lupus familiaris* (dog) is 611674. The relevant information for these genes (e.g., intron sequences, exon sequences, amino acid residues of these proteins) can be found, e.g., in NCBI database.

The present disclosure provides human or chimeric (e.g., humanized) CD27 nucleotide sequence and/or amino acid sequences. In some embodiments, the entire sequence of mouse exon 1, exon 2, exon 3, exon 4, exon 5, exon 6, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, signal peptide, extracellular region, transmembrane region, or cytoplasmic region. In some embodiments, a region, a portion, or the entire sequence of mouse exon 1, exon 2, exon 3, exon 4, exon 5, and/or exon 6 (e.g., exon 1, exon 2, exon 3, exon 4, exon 5) are replaced by the human exon 1, exon 2, exon 3, exon 4, exon 5, and/or exon 6, (e.g., exon 1, exon 2, exon 3, exon 4, exon 5) sequence.

In some embodiments, the present disclosure also provides a chimeric (e.g., humanized) CD27 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CD27 mRNA sequence (e.g., SEQ ID NO: 15), mouse CD27 amino acid sequence (e.g., SEQ ID NO: 16), or a portion thereof (e.g., exon 1, exon 2, exon 3, exon 4, and exon 5); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CD27 mRNA sequence (e.g., SEQ ID NO: 17), human CD27 amino acid sequence (e.g., SEQ ID NO: 18), or a portion thereof (e.g., exon 1, exon 2, exon 3, exon 4, and exon 5).

In some embodiments, the sequence encoding amino acids 1-174 of mouse CD27 (SEQ ID NO: 16) is replaced. In some embodiments, the sequence is replaced by a sequence encoding a corresponding region of human CD27 (e.g., amino acids 1-183 of human CD27 (SEQ ID NO: 18).

In some embodiments, the nucleic acids as described herein are operably linked to a promotor or regulatory element, e.g., an endogenous mouse CD27 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CD27 nucleotide sequence (e.g., exon 1, exon 2, exon 3, exon 4, exon 5, exon 6, or NM_001033126.2 (SEQ ID NO: 15)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CD27 nucleotide sequence (e.g., exon 1, exon 2, exon 3, exon 4, exon 5, exon 6, or NM_001033126.2 (SEQ ID NO: 15)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CD27 nucleotide sequence (e.g., exon 1, exon 2, exon 3, exon 4, exon 5, exon 6, or NM_001242.4 (SEQ ID NO: 17)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CD27 nucleotide sequence (e.g., exon 1, exon 2, exon 3, exon 4, exon 5, exon 6, or NM_001242.4 (SEQ ID NO: 17)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CD27 amino acid sequence (e.g., exon 1, exon 2, exon 3, exon 4, exon 5, exon 6, or NP_001028298.1 (SEQ ID NO: 16)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CD27 amino acid sequence (e.g., exon 1, exon 2, exon 3, exon 4, exon 5, exon 6, or NP_001028298.1 (SEQ ID NO: 16)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CD27 amino acid sequence (e.g., exon 1, exon 2, exon 3, exon 4, exon 5, exon 6, or NP_001233.1 (SEQ ID NO: 18)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CD27 amino acid sequence (e.g., exon 1, exon 2, exon 3, exon 4, exon 5, exon 6, or NP_001233.1 (SEQ ID NO: 18)).

The present disclosure also provides a humanized CD27 mouse amino acid sequence, wherein the amino acid sequence is selected from the group consisting of:

a) an amino acid sequence shown in SEQ ID NO: 24;

b) an amino acid sequence having a homology of at least 90% with or at least 90% identical to the amino acid sequence shown in SEQ ID NO: 24;

c) an amino acid sequence encoded by a nucleic acid sequence, wherein the nucleic acid sequence is able to hybridize to a nucleotide sequence encoding the amino acid shown in SEQ ID NO: 24 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 24;

e) an amino acid sequence that is different from the amino acid sequence shown in SEQ ID NO: 24 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 24.

The present disclosure also relates to a CD27 nucleic acid sequence, wherein the nucleic acid sequence can be selected from the group consisting of:

a) a nucleic acid sequence as shown in SEQ ID NO: 22, or a nucleic acid sequence encoding a homologous CD27 amino acid sequence of a humanized mouse;

b) a nucleic acid sequence that is shown in SEQ ID NO: 23;

c) a nucleic acid sequence that is able to hybridize to the nucleotide sequence as shown in SEQ ID NO: 22 or SEQ ID NO: 23 under a low stringency condition or a strict stringency condition;

d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 22 or SEQ ID NO: 23;

e) a nucleic acid sequence that encodes an amino acid sequence, wherein the amino acid sequence has a homology of at least 90% with or at least 90% identical to the amino acid sequence shown in SEQ ID NO: 24;

f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 24;

g) a nucleic acid sequence that encodes an amino acid sequence, wherein the amino acid sequence is different from the amino acid sequence shown in SEQ ID NO: 24 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 24.

The present disclosure further relates to a CD27 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 22 or SEQ ID NO: 23.

The disclosure also provides an amino acid sequence that has a homology of at least 90% with, or at least 90% identical to the sequence shown in SEQ ID NO: 24, and has protein activity. In some embodiments, the homology with the sequence shown in SEQ ID NO: 24 is at least about 90%, 91%, 92%, 93%, 94%, 95%, 96%, 97%, 98%, or at least 99%. In some embodiments, the foregoing homology is at least about 65%, 66%, 67%, 68%, 69%, 70%, 71%, 72%, 73%, 74%, 75%, 80%, or 85%.

In some embodiments, the percentage identity with the sequence shown in SEQ ID NO: 24 is at least about 90%, 91%, 92%, 93%, 94%, 95%, 96%, 97%, 98%, or at least 99%. In some embodiments, the foregoing percentage identity is at least about 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 23, and encodes a polypeptide that has protein activity. In some embodiments, the homology with the sequence shown in SEQ ID NO: 23 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 23 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, or 190 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of identical residues (percent identity) and the percentage of residues conserved with similar physicochemical properties (percent homology), e.g. leucine and isoleucine, can be used to measure sequence similarity. Residues conserved with similar physicochemical properties are well known in the art. The percent homology, in many cases, is higher than the percent identity.

Cells, tissues, and animals (e.g., mouse) are also provided that comprise the nucleotide sequences as described herein, as well as cells, tissues, and animals (e.g., mouse) that express human or chimeric (e.g., humanized) CD27 from an endogenous non-human CD27 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous CD27 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized CD27 gene or a humanized CD27 nucleic acid. In some embodiments, at least one or more portions of the gene or the nucleic acid is from the human CD27 gene, at least one or more portions of the gene or the nucleic acid is from a non-human CD27 gene. In some embodiments, the gene or the nucleic acid comprises a sequence that encodes a CD27 protein. The encoded CD27 protein is functional or has at least one activity of the human CD27 protein or the non-human CD27 protein, e.g., binding to human or non-human CD70, regulating immune response, activating NF-κB or SAPK/JNK pathways, and/or stimulating immune response.

In some embodiments, the chimeric protein or the chimeric polypeptide is a humanized CD27 protein or a humanized CD27 polypeptide. In some embodiments, at least one or more portions of the amino acid sequence of the protein or the polypeptide is from a human CD27 protein, and at least one or more portions of the amino acid sequence of the protein or the polypeptide is from a non-human CD27 protein. The humanized CD27 protein or the humanized CD27 polypeptide is functional or has at least one activity of the human CD27 protein or the non-human CD27 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/01a. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/ SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/ SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized CD27 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/ SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human CD27 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/ SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature CD27 coding sequence with human mature CD27 coding sequence.

Genetically modified non-human animals that comprise a modification of an endogenous non-human CD27 locus. In some embodiments, the modification can comprise a human nucleic acid sequence encoding at least a portion of a mature CD27 protein (e.g., at least 10%, 20%, 30%, 40%, 50%, 60%, 70%, 80%, 90%, 95%, 96%, 97%, 98%, or 99% identical to the mature CD27 protein sequence). Although genetically modified cells are also provided that can comprise the modifications described herein (e.g., ES cells, somatic cells), in many embodiments, the genetically modified non-human animals comprise the modification of the endogenous CD27 locus in the germline of the animal.

Genetically modified animals can express a human CD27 and/or a chimeric (e.g., humanized) CD27 from endogenous mouse loci, wherein the endogenous mouse CD27 gene has been replaced with a human CD27 gene and/or a nucleotide sequence that encodes a region of human CD27 sequence or an amino acid sequence that is at least 10%, 20%, 30%, 40%, 50%, 60%, 70&, 80%, 90%, 95%, 96%, 97%, 98%, or 99% identical to the human CD27 sequence. In various embodiments, an endogenous non-human CD27 locus is modified in whole or in part to comprise human nucleic acid sequence encoding at least one protein-coding sequence of a mature CD27 protein.

In some embodiments, the genetically modified mice express the human CD27 and/or chimeric CD27 (e.g., humanized CD27) from endogenous loci that are under control of mouse promoters and/or mouse regulatory elements. The replacement(s) at the endogenous mouse loci provide non-human animals that express human CD27 or chimeric CD27 (e.g., humanized CD27) in appropriate cell types and in a manner that does not result in the potential pathologies observed in some other transgenic mice known in the art. The human CD27 or the chimeric CD27 (e.g., humanized CD27) expressed in animal can maintain one or more functions of the wildtype mouse or human CD27 in the animal. For example, human or non-human CD27 ligands (e.g., CD70) can bind to the expressed CD27 and upregulate immune response, e.g., upregulate immune response by at least 10%, 20%, 30%, 40%, or 50%. Furthermore, in some embodiments, the animal does not express endogenous CD27. As used herein, the term "endogenous CD27" refers to CD27 protein that is expressed from an endogenous CD27 nucleotide sequence of the genetically modified non-human animal (e.g., mouse) before the genetic modification.

The genome of the animal can comprise a sequence encoding an amino acid sequence that is at least 70%, 75%, 80%, 85%, 90%, 95%, 99%, or 100% identical to human CD27 (NP_001233.1) (SEQ ID NO: 18). In some embodiments, the genome comprises a sequence encoding an amino acid sequence that is at least 70%, 75%, 80%, 85%, 90%, 95%, 99%, or 100% identical to SEQ ID NO: 24.

The genome of the genetically modified animal can comprise a replacement at an endogenous CD27 gene locus of a sequence encoding a region of endogenous CD27 with a sequence encoding a corresponding region of human CD27. In some embodiments, the sequence that is replaced is any sequence within the endogenous CD27 gene locus, e.g., exon 1, exon 2, exon 3, exon 4, exon 5, exon 6, 5'-UTR, 3'UTR, the first intron, the second intron, and the third intron, the fourth intron, the fifth intron, etc. In some embodiments, the sequence that is replaced is within the regulatory region of the endogenous CD27 gene. In some embodiments, the sequence that is replaced is exon 1, exon 2, exon 3, exon 4, exon 5, or part thereof of an endogenous mouse CD27 gene locus.

The genetically modified animal can have one or more cells expressing a human or chimeric CD27 (e.g., humanized CD27) having an extracellular region and a cytoplasmic region, wherein the extracellular region comprises a sequence that is at least 50%, 60%, 70%, 80%, 90%, 95%, 99% identical to the extracellular region of human CD27. In some embodiments, the extracellular region of the humanized CD27 has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human CD27. Because human CD27 and non-human CD27 (e.g., mouse CD27) sequences, in many cases, are different, antibodies that bind to human CD27 will not necessarily have the same binding affinity with non-human CD27 or have the same effects to non-human CD27. Therefore, the genetically modified animal having a human or a humanized extracellular region can be used to better evaluate the effects of anti-human CD27 antibodies in an animal model. In some embodiments, the genome of the genetically modified animal comprises a sequence encoding an amino acid sequence that corresponds to part or the entire sequence of exon 1, exon 2, exon 3, exon 4, exon 5, and/or exon 6 of human CD27, part or the entire sequence of extracellular region of human CD27 (with or without signal peptide), or part or the entire sequence of amino acids 1-183 of SEQ ID NO: 18.

In some embodiments, the non-human animal can have, at an endogenous CD27 gene locus, a nucleotide sequence encoding a chimeric human/non-human CD27 polypeptide, wherein a human portion of the chimeric human/non-human CD27 polypeptide comprises a portion of human CD27 extracellular domain, and wherein the animal expresses a functional CD27 on a surface of a cell of the animal. The human portion of the chimeric human/non-human CD27 polypeptide can comprise a portion of exon 1, exon 2, exon 3, exon 4, exon 5, and/or exon 6 of human CD27. In some embodiments, the human portion of the chimeric human/non-human CD27 polypeptide can comprise a sequence that is at least 80%, 85%, 90%, 95%, or 99% identical to amino acids 1-183 of SEQ ID NO: 18.

In some embodiments, the non-human portion of the chimeric human/non-human CD27 polypeptide comprises transmembrane and/or cytoplasmic regions of an endogenous non-human CD27 polypeptide. There may be several advantages that are associated with the transmembrane and/or cytoplasmic regions of an endogenous non-human CD27 polypeptide. For example, once a CD27 ligand (e.g., CD70) binds to CD27, they can properly transmit extracellular signals into the cells and regulate the downstream pathway. A human or humanized transmembrane and/or cytoplasmic regions may not function properly in non-human animal cells. In some embodiments, a few extracellular amino acids that are close to the transmembrane region of CD27 are also derived from endogenous sequence. These amino acids may also be important for transmembrane signal transmission.

Furthermore, the genetically modified animal can be heterozygous with respect to the replacement at the endogenous CD27 locus, or homozygous with respect to the replacement at the endogenous CD27 locus.

In some embodiments, the humanized CD27 locus lacks a human CD27 5'-UTR. In some embodiment, the humanized CD27 locus comprises a rodent (e.g., mouse) 5'-UTR. In some embodiments, the humanization comprises a human 3'-UTR. In appropriate cases, it may be reasonable to presume that the mouse and human CD27 genes appear to be similarly regulated based on the similarity of their 5'-flanking sequence. As shown in the present disclosure, humanized CD27 mice that comprise a replacement at an endogenous mouse CD27 locus, which retain mouse regulatory elements but comprise a humanization of CD27 encoding sequence, do not exhibit pathologies. Both genetically modified mice that are heterozygous or homozygous for humanized CD27 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized CD27 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized CD27 in the genome of the animal.

Figure 2:
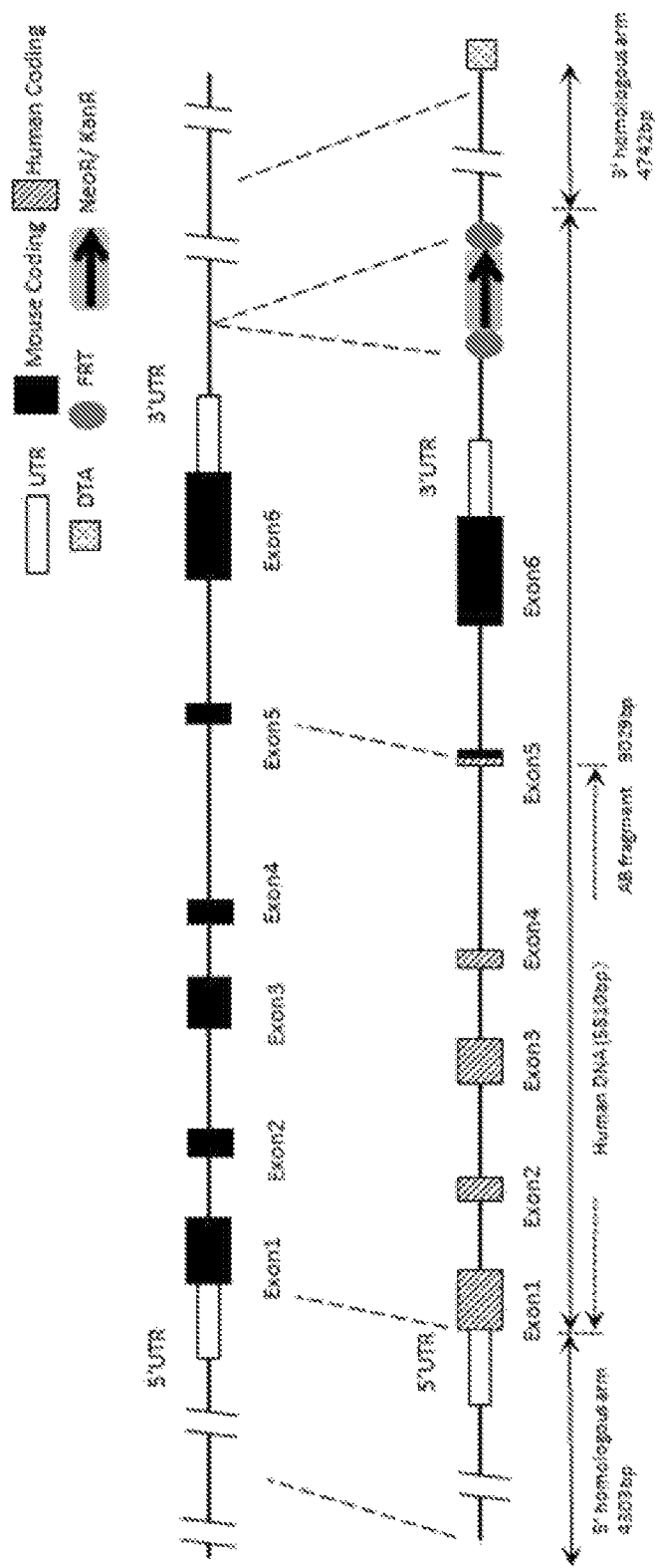
FIG. 2 is a schematic diagram showing mouse CD27 gene targeting strategy.
Figure 3:
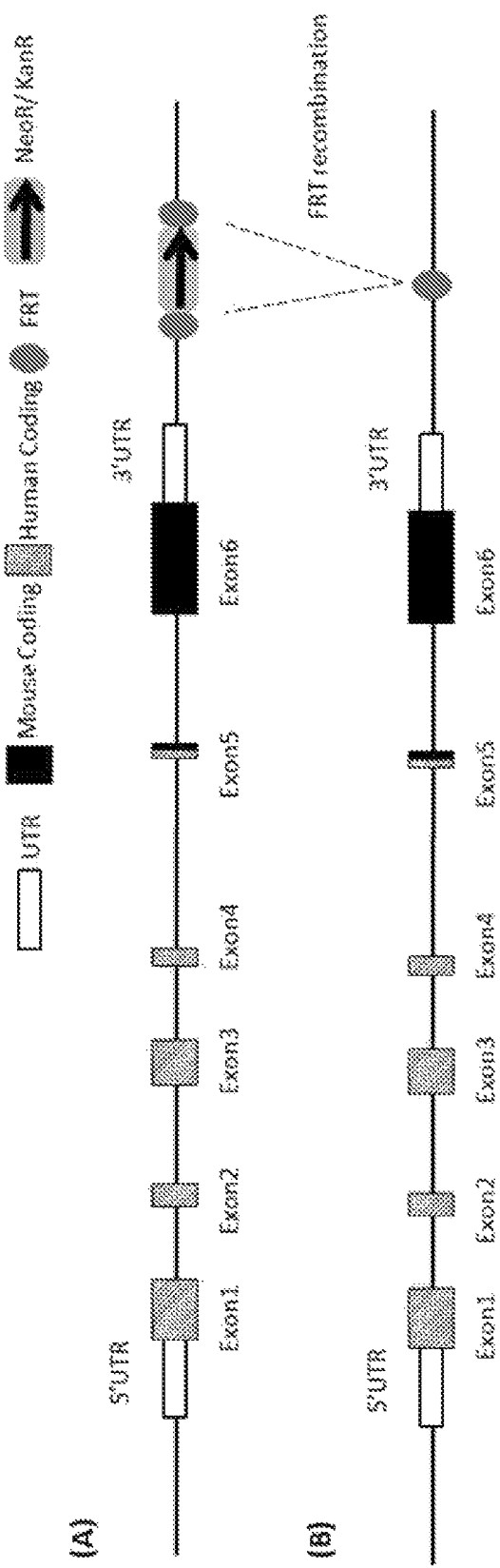
FIG. 3 is a schematic diagram showing humanized CD27 mouse gene map.

In some embodiments, the non-human mammal comprises the genetic construct as described herein (e.g., gene construct as shown in FIG. 2 or FIG. 3). In some embodiments, a non-human mammal expressing human or humanized CD27 is provided. In some embodiments, the tissue-specific expression of human or humanized CD27 protein is provided.

In some embodiments, the expression of human or humanized CD27 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human CD27 protein can be detected by a variety of methods.

There are many analytical methods that can be used to detect exogenous DNA expression, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human CD27 protein.

Vectors

The present disclosure relates to a targeting vector, comprising: a) a DNA fragment homologous to the 5' end of a region to be altered (5' arm), which is selected from the CD27 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD27 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000072.6; c) the DNA fragment homologous to the 3' end of the region to be altered (3' arm) is selected from the nucleotide sequences that have at least 90% homology to the NCBI accession number NC_000072.6.

In some embodiments, a) the DNA fragment homologous to the 5' end of a region to be altered (5' arm) is selected from the nucleotides from the position 125241195 to the position 125236893 of the NCBI accession number NC_000072.6; c) the DNA fragment homologous to the 3' end of the region to be altered (3' arm) is selected from the nucleotides from the position 125232413 to the position 125227672 of the NCBI accession number NC_000072.6.

In some embodiments, the length of the selected genomic nucleotide sequence in the targeting vector can be about 3 kb, about 3.5 kb, about 4 kb, about 4.5 kb, or about 5 kb. In some embodiments, the length is about 4303 bp or about 4742 bp.

In some embodiments, the region to be altered is exon 1, exon 2, exon 3, exon 4, exon 5, and/or exon 6 of CD27 gene (e.g., exon 1, exon 2, exon 3, exon 4, and exon 5 of CD27 gene).

The targeting vector can further include a selected gene marker.

In some embodiments, the sequence of the 5' arm is shown in SEQ ID NO: 19; and the sequence of the 3' arm is shown in SEQ ID NO: 20.

In some embodiments, the sequence is derived from human (e.g., 6445096-6450905 of NC_000012.12). For example, the target region in the targeting vector is a part or entirety of the nucleotide sequence of a human CD27, preferably the nucleotide sequence is shown as a first exon, a second exon, a third exon, a fourth exon, a fifth exon, and/or a sixth exon of the DNA sequence of the human CD27. In some embodiments, the nucleotide sequence of the humanized CD27 encodes the humanized CD27 protein with the NCBI accession number NP_001233.1 (SEQ ID NO: 18).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous CD27 gene locus, a sequence encoding a region of an endogenous CD27 with a sequence encoding a corresponding region of human or chimeric CD27. In some embodiments, the replacement occurs in a germ cell, a somatic cell, a blastocyst, or a fibroblast, etc. The nucleus of a somatic cell or the fibroblast can be inserted into an enucleated oocyte.

FIG. 2 shows a humanization strategy for a mouse CD27 locus. In FIG. 2, the targeting strategy involves a vector comprising the 5' end homologous arm, human CD27 gene fragment, 3' homologous arm. The process can involve replacing endogenous CD27 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous CD27 sequence with human CD27 sequence.

Thus, in some embodiments, the methods for making a genetically modified, humanized animal, can include the step of replacing at an endogenous CD27 locus (or site), a nucleic acid encoding a sequence encoding a region of endogenous CD27 with a sequence encoding a corresponding region of human CD27. The sequence can include a region (e.g., a part or the entire region) of exon 1, exon 2, exon 3, exon 4, exon 5, and/or exon 6 of a human CD27 gene. In some embodiments, the sequence includes a region of exon 1, exon 2, exon 3, exon 4 and exon 5 of a human CD27 gene (e.g., amino acids 1-183 of SEQ ID NO: 18). In some embodiments, the region is located within the extracellular region of CD27. In some embodiments, the endogenous CD27 locus is exon 1, exon 2, exon 3, exon 4 and exon 5 of mouse CD27.

In some embodiments, the methods of modifying a CD27 locus of a mouse to express a chimeric human/mouse CD27 peptide can include the steps of replacing at the endogenous mouse CD27 locus a nucleotide sequence encoding a mouse CD27 with a nucleotide sequence encoding a human CD27, thereby generating a sequence encoding a chimeric human/mouse CD27.

In some embodiments, the nucleotide sequence encoding the chimeric human/mouse CD27 can include a first nucleotide sequence encoding an extracellular region of mouse CD27 (with or without the mouse signal peptide sequence); a second nucleotide sequence encoding an extracellular region of human CD27; a third nucleotide sequence encoding a transmembrane and a cytoplasmic region of a mouse CD27.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a CD27 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized CD27 protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized CD27, which are useful for testing agents that can decrease or block the interaction between CD27 and CD70 or the interaction between CD27 and other ligands, testing whether an agent can increase or decrease the immune response, and/or determining whether an agent is an CD27 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-CD27 antibody for the treatment of cancer. The methods involve administering the anti-CD27 antibody to the animal as described herein, wherein the animal has a tumor; and determining the inhibitory effects of the anti-CD27 antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-CD27 antibody or anti-CD70 antibody prevents CD70 from binding to CD27. In some embodiments, the anti-CD27 antibody or anti-CD70 antibody does not prevent CD70 from binding to CD27.

In some embodiments, the genetically modified animals can be used for determining whether an anti-CD27 antibody is an CD27 agonist or antagonist. In some embodiments, the methods as described herein are also designed to determine the effects of the agent (e.g., anti-CD27 antibodies) on CD27, e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-CD27 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-CD27 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-CD27 antibody is designed for treating hepatocellular, ovarian, colon, or cervical carcinomas. In some embodiments, the anti-CD27 antibody is designed for treating advanced breast cancer, advanced ovarian cancer, and/or advanced refractory solid tumor.

In some embodiments, the anti-CD27 antibody is designed for treating various autoimmune diseases. Thus, the methods as described herein can be used to determine the effectiveness of an anti-CD27 antibody in inhibiting immune response.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the CD27 gene function, human CD27 antibodies, drugs for human CD27 targeting sites, the drugs or efficacies for human CD27 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric CD27 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), TNF Receptor Superfamily Member 9 (4-1BB), CD28, CD47, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), or TNF Receptor Superfamily Member 4 (TNFRSF4; or OX40).

The methods of generating genetically modified animal model with two or more human or chimeric genes (e.g., humanized genes) can include the following steps:

(a) using the methods of introducing human CD27 gene or chimeric CD27 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, 4-1BB, CD28, CD47, TIGIT, TIM-3, GITR, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435; each of which is incorporated herein by reference in its entirety.

In some embodiments, the CD27 humanization is directly performed on a genetically modified animal having a human or chimeric PD-1, CTLA-4, BTLA, PD-L1, 4-1BB, CD28, CD47, TIGIT, TIM-3, GITR, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-CD27 antibody and an additional therapeutic agent for the treatment of cancer. The methods include administering the anti-CD27 antibody and the additional therapeutic agent to the animal, wherein the animal has a tumor; and determining the inhibitory effects of the combined treatment to the tumor.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

C57BL/6 mice and Flp recombinase transgenic mice were purchased from the China Food and Drugs Research Institute National Rodent Experimental Animal Center.

BALB/c mice were obtained from Beijing Vital River Laboratory Animal Technology Co., Ltd.

B-hPD-1 mice and B-hPD-L1 mice were obtained from Beijing Biocytogen Co., Ltd.

BAC clones with mouse CD27 gene and BAC clones with human CD27 gene were purchased from Invitrogen.

Reverse Transcription Kit was obtained from Takara. Catalog number is 6110A.

AIO kit was obtained from Beijing Biocytogen Co., Ltd. Catalog number is BCG-DX-004.

BamHI, EcoRI, XhoI, and HpaI restriction enzymes were purchased from NEB. The catalog numbers are R3136M, R3101M, R0146S, and R0105S.

*E. coli* TOP10 competent cells were purchased from the Tiangen Biotech (Beijing) Co. Catalog number is CB104-02.

APC hamster anti-mouse CD27 (mCD27 APC) antibody was purchased from BD Pharmingen (Catalog number 560691).

PE mouse anti-human CD27 (hCD27 PE) antibody was purchased from BD Pharmingen (Catalog number 557330).

PerCP/Cy5.5 anti-mouse TCR β chain (mTcRβ PerCP) antibody was purchased from Biolegend (Catalog number 109228).

PE anti-mouse CD279 (PD-1) (mPD-1 PE) antibody was purchased from Biolegend (Catalog number 109104).

FITC anti-human CD279 (PD-1) antibody (hPD-1 FITC) was purchased from Biolegend (Catalog number 329904).

APC anti-mouse CD274 (B7-H1, PD-L1) antibody (mPD-L1 APC) was purchased from Biolegend (Catalog number 124312).

PE anti-human CD274 (B7-H1, PD-L1) antibody (hPD-L1 PE) was purchased from Biolegend (Catalog number 329706).

G418 medium was purchased from Thermo Fisher (Catalog number 11811023).

Mouse anti-CD3 antibody was obtained from BD (Catalog number 563123).

Flow cytometer was purchased from BD Biosciences (model: FACS Calibur™)

Example 1: Primer Design and PCR Amplification

Primers for amplifying 7 homologous recombination fragments (A1, A2-1, A2-2, A3, B, C1, C2) were designed and the primer sequences are shown in the table below.

TABLE 3

| Fragments | Length (bp) | Primer sequence |
|---|---|---|
| A1 | 437 bp | F: 5'-cgatctcgagatttaaataatctgtaatctgctcctatctggtc-3' (SEQ ID NO: 1)<br>R: 5'-agggatgtggccgtgccatagctcctgcccagggagatc-3' (SEQ ID NO: 2) |
| A2-1 | 574 bp | F: 5'-gatctccctgggcaggagctatggcacggccacatccct-3' (SEQ ID NO: 3)<br>R: 5'-ggtaggagtggggagtactggttaacccgtcaccagccttgct-3' (SEQ ID NO: 4) |
| A2-2 | 542 bp | F: 5'-agcaaggctggtgacgggttaaccagtactccccactcctacc-3' (SEQ ID NO: 5)<br>R: 5'-gatgcagtccgagctgcacagggatctttgggctgtaataggagg-3' (SEQ ID NO: 6) |
| A3 | 1377 bp | F: 5'-cctcctattacagcccaaagatccctgtgcagctcggactgcatc-3' (SEQ ID NO: 7)<br>R: 5'-cgatgaattcattaatgcatttacactatccttcttcctagttcac-3' (SEQ ID NO: 8) |
| B | 477 bp | F: 5'-cgatggatccaatattcaattgtaacttcaaatacgcacacctacaactga-3' (SEQ ID NO: 9)<br>R: 5'-cgatgcggccgcatttaaatcctttgggtctgccctg-3' (SEQ ID NO: 10) |
| C1 | 468 bp | F: 5'-gctggtaccggcgcgcctcgagaaggaatgtcaagtaccatggctgg-3' (SEQ ID NO: 11)<br>R: 5'-ggagatctggcagatatcacaggggacagcacttac-3' (SEQ ID NO: 12) |
| C2 | 484 bp | F: 5'-ccctgtgatatctgccagatctccacctctctg-3' (SEQ ID NO: 13)<br>R: 5'-tcctcttcagacctggcggccgcttggggataaatcgccttgtatcag-3' (SEQ ID NO: 14) |

KOD-plus DNA polymerase was used to amplify the seven homologous recombination fragments. Among them, mouse BAC clones were used as a template for A1, A3, B, C1, C2 homologous recombination fragments, and human BAC clones were used as a template for A2-1 and A2-2 homologous recombination fragments. The conditions used in the PCR amplification were shown in the tables below.

TABLE 4

| The PCR reaction system (20 μL) | |
|---|---|
| 10x buffer for KOD-plus DNA polymerase | 2 μL |
| dNTP (2 mM) | 2 μL |
| MgSO₄ (25 mM) | 0.8 μL |
| Upstream primer F (10 μM) | 0.6 μL |
| Downstream primer R (10 μM) | 0.6 μL |

TABLE 4-continued

| The PCR reaction system (20 μL) | |
|---|---|
| BAC DNA templates | 50 ng |
| KOD-Plus DNA polymerase (1 U/μL) | 0.6 μL |
| H₂O | Add to 20 μL |

TABLE 5

| The PCR reaction conditions | | |
|---|---|---|
| Temperature | Time | Cycles |
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 57° C. | 30 sec | |
| 68° C. | 1 kb/min | |
| 68° C. | 10 min | 1 |
| 4° C. | 10 min | 1 |

The PCR products (DNA fragments) A1, A2-1, A2-2, A3, B, C1 and C2 were collected and were used to construct homologous recombination targeting vectors.

Example 2. Construction of Homologous Recombination Targeting Vector

The mouse CD27 gene and human CD27 gene are shown in FIG. 1. The targeting strategy is shown in FIG. 2.

The mouse CD27 gene (Gene ID: 21940) (based on the transcript of NCBI accession number NM_001033126.2→NP_001028298.1 whose mRNA sequence is set forth in SEQ ID NO: 15, and the corresponding amino acid sequence is set forth in SEQ ID NO: 16) has 6 exons. Exons 1-5 (the entire exon or the part of the exon) of the mouse CD27 gene were replaced with the corresponding coding sequence of human homologous CD27 gene (Gene ID: 939) (based on the transcript of NCBI accession number NM_001242.4→NP_001233.1, whose mRNA sequence is set forth in SEQ ID NO: 17, and the corresponding protein sequence is set forth in SEQ ID NO: 18). The neo gene was also added after the 3'-UTR for positive clone selection. For the vector, the 5'-homology arm (SEQ ID NO: 19) has a length of 4303 bp, the 3'-homology arm has a length of 4742 bp (SEQ ID NO: 20), and the human DNA fragment has 5810 bp (SEQ ID NO: 21). The modified humanized CD27 was obtained by homologous recombination. The coding region sequence, mRNA sequence and the encoded amino acid sequence thereof of the humanized CD27 are respectively set forth in SEQ ID NO: 22, SEQ ID NO: 23, and SEQ ID NO: 24.

Targeting Vector

The targeting vector was obtained by the following steps:

(1). pBs-Neo-B plasmid was obtained by ligating fragment B and pBs-Neo vector by BamHI/NotI restriction sites. The sequence of pBs-Neo-B plasmid was then verified by sequencing.

(2). Fragment A1 and Fragment A2-1 were ligated by overlap extension PCR (Phusion DNA Polymerases); Fragment A2-2 and Fragment A3 were also ligated by overlap extension PCR (reaction system and conditions are shown in the tables below). The sequences of the products were verified by sequencing. The ligated fragments were further inserted into the pBs-Neo-B plasmid (XhoI/HpaI/EcoRI) to obtain the pBs-Neo-(A1+A2-1+A2-2+A3+B) plasmid.

(3). pBs-Neo-(A1+A2-1+A2-2+A3+B) plasmids were introduced into human BAC clones by electroporation. pBs-Neo-(AB) plasmids, which contains AB fragment (SEQ ID NO: 25; FIG. 2), were obtained by homologous recombination.

(4). pBs-Neo-(AB) plasmids were introduced into mouse BAC clones by electroporation. Mouse BAC clones with AB fragments were obtained by homologous recombination.

(5). pDTA-down-C plasmids were obtained by ligating fragments C1 and C2 to pDTA-down plasmids (AIO kits). The sequences of the plasmids were further verified by sequencing.

(6). pDTA-down-C plasmids were introduced into mouse BAC clones containing AB fragments. pDTA-down-ABC plasmids containing 5'-homologous arm, AB fragments, and 3'-homologous arm were obtained by homologous recombination.

TABLE 6

The PCR reaction system (20 μL)

| 5x Phusion HF Buffer | 4 μL |
|---|---|
| dNTP (10 mM) | 0.4 μL |
| Primer F (10 μM) | 1 μL |
| Primer R (10 μM) | 1 μL |
| DNA template | 5 ng |
| Phusion DNA polymerase (2 U/μL) | 0.2 μL |
| H$_2$O | Add to 20 μL |

TABLE 7

The PCR reaction conditions
PCR Conditions

| Temperature | Time | Cycles |
|---|---|---|
| 98° C. | 30 sec | 1 |
| 98° C. | 10 sec | 35 |
| 58° C. | 25 sec | |
| 72° C. | 30 sec/kb | |

TABLE 7-continued

The PCR reaction conditions
PCR Conditions

| Temperature | Time | Cycles |
|---|---|---|
| 72° C. | 5-10 min | 1 |
| 4° C. | 10 min | 1 |

In step (2), when fragments A1 and A2-1 were ligated, Primer F in Table 6 was SEQ ID NO: 1, Primer R was SEQ ID NO: 4, and template DNA was the recovered PCR amplification product of A1 fragment and A2-1 fragment. When fragments A2-2 and A3 were ligated, Primer F was SEQ ID NO: 5, primer R was SEQ ID NO: 8, and template DNA was the recovered PCR amplification product of A2-2 fragment and A3 fragment. The electroporation process is described in detail below.

Electroporation

The BAC clones were added into LB liquid medium (5 mL) with appropriate antibiotics as shown in the table below. The bacteria were cultured at 30° C. for 12-16 hours at 250 rpm. The next day, the corresponding antibiotics (1:50) as shown in the table below were added into the LB liquid medium, and the bacteria were further cultured at 30° C., 250 rpm for 2-3 hours. When the OD value reached 0.15~0.2, 30 mL of culture medium was collected. 1.2 mL of arabinose (0.4%) was added. After 45-60 min of induction, the culture was kept on ice for 30 min. The culture was then aliquoted into 50 mL centrifuge tubes, centrifuged at 5000 rpm for 10 min at −1° C. The supernatant was discarded. ddH$_2$O (10 mL) was then added, mixed, and the solution was then centrifuged at 5000 rpm for 10 min at −1° C. The supernatant was discarded. After being washed for one more time, the bacteria were kept on ice.

15 μL of plasmids (0.2-0.3 ng/μL) was added added into a 1.5 mL Eppendorf tube, and kept on ice. 85 μL of competent cells were then added, and were carefully mixed with the plasmids. The mixture was then transferred to cuvettes. The setting for the electroporator (BTX, ECM-630) was 1.3 kV, 50 g, and 125Ω. Immediately after electroporation, 800 μL of LB liquid medium was added. After culturing the bacteria at 150 rpm for 1 h at 30° C., the bacteria were plated on petri dishes with appropriate antibiotics as shown in the table below, and were then cultured for 30 hours or more.

TABLE 8

| Steps | Antibiotics for LB medium | Antibiotics for petri dishes |
|---|---|---|
| Step (3) (Human BAC) | Chloramphenicol (Chl) | Carbenicillin (CBC) + Kanamycin (Kan) |
| Step (4) (Mouse BAC) | Chl | Chl + Kan |
| Step (6) (BAC containing AB fragments) | Chl + Kan | CBC + Kan | pBs-Neo Plasmids

Figure 4:
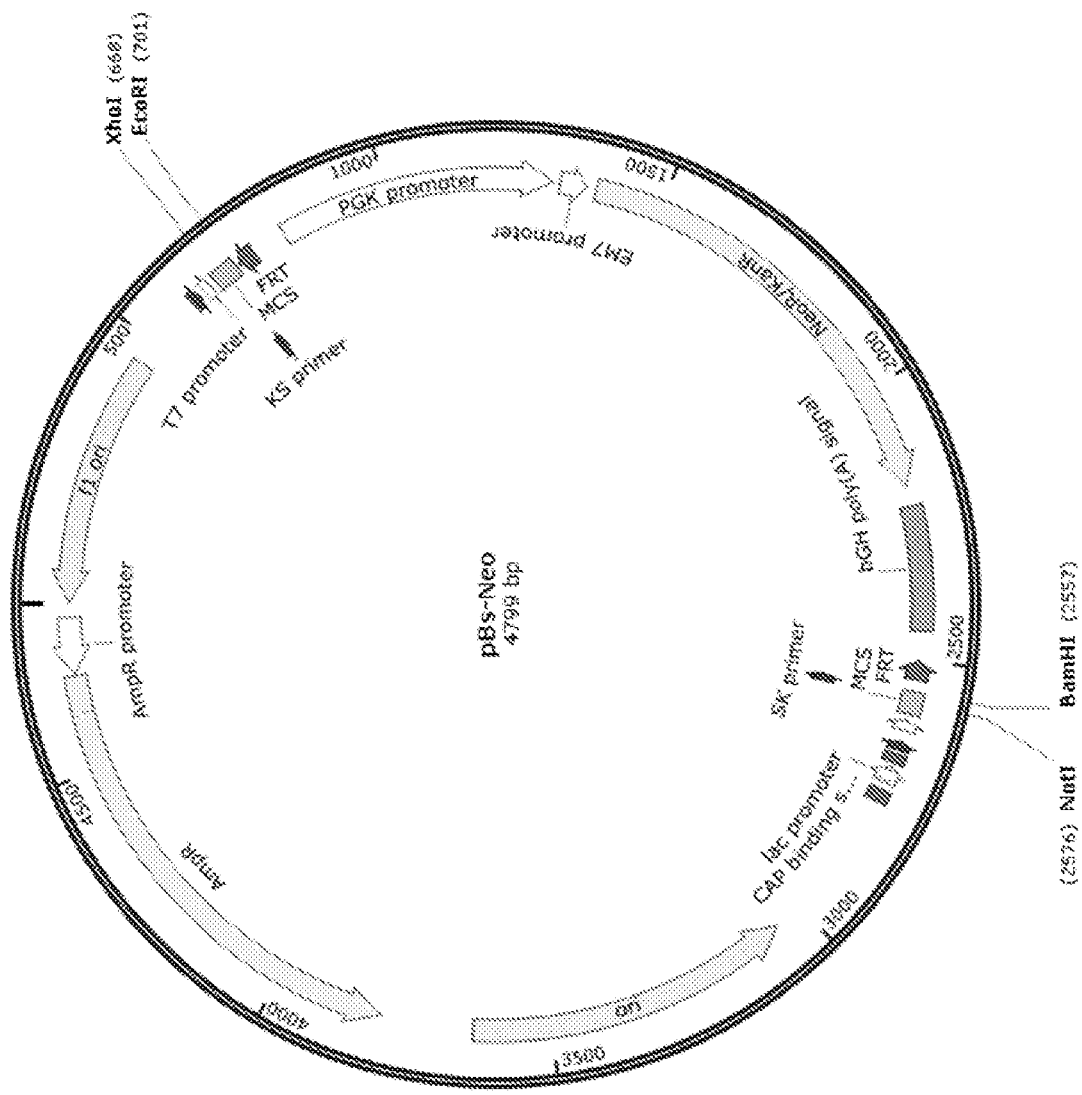
FIG. 4 is a schematic diagram showing the structure of pBs-Neo plasmid.

FIG. 4 shows pBs-Neo vector map. The plasmid backbone was obtained from Agilent (Cat. No. 212205). DNA fragment containing frt and neo gene (neomycin-resistance) (SEQ ID NO: 26) was synthesized and ligated to the vector backbone by restriction enzyme digestion (EcoRI/BamHI). The sequences of the plasmids were further verified by sequencing.

Example 3. Verification of pDTA-Down-ABC Vector

Figure 5:
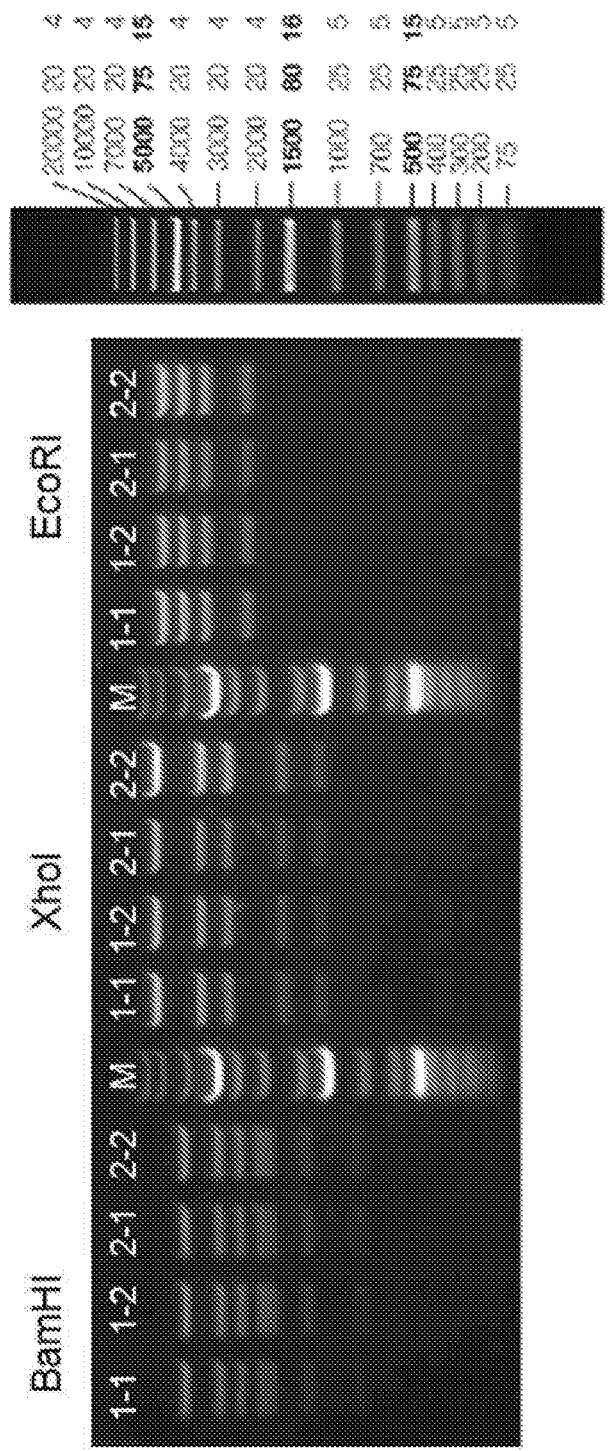
FIG. 5 shows the result of restriction enzymes digestion of the targeting plasmid pDTA-down-ABC.

Four pDTA-down-ABC clones were randomly selected and tested by three sets of restriction enzymes. Among them, BamHI should generate 6817p+4629 bp+3682 bp+2952 bp+2618 bp+1786 bp+1035 bp fragments; XhoI should generate 9976 bp+5502 bp+4037 bp+2210 bp+1477 bp+317 bp fragments; EcoRI should generate 8679 bp+6589 bp+5033 bp+3218 bp fragments. The results were in line with the expectations (FIG. 5). The sequences of Plasmids 1-1 and 2-1 were further verified by sequencing.

Example 4. C57BL/6 Mouse Embryonic Stem Cell Culture, Transfection and Clone Screening Embryonic Stem Cell Culture C57BL/6 embryonic stem cells were cultured in petri dishes with feeder cells, and were incubated in an incubator at 37° C., 5% $CO_2$ with saturated humidity. The composition of the culture medium is shown in the table below.

TABLE 9

| Medium composition | Volume |
| --- | --- |
| Knockout DMEM | 500 ml |
| FBS | 90 ml |
| MEM NEAA | 6 ml |
| L-Glutamine | 6 ml |
| ESGRO LiF | 60 μL |
| β-Mercaptoethanol | 600 μL |

Transfection by Electroporation

C57BL/6 embryonic stem cells were confirmed to be in good condition prior to electroporation.

The petri dishes with embryonic stem cells were retrieved from the incubator. The medium was removed. 5 ml PBS was added, and the petri dishes were washed twice. 1.5 ml 0.25% trypsin was added to each petri dish, and was incubated in 37° C. incubator for 3 minutes. 3.5 ml of ES medium per dish was then added to stop the digestion. The cells were then transferred to 50 ml centrifuge tubes to count cells. $1.2 \times 10^7$ cells were added into a new 50 ml centrifuge tube. The cells were centrifuged at 1200 rpm for 5 min at 4° C. The supernatant was then removed. An appropriate amount of RPMI medium (without phenol red) was added. The cells were then suspended and gently mixed with pDTA-down-ABC vector. The mixture was kept in ice water bath for 5 minutes, and was then transferred to cuvettes. The setting for electroporation was 280V, 500 g, and 10 ms. The cuvettes were kept in ice water bath for 5 min, and then kept at room temperature for 5 minutes. The cells were then transferred into a 50 ml centrifuge tube containing 40 ml of embryonic stem cell culture medium. The mixture was then divided, and added into four 100 mm petri dishes containing MMC feeder cells. These cells were then incubated at 37° C. in a 5% $CO_2$ incubator. After incubating these cells for 20 hours, the medium was replaced by G418 medium.

Clone Selection

After 20 hours of culturing, the medium was replaced by G418 medium for positive selection and negative selection. The cell colonies were then picked and transferred into 96-well plates. After the cells grew for a sufficient period of time, the cells were then transferred to 48-well, 6-well and 60-mm plates, and the DNA of the cells was collected. PCR and Southern blotting were used to select the positive clones.

Example 5. Microinjection and Embryo Transfer

The positive embryonic stem cells in Example 4 were injected into BALB/c mouse blastocysts. The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected blastocysts were then transferred to a culture medium and were cultured for a short time period, and then was transplanted into the oviduct of the recipient mouse to produce the chimeric mice (F0 generation). The chimeric mouse was then mated with Flp recombinase transgenic mice, generating F1 generation (black or gray color). Black mice were selected. Genomic DNA from the tails of black mice were collected and tested by PCR to determine whether the mouse is a humanized CD27 gene heterozygote. The primers for PCR are shown in the table below.

TABLE 10

| Primer | Sequence | | Product length |
| --- | --- | --- | --- |
| WT-F | 5'-AAGCTTCCAGGTCAGGGAGGAATC-3' | (SEQ ID NO: 27) | WT: 366 bp |
| WT-R | 5'-GTGTCTTACTTGGCCCGTGGTTTC-3' | (SEQ ID NO: 28) | |
| Mut-F | 5'-TGGCGGGTGGGATAGAATAAGGTG-3' | (SEQ ID NO: 29) | Mut: 248 bp |
| WT-R | 5'-GTGTCTTACTTGGCCCGTGGTTTC-3' | (SEQ ID NO: 28) | |
| Frt-F | 5'-CCTTACGGCCCAGGGACTCTAGTAA-3' | (SEQ ID NO: 31) | Mut: 345 bp |
| Frt-R | 5'-CCCTTGTCACACCACTTAACCCCTT-3' | (SEQ ID NO: 32) | WT: 257 bp |
| Flp-F2 | 5'-GACAAGCGTTAGTAGGCACATATAC-3' | (SEQ ID NO: 33) | Mut: 325 bp |
| Flp-R2 | 5'-GCTCCAATTTCCCACAACATTAGT-3' | (SEQ ID NO: 34) | |

The PCR conditions were

95° C. 5 min;

95° C. 30 sec, 62° C. 30 sec, 72° C. 25 sec, 35 cycles in total;

72° C. 10 min;

4° C. 10 min.

PCR was performed to determine whether the recombinant fragment was inserted at the correct genomic site. The primer pair WT-F and WT-R was used to amplify exon 5 of CD27 gene of wild-type mice. The primer pair Mut-F and WT-R was used to amplify the humanized exon 5 fragment.

The primer pair Frt-F and Frt-R was used to amplify neo fragments to determine whether the neo gene was removed. The primer pair Flp-F2 and Flp-R2 was used to confirm the presence of Flp fragments.

Figure 6:
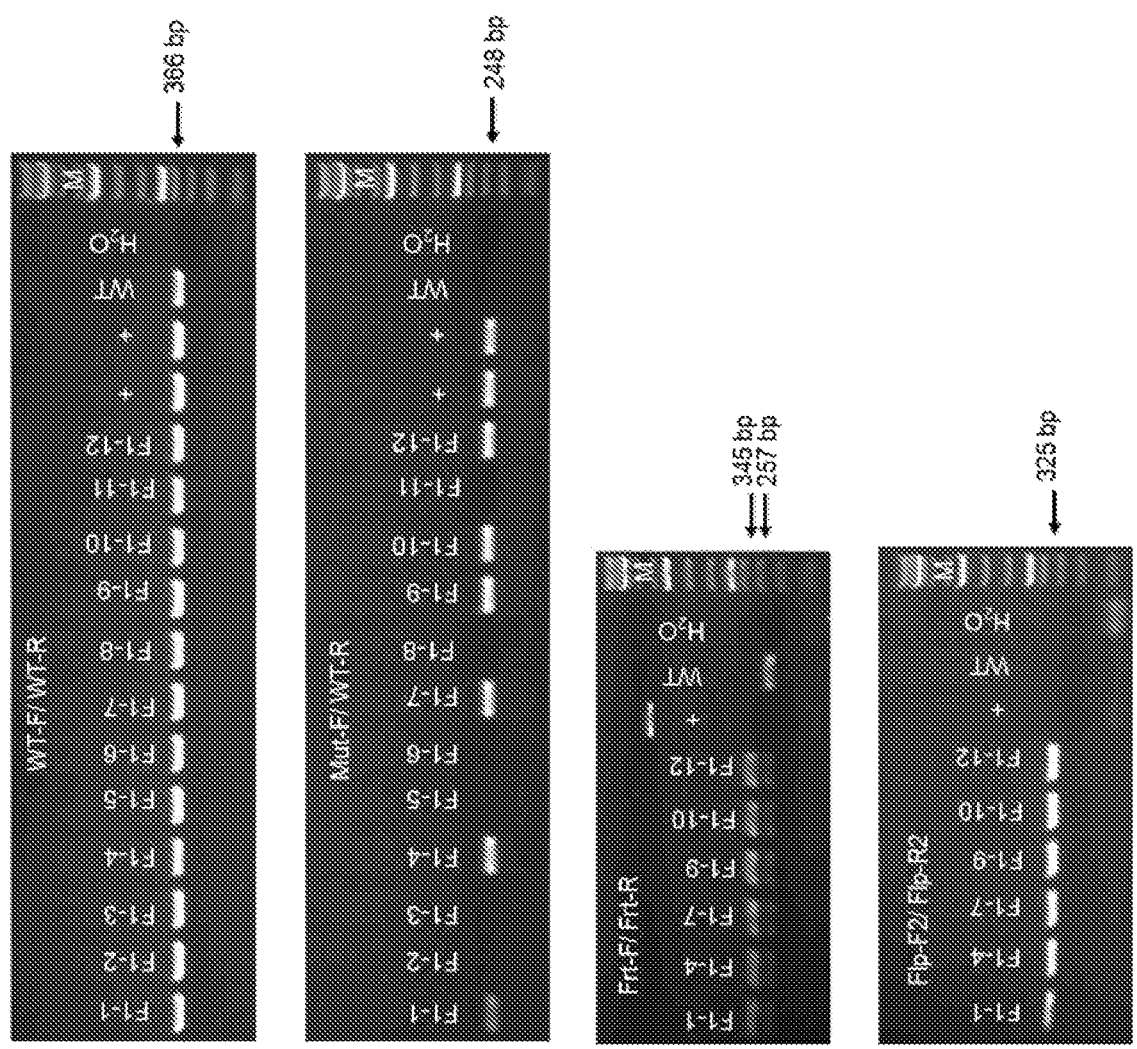
FIG. 6 shows the PCR results using samples collected from the tails of F1 generation mice. WT stands for wild-type. Based on the result, F1-1, F1-4, F1-7, F1-9, F1-10, and F1-12 are heterozygous for humanized CD27.

Six out of 11 F1 mice were identified as positive mic. The PCR results of 6 mice were shown in FIG. 6. As shown in the figure, F1-1, F1-4, F1-7, F1-9, F1-10 and F1-12 were positive heterozygous mice.

Example 6. Verification of Genetically Modified Humanized Mouse Model

A humanized heterozygous F1 generation mouse was selected. Two wildtype C57BL/6 mice were used as the control.

7.5 μg of mouse anti-CD3 antibody was injected intraperitoneally to the mice. The spleens were collected 24 hours after the injection, and the spleen samples were grinded. The ground samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed once with PBS.

Figures 7A, 7B, 7C, 7D, 7E, 7F:
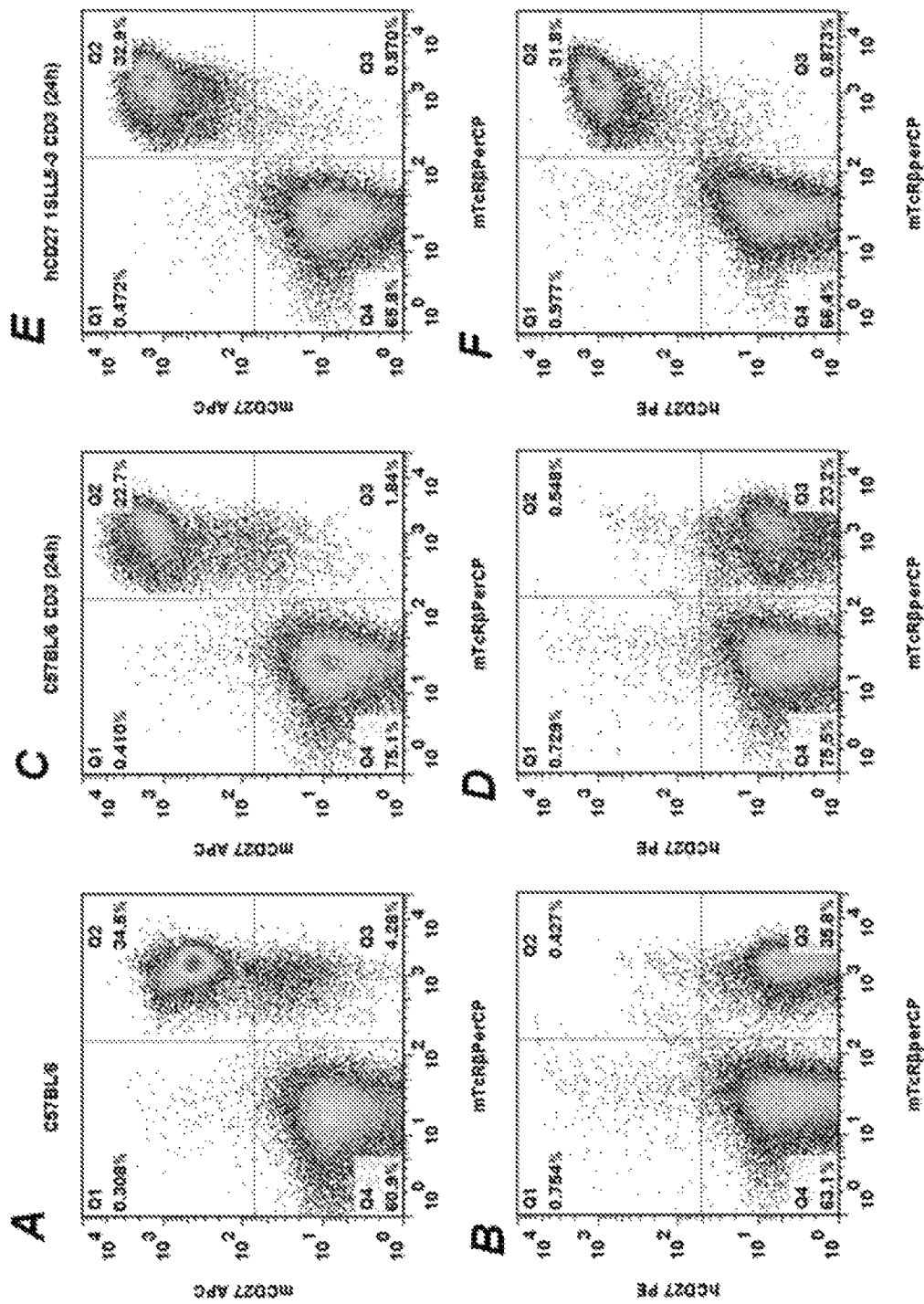
FIGS. 7A-7F are flow cytometry results for C57BL/6 mice and heterozygous humanized CD27 mice. Flow cytometry was performed with 1) an antibody against mouse CD27 (anti-mCD27 (APC)) and an antibody against mouse TcRβ (anti-mTcRβ); and 2) an antibody against human CD27 (anti-hCD27 (PE)), and an antibody against mouse TcRβ (anti-mTcRβ). Compared to the control groups (FIG. 7A and FIG. 7B), no spleen cells stained with anti-hCD27 (PE) were observed in the spleen of C57BL/6 mice (FIG. 7D); while spleen cells stained with anti-hCD27 (PE) were observed in heterozygous mice with humanized CD27 (FIG. 7F).

FACS: Anti-mouse CD27 antibodies (mCD27 APC) and anti-mTCRβ antibody (TCRβ PerCP), or anti-human CD27 antibodies (hCD27 PE) and anti-mTCRβ antibody (TCRβ PerCP) were used to stain the cells. The cells were washed once with PBS and analyzed by flow cytometry. The results of flow cytometry (FIGS. 7A-7F) showed that the spleen of humanized heterozygous mouse (FIGS. 7E and 7F) had cells expressing mouse CD27 protein and humanized CD27 proteins, while the spleen of the C57BL/6 control mice did not have detectable cells expressing humanized CD27 proteins (FIG. 7D). The foregoing results indicate that the genetically modified CD27 humanized mice were able to express humanized CD27 proteins, and humanized CD27 protein cannot be detected in C57BL/6 mice.

RT-PCR detection: RNA was extracted from the spleen cells, and cDNA were then obtained by reverse transcription using a reverse transcription kit.

```
Primers for mCD27 RT-PCR:
mCD27 RT-PCR F2:
                                         (SEQ ID NO: 35)
5'-CTGCAGGCATTGTAACTCTGGT-3'
and mCD27 RT-PCR R2:
                                         (SEQ ID NO: 36)
5'-CATGAGGTAAGTGGGTGGGTG-3' were
used to amplify mouse CD27 fragment of 194 bp.

Primers for hCD27 RT-PCR:
hCD27 RT-PCR F2:
                                         (SEQ ID NO: 37)
5'-CTACTGGGCTCAGGGAAAGCTG-3'
and hCD27 RT-PCR R2:
                                         (SEQ ID NO: 38)
5'-ATTGGCAGTGATGGTGCAGTT-3'
``` were used to amplify human CD27 fragment of 211 bp.

PCR reaction system was 20 μL, reaction conditions: 95° C., 5 min; (95° C., 30 sec; 60° C., 30 sec; 72° C., 30 sec, 35 cycles); 72° C., 10 min; and then keeping it at 4° C. GAPDH was used as an internal reference.

Figure 8:
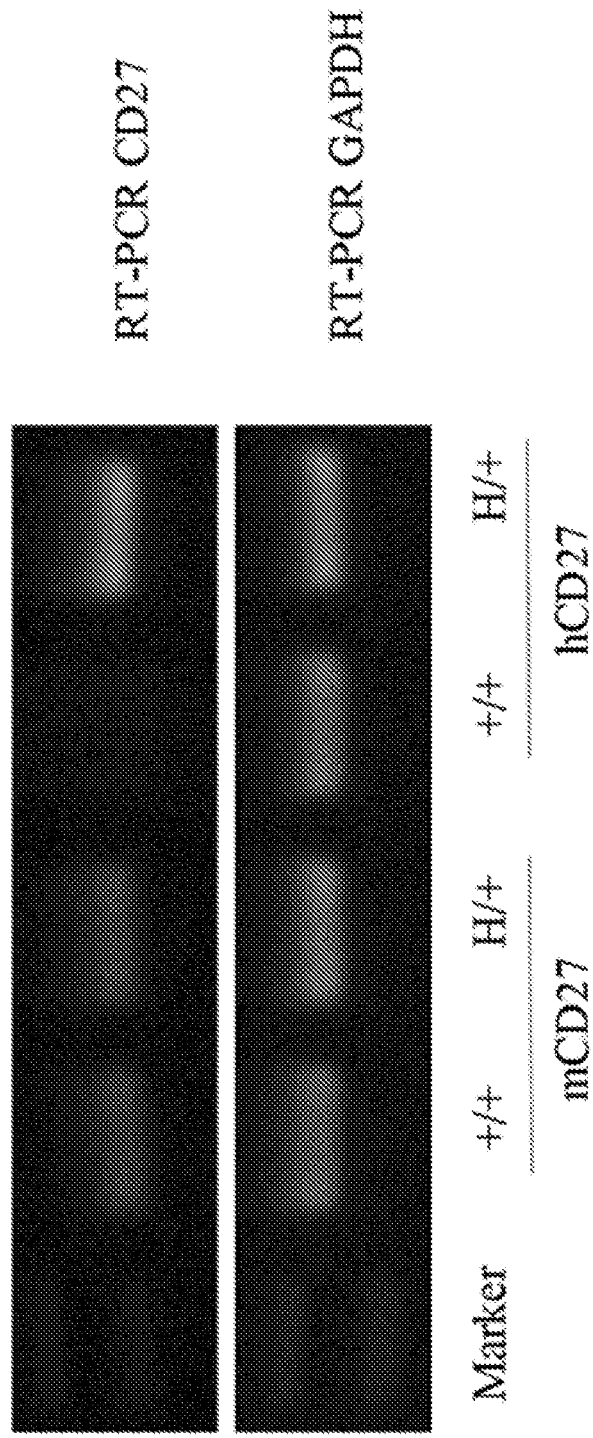
FIG. 8 shows results from RT-PCR. +/+ indicates wild-type C57BL/6 mice; H/+ indicates F1 generation mice that are heterozygous for humanized CD27; and GAPDH was used as a control.

The results are shown in FIG. 8. The mRNA expression of mouse CD27 was detected in the activated cells of wildtype C57BL/6 mice and F1 generation heterozygous mouse; while the mRNA expression of humanized CD27 was only detected in the activated cells of the F1 generation heterozygous mouse.

Figures 9A, 9B, 9C, 9D, 9E, 9F:
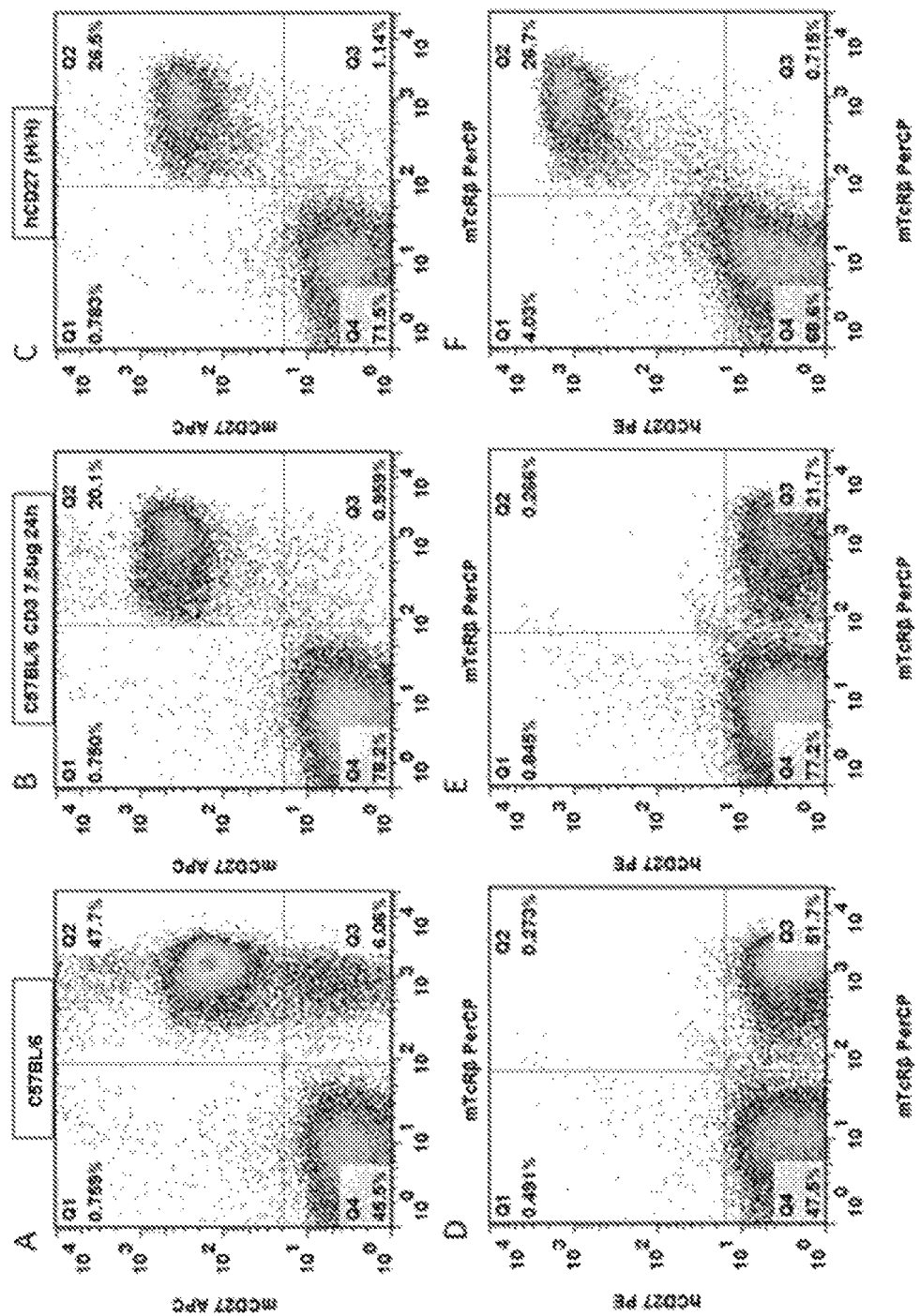
FIGS. 9A-9F are results of flow cytometry analysis. C57BL/6 wildtype mice were used in FIGS. 9A, 9B, 9D, and 9E. Mice in FIG. 9B and FIG. 9E were stimulated with anti-mCD3 antibody (mice in FIG. 9A and FIG. 9D were not stimulated with anti-mCD3 antibody). Humanized CD27 homozygous mice were used in FIG. 9C and FIG. 9F, and were stimulated with anti-mCD3 antibody. Flow cytometry was performed with: 1) antibody against mouse CD27 (anti-mCD27 (APC)) and antibody against mouse TcRβ (anti-mTcRβ) (FIGS. 9A-9C); and 2) antibody against human CD27 (anti-hCD27 (PE)), and antibody against mouse TcRβ (anti-mTcRβ) (FIGS. 9D-9F).
Figure 10:
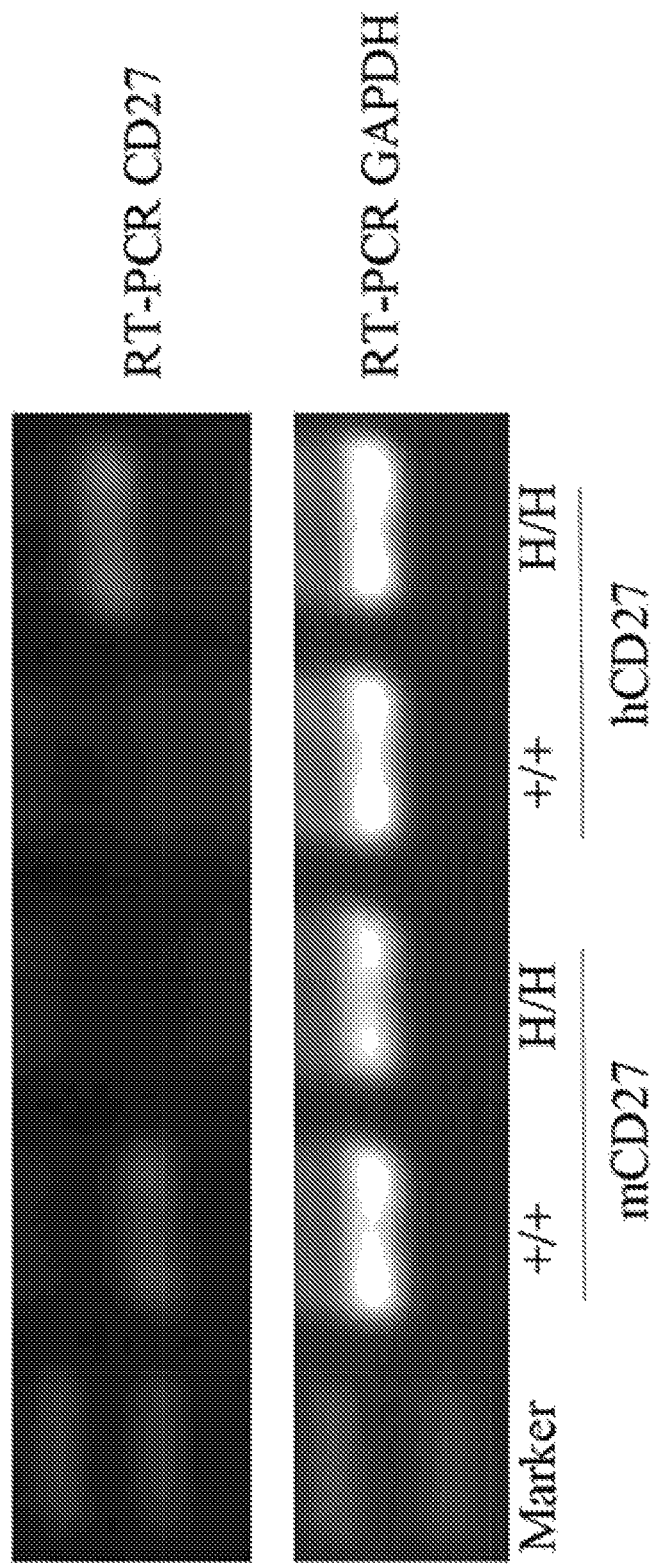
FIG. 10 shows results from RT-PCR. +/+ indicates wildtype C57BL/6 mice; H/H indicates homozygous humanized CD27 mice. GAPDH was used as a control.

The F1 heterozygous mice were further mated to each other to obtain genetically recombinant positive F2 generation homozygous mice. The homozygous mice were tested by FACS and RT-PCR by the methods as described above. FACS results (FIGS. 9A-9F) show that cells expressing humanized CD27 protein can be detected in humanized CD27 homozygous mice (FIG. 9F), and mouse CD27 can be detected in C57BL/6 with or without anti-CD3 antibody stimulation. The signal in FIG. 9C was due to the cross-reactivity of anti-mCD27 antibody with humanized CD27. RT-PCR results were shown in FIG. 10. The mRNA expression of mouse CD27 was only detected in the activated cells of wildtype C57BL/6 mice and the mRNA expression of humanized CD27 was only detected in the activated cells of the humanized F2 generation homozygous mice.

The results above show that the CD27 humanized mouse can express the humanized CD27 protein and the humanized CD27 protein can be recognized by the anti-hCD27 antibody.

Example 7. Mice with Humanized CD27 and Humanized PD-1

Mice containing the humanized CD27 gene (e.g., B-hCD27 animal model with humanized CD27 prepared using the methods as described in the present disclosure) can also be used to prepare an animal model with double-humanized or multi-humanized genes. For example, in Example 4, the embryonic stem cell used in the microinjection and embryo transfer process can be selected from the embryos of other genetically modified mice, so as to obtain double- or multiple-gene modified mouse models.

In addition, the B-hCD27 animal model homozygote or heterozygote can be mated with other genetically modified homozygous or heterozygous animal models, and the progeny is then screened; according to the Mendelian law, there is a chance to obtain the double-gene or multiple-gene modified heterozygous animal models, and then the obtained heterozygous can be mated with each other to finally obtain the double-gene or multiple-gene modified homozygotes.

In the case of the generating double humanized CD27/PD-1 mouse, since the mouse CD27 gene and PD-1 gene are located on different chromosomes, the double humanized CD27/PD-1 mouse was obtained by crossing the B-hCD27 mouse with B-hPD-1 mouse (mice with humanized PD-1 gene) through in vitro fertilization.

Figures 11A, 11B, 11C, 11D:
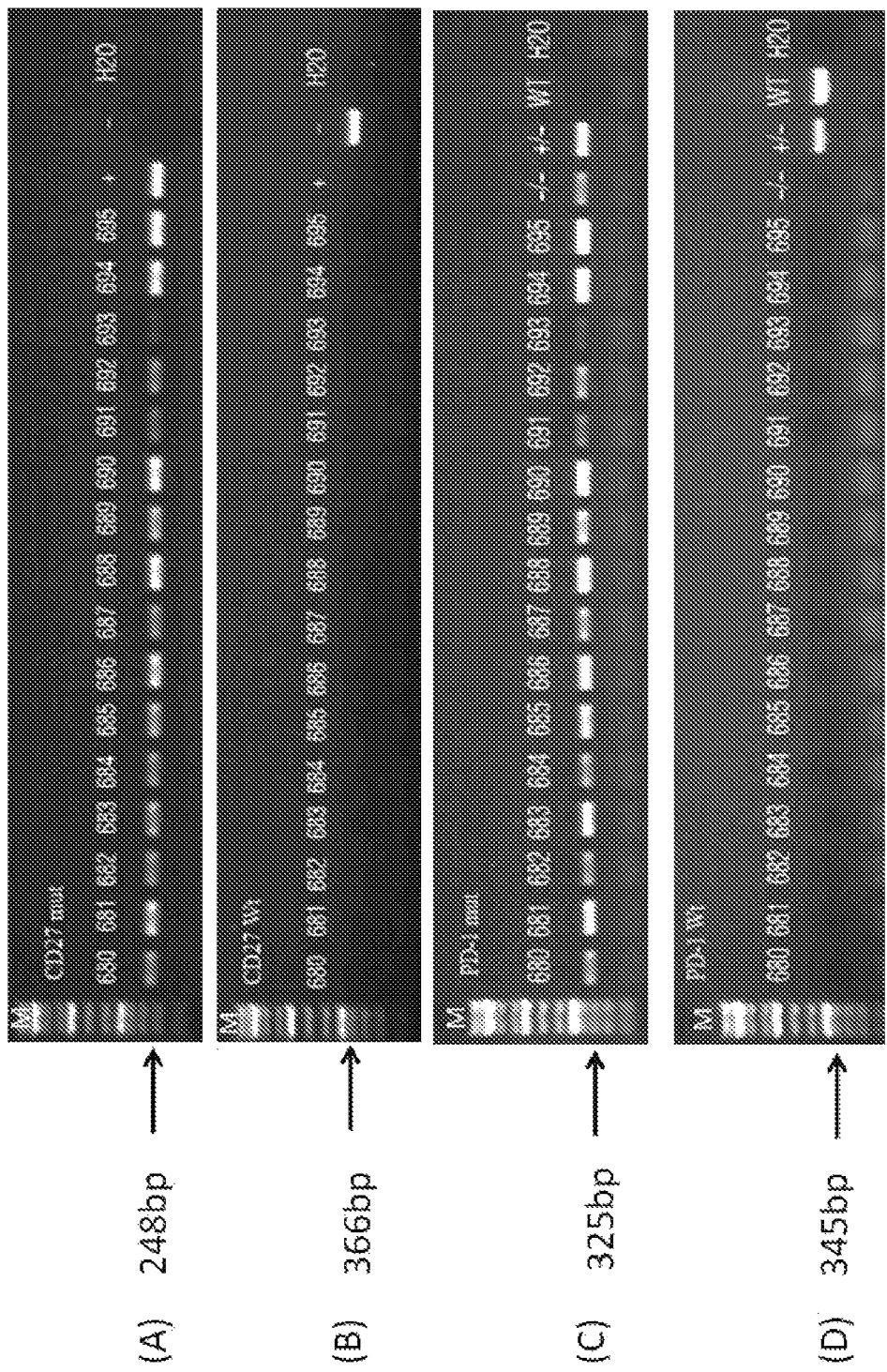
FIGS. 11A-11D are results from PCR.
Figures 12A, 12B, 12C, 12D, 12E, 12F:
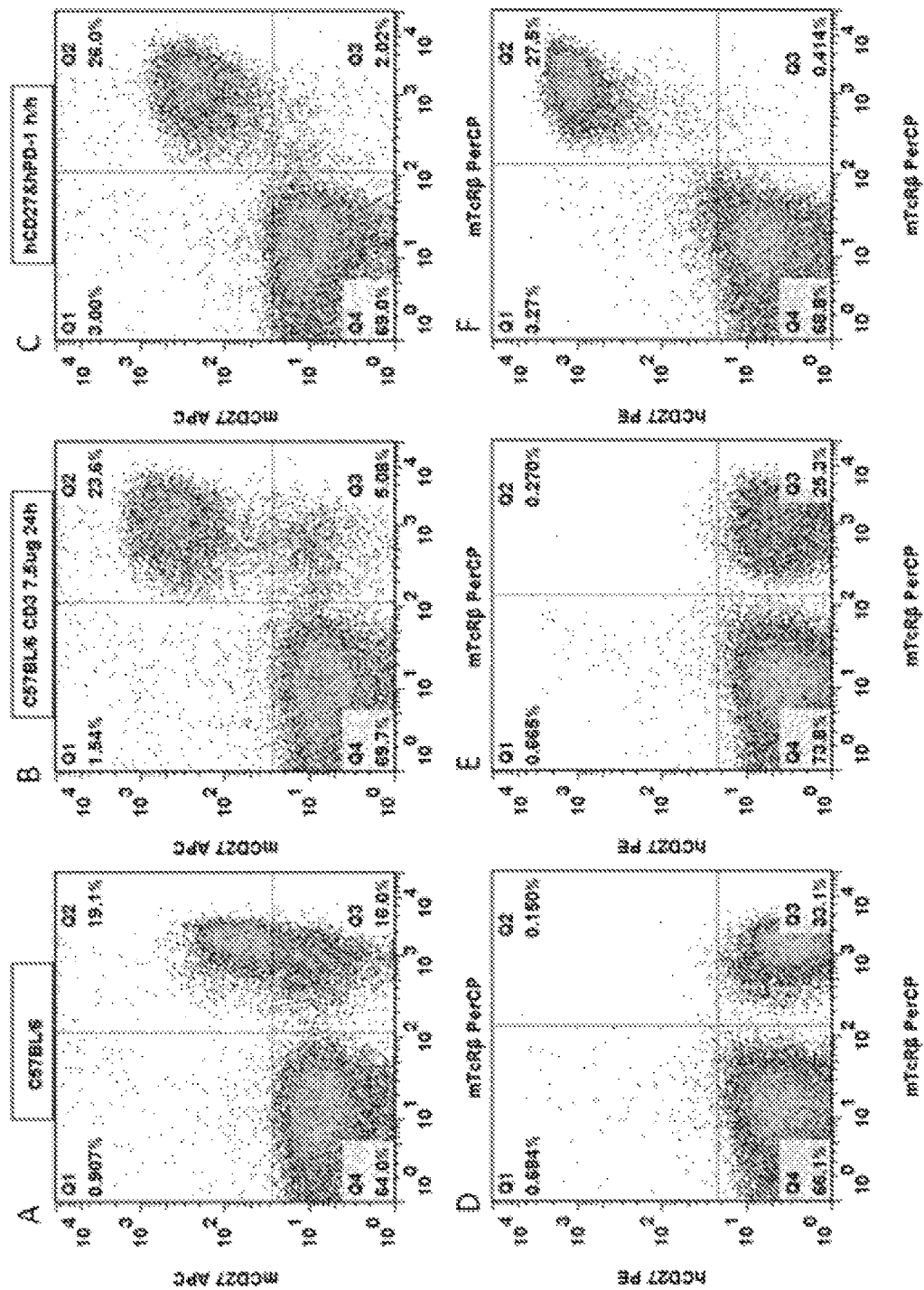
FIGS. 12A-12F are results of flow cytometry analysis.
Figures 13A, 13B, 13C, 13D, 13E, 13F:
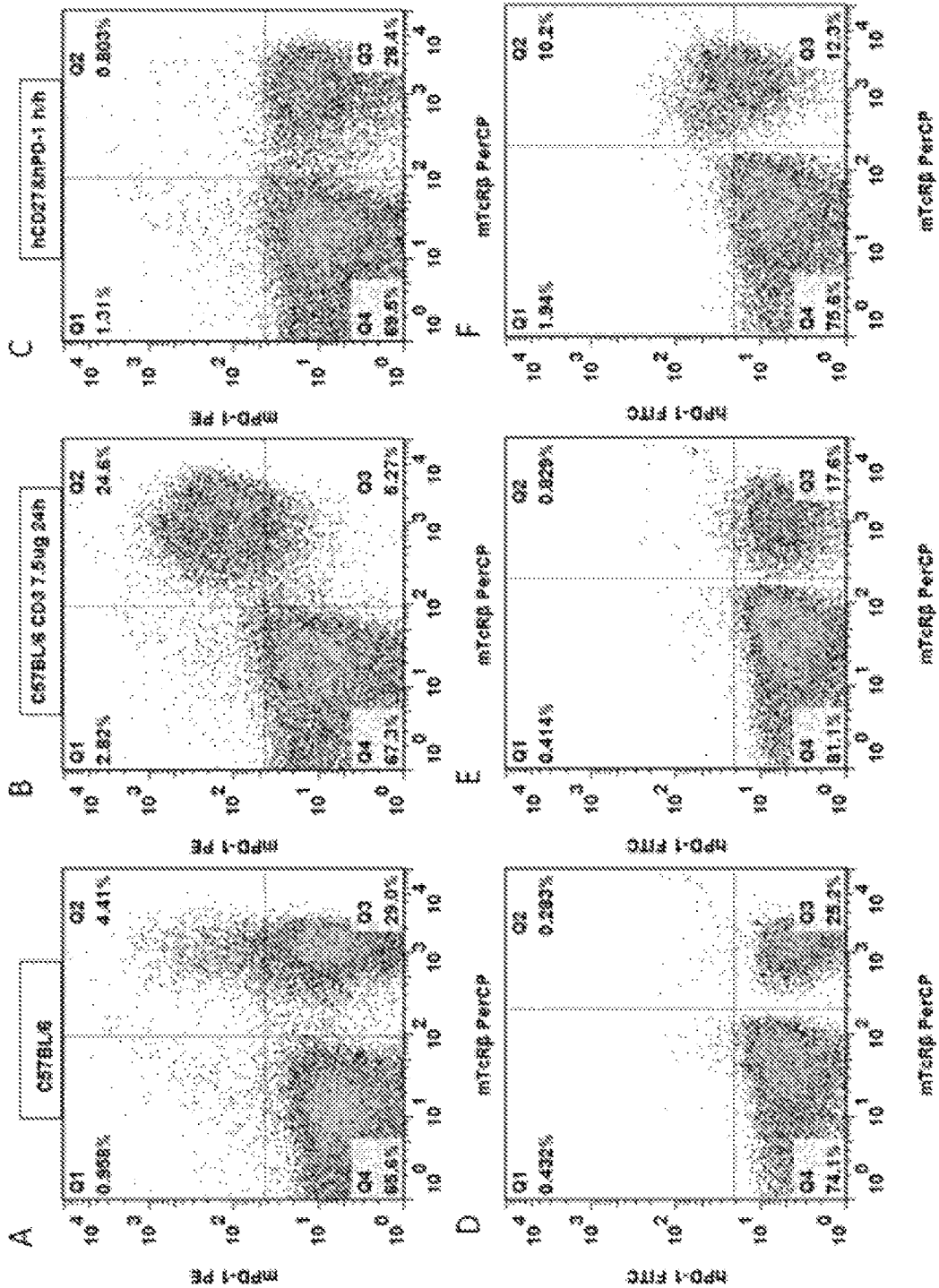
FIGS. 13A-13F are results of flow cytometry analysis.

PCR analysis was performed on the mouse tail genomic DNA of double humanized CD27/PD-1 mice using four pairs of primers. The specific sequences and product lengths are shown in the table below. The reaction system and reaction conditions are shown in Table 12 and Table 13. The results for a number of humanized CD27/PD-1 mice are shown in FIGS. 11A-11D, wherein FIGS. 11A and 11B show that the mice numbered 680-695 were homozygous for humanized CD27. FIGS. 11C and 11D show that the mice numbered 680-695 were homozygous for humanized PD-1. The combined results show that the mice numbered 680-695 were homozygous for both humanized CD27 and humanized PD-1. They are labeled as $CD27^{H/H}/PD-1^{H/H}$.

TABLE 11

Primer sequences

| Primer | Sequence | Product length |
|---|---|---|
| CD27 WT | F:5'-aagcttccaggtcagggaggaatc-3' (SEQ ID NO: 27)<br>R:5'-gtgtcttacttggcccgtggtttc-3' (SEQ ID NO: 28) | WT: 366 bp |
| CD27 MUT | F:5'-tggcgggtgggatagaataaggtg-3' (SEQ ID NO: 29)<br>R:5'-gtgtcttacttggcccgtggtttc-3' (SEQ ID NO: 28) | Mut: 248 bp |
| PD-1 MUT | F:5'-cttccacatgagcgtggtcagggcc-3' (SEQ ID NO: 30)<br>R:5'-ccaagggactattttagatgggcag-3' (SEQ ID NO: 39) | Mut: 325 bp |
| PD-1 WT | F:5'-gaagctacaagctcctaggtaggggg-3' (SEQ ID NO: 40)<br>R:5'-acgggttggctcaaaccattaca-3' (SEQ ID NO: 41) | WT: 345 bp |

TABLE 12

PCT reaction

| | |
|---|---|
| 2x Master Mix | 10 μL |
| Upstream primer (10 μM) | 0.5 μL |
| Downstream primer (10 μM) | 0.5 μL |
| Mouse tail genomic DNA (100-200 ng/20 ml) | 2 μL |
| ddH$_2$O | Add to 20 μL |

TABLE 13

PCR amplification reaction condition

| Temperature | Time | Cycles |
|---|---|---|
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

The expression of the double humanized CD27/PD-1 mice was further examined. A double humanized CD27/PD-1 homozygote (9 weeks old) was selected for the study. Two wildtype C57BL/6 mice were selected as controls. Mice were injected with 7.5 μg of mouse anti-CD3 antibody intraperitoneally. After 24 hours, the mice were euthanized, and then the spleens of the mice were collected. The obtained spleen cell samples were then analyzed by FACS and RT-PCR.

FACS: Expression of CD27 proteins in double humanized CD27/PD-1 mice was analyzed using the same methods as described above. The samples were stained with either 1) mouse anti-mCD27 antibody (mCD27 APC) and anti-mTcRβ antibody (mTcRβ PerCP); or 2) anti-human CD27 antibody (hCD27 PE) and anti-mTcRβ antibody (mTcRβ PerCP) for determining the expression of CD27. The samples were also stained with either 1) mouse anti-mPD-1 antibody (mPD-1 PE) and anti-mTcRβ antibody (mTcRβ PerCP); or 2) anti-hPD-1 antibody (hPD-1 FITC) and anti-mTcRβ antibody (mTcRβ PerCP) for determining the expression of PD-1. The stained samples were washed in PBS and analyzed by flow cytometry. Results are shown in FIGS. 12A-12F, and FIGS. 13A-13F.

Cells expressing humanized CD27 and humanized PD-1 proteins were detected in the spleens of double humanized CD27/PD-1 homozygotes. Humanized CD27 and humanized PD-1 were not detected in the spleens of C57BL/6 mice either with anti-CD3 antibody stimulation or without anti-CD3 antibody stimulation.

RT-PCR detection: Total RNA was extracted from the spleen cells of wildtype C57BL/6 mice and double humanized CD27/PD-1 homozygotes. cDNA was then obtained by reverse transcription using a reverse transcription kit.

mCD27 RT-PCR F2 (SEQ ID NO: 35) and mCD27 RT-PCR R2 (SEQ ID NO: 36) were used to amplify a mouse CD27 fragment of 194 bp.

hCD27 RT-PCR F2 (SEQ ID NO: 37) and hCD27 RT-PCR R2 (SEQ ID NO: 38) were used amplify a humanized CD27 fragment of 211 bp. mPD-1 RT-PCR primer F3: 5'-CCTGGCTCACAGTGTCAGAG-3' (SEQ ID NO: 42), and mPD-1 RT-PCR R3: 5'-CAGGGCTCTCCTCGAT-TTTT-3' (SEQ ID NO: 43) were used to amplify a mouse Pd-1 fragment of approximately 297 bp.

hPD-1 RT-PCR F3: 5'-CCCTGCTCGTGGTGACCGAA-3' (SEQ ID NO: 44), and hPD-1 RT-PCR R3: 5'-GCAGGCTCTCTTTGATCTGC-3' (SEQ ID NO: 45) were used to amplify a human PD-1 fragment of approximately 297 bp.

PCR reaction system was 20 reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 14:
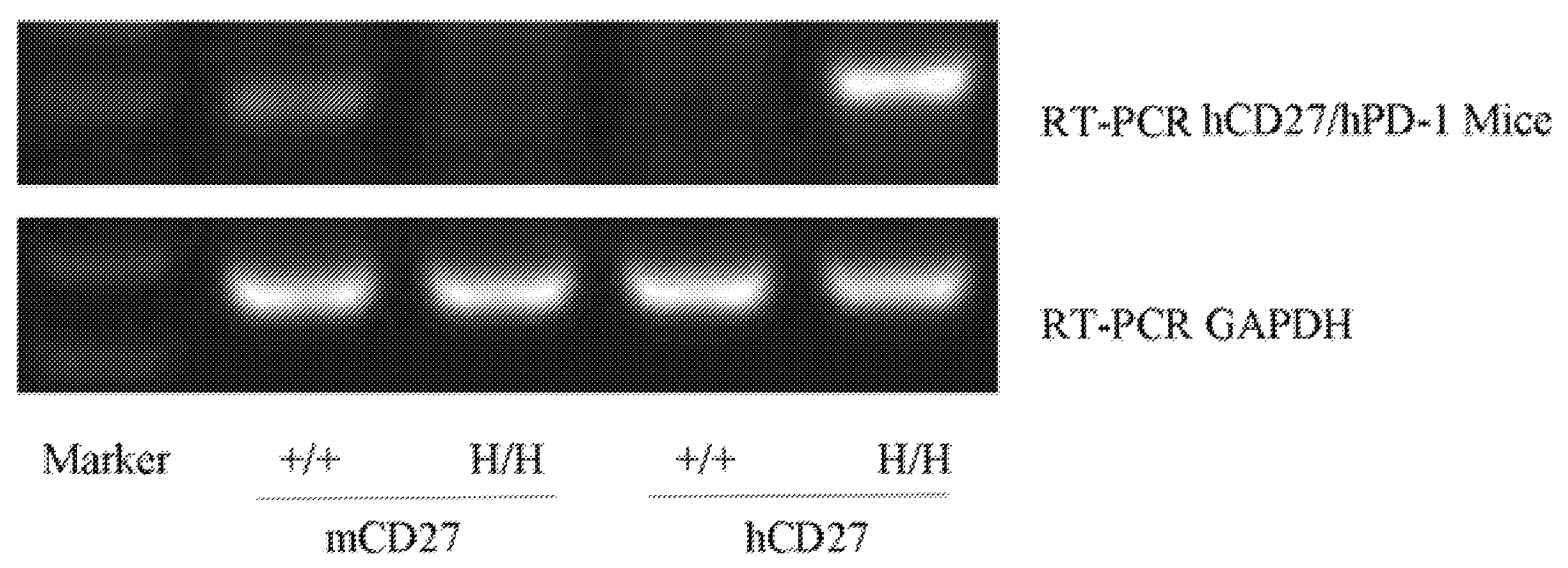
Figure 15:
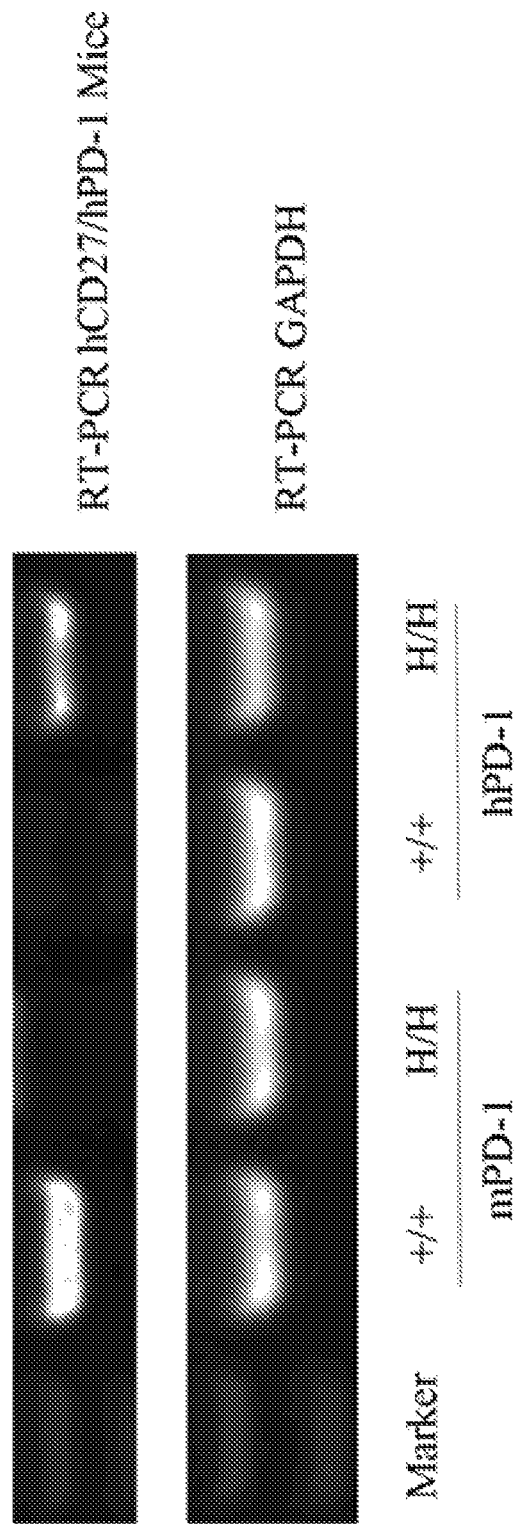
FIG. 15 shows results from RT-PCR. +/+ indicates wildtype C57BL/6 mice; H/H indicates mice that are homozygous for both humanized CD27 and humanized PD-1; and GAPDH was used as a control.

The results were shown in FIG. 14 and FIG. 15. The mRNA of mouse CD27 and mouse PD-1 were detected in the activated cells of wildtype C57BL/6 mice; while the mRNA of humanized CD27 and humanized PD-1 were detected in the activated cells of double humanized CD27/PD-1 homozygotes (CD27"/PD-1").

Example 8. Mice with Humanized CD27 and Humanized PD-L1

As another example, double humanized CD27/PD-L1 mice were generated. Since the mouse CD27 gene and PD-L1 gene are located on different chromosomes, the double humanized CD27/PD-L1 mice were obtained by crossing humanized CD27 mice with humanized PD-L1 mice (e.g. B-hPD-L1, mice with humanized PD-L1 gene). The progeny were screened and further mated to eventually obtain double humanized CD27/PD-L1 mice.

Figures 16A, 16B, 16C, 16D:
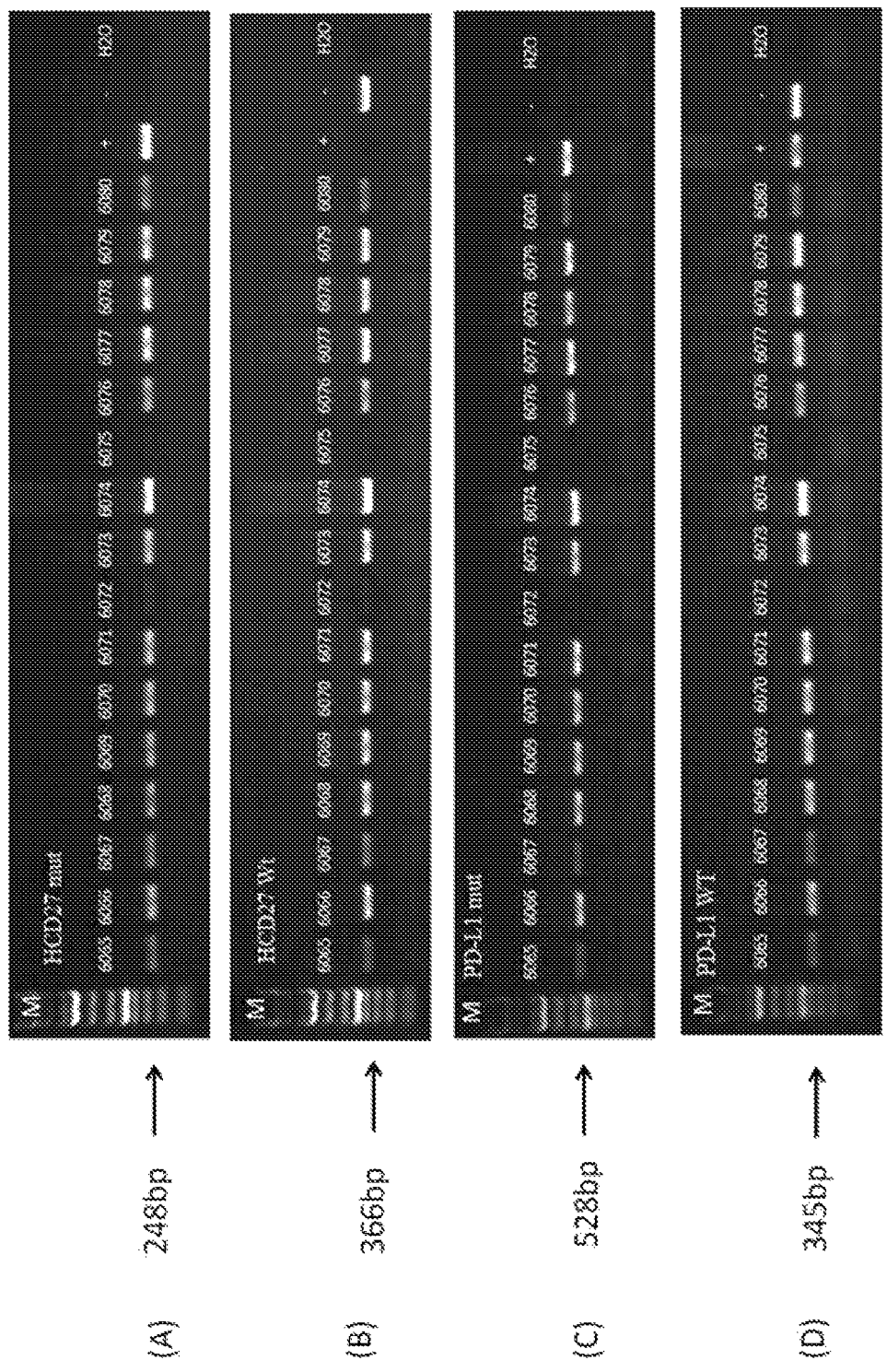
FIGS. 16A-16D show the result of PCR.

PCR analysis was performed on the mouse tail genomic DNA of double humanized CD27/PD-L1 mice using four pairs of primers. The specific sequences and product lengths are shown in Table 14. The reaction system and reaction conditions are shown in Table 12 and Table 13. The results for a number of humanized CD27/PD-L1 mice are shown in FIGS. 16A-16D, wherein FIGS. 16A and 16B show that the mice numbered 6065-6080 were heterozygous for humanized CD27. FIGS. 16C and 16D show that the mice numbered 6065-6080 were heterozygous for humanized PD-L1. The combined results show that the mice numbered 6065-6080 were all heterozygous for both humanized CD27 and humanized PD-L1 (CD27$^{H/+}$/PD-L1$^{H/+}$).

TABLE 14

Primer sequences

| Primer | Sequence | | Product length |
|---|---|---|---|
| CD27 WT | F:5'-aagcttccaggtcagggaggaatc-3' | (SEQ ID NO: 27) | WT: 366 bp |
| | R:5'-gtgtcttacttggcccgtggtttc-3' | (SEQ ID NO: 28) | |
| CD27 MUT | F:5'-tggcgggtgggatagaataaggtg-3' | (SEQ ID NO: 29) | Mut: 248 bp |
| | R:5'-gtgtcttacttggcccgtggtttc-3' | (SEQ ID NO: 28) | |
| PD-L1 MUT | F:5'-ccagggaggtggcccactgataata-3' | (SEQ ID NO: 46) | Mut: 528 bp |
| | R:5'-cacccctgcatcctgcaatttcaca-3' | (SEQ ID NO: 47) | |
| PD-L1 WT | F:5'-ccagggaggtggcccactgataata-3' | (SEQ ID NO: 46) | WT: 345 bp |
| | R:5'-actaacgcaagcaggtccagctccc-3' | (SEQ ID NO: 48) | |

Example 9. Pharmacological Validation of B-hCD27 Humanized Animal Model with Mouse Colon Cancer Cell MC38

B-hCD27 homozygous mice (4-6 weeks) were subcutaneously injected with mouse colon cancer cell MC38, and when the tumor volume grew to about 100 mm$^3$, the mice were divided to a control group and treatment groups based on tumor size (n=5/group). The treatment groups were randomly selected for being treated by three different anti-human CD27 antibodies (AB-1, AB-2, AB-3) (10 mg/kg); the control group was injected with an equal volume of blank solvent. The frequency of administration was twice a week (6 times of administrations in total). The tumor volume and the body weight were measured twice a week. Euthanasia was performed when the tumor reached 3000 mm$^3$.

Figure 19:
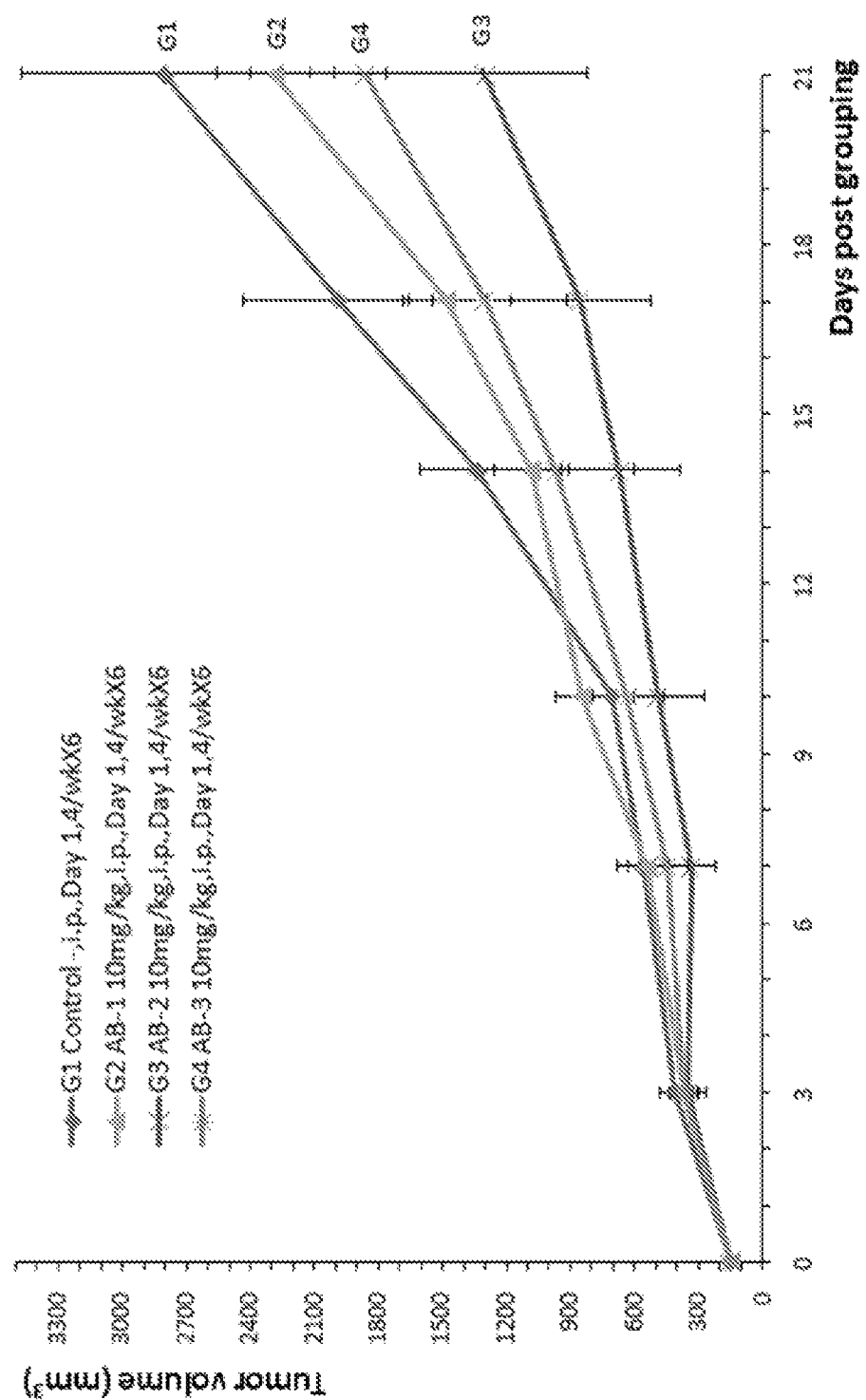
FIG. 19. Mouse colon cancer cells MC38 were injected into humanized CD27 homozygous mice. Antitumor efficacy studies were performed with three antibodies against human CD27 (AB-1, AB-2, and AB-3). The average volumes of tumors in the G1 control group and the G2-G4 treatment groups are shown in this figure.

Table 15 shows results for this experiment, including the tumor volumes at the day of grouping (day 0), 14 days after the grouping (day 14), and at the end of the experiment (day 21), the survival rate of the mice, the number of tumor-free mice (non-existence of tumor), the Tumor Growth Inhibition value (TGI$_{TV}$), and the statistical differences (P value) in mouse body weights and tumor volume between the treatment and control groups.

group mice, the tumor volumes in the treatment groups were smaller than the control group (FIG. 19).

With respect to the tumor volume, in the control group (G1), the average tumor volume was 2800±673 mm$^3$. The tumor volumes in the treatment groups were 2286±271 mm$^3$ (G2), 1299±469 mm$^3$ (G3), and 1860±541 mm$^3$ (G4). The tumor volumes in the treatment groups G2-G4 were smaller than the control group G1. The results show that anti-human CD27 antibodies AB-1, AB-2, and AB-3 had different tumor inhibitory effects in B-hCD27 mice, with AB-2 (G3) having the best tumor inhibitory effects.

Example 10. Pharmacological Validation of B-hCD27 Humanized Animal Model with Murine CT26 Colon Carcinoma Cells B-hCD27 homozygous mice (4-6 weeks) were subcutaneously injected with CT26 cells derived from BALB/c mice. Because B-hCD27 homozygous mice have C57BL/6 background, the CT26 cells should not multiple easily or form tumors easily in B-hCD27 homozygous mice. The mice were divided to a control group and a treatment group 3 days after injection (n=5/group). The treatment group was administered with an anti-human CD27 antibody (Ab-4) (3 mg/kg); the control group was injected with an equal volume of blank solvent. The frequency of administration was twice a week (7 times of administrations in total). The body weight was measured twice a week. Two weeks after treatment

TABLE 15

| | | Tumor volume (mm$^3$) | | | Survival | Non-existence of tumor | TGI$_{TV}$ % | P value | |
|---|---|---|---|---|---|---|---|---|---|
| | | Day 0 | Day 14 | Day 21 | | | | Body weight | Tumor Volume |
| Control | G1 | 148 ± 25 | 1335 ± 274 | 2800 ± 673 | 5/5 | 0/5 | N/A | N/A | N/A |
| Treatment | G2 (AB-1) | 148 ± 24 | 1084 ± 176 | 2286 ± 271 | 5/5 | 0/5 | 19.4 | 0.484 | 0.499 |
| | G3 (AB-2) | 147 ± 26 | 672 ± 278 | 1299 ± 469 | 5/5 | 0/5 | 56.6 | 0.815 | 0.105 |
| | G4 (AB-3) | 147 ± 19 | 970 ± 365 | 1860 ± 541 | 5/5 | 0/5 | 34.5 | 0.703 | 0.308 |

Figure 17:
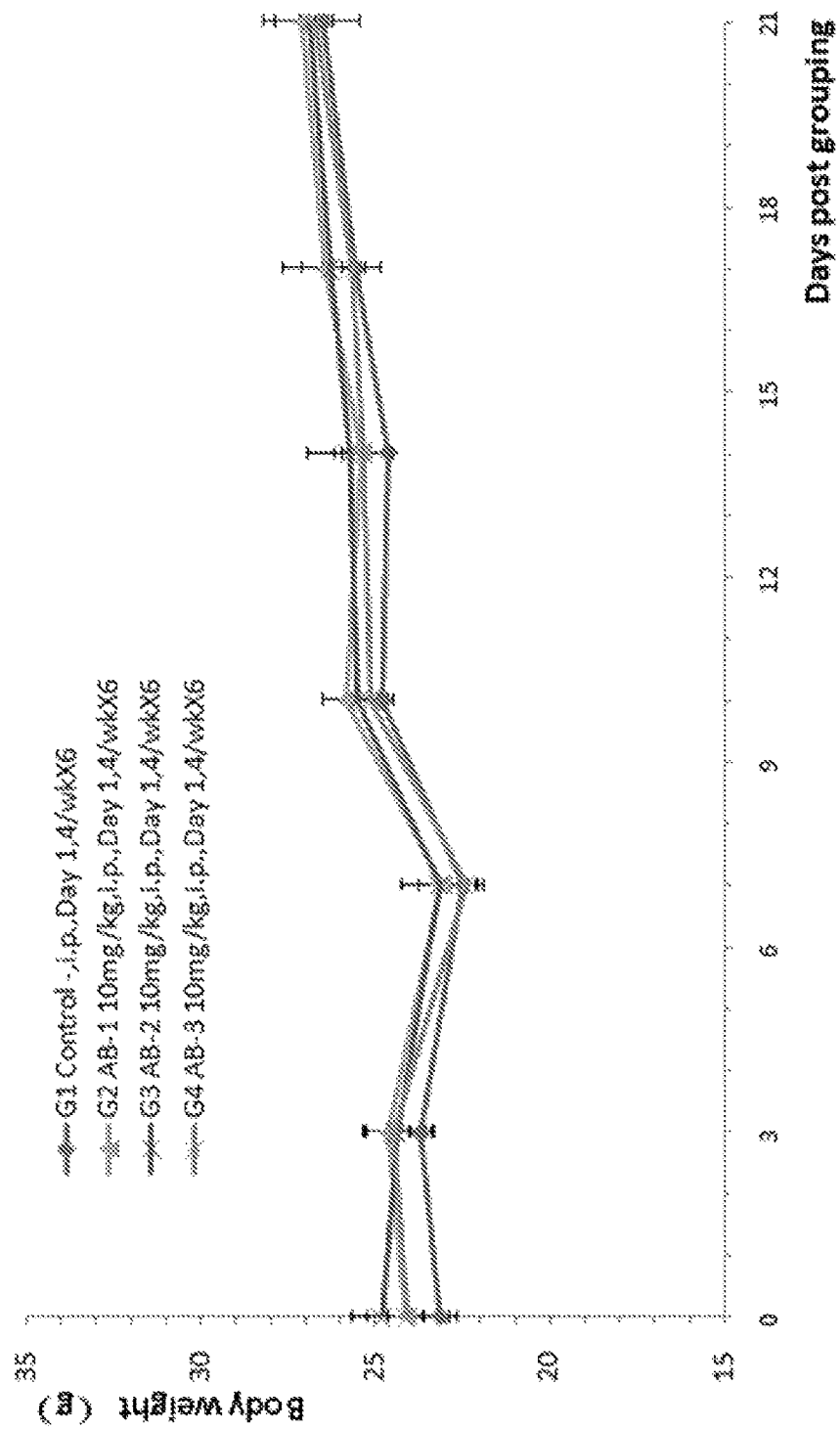
FIG. 17. Mouse colon cancer cells MC38 were injected into humanized CD27 homozygous mice. Antitumor efficacy studies were performed with three antibodies against human CD27 (AB-1, AB-2, and AB-3). The average weight of the G1 control group and the G2-G4 treatment groups are shown.
Figure 18:
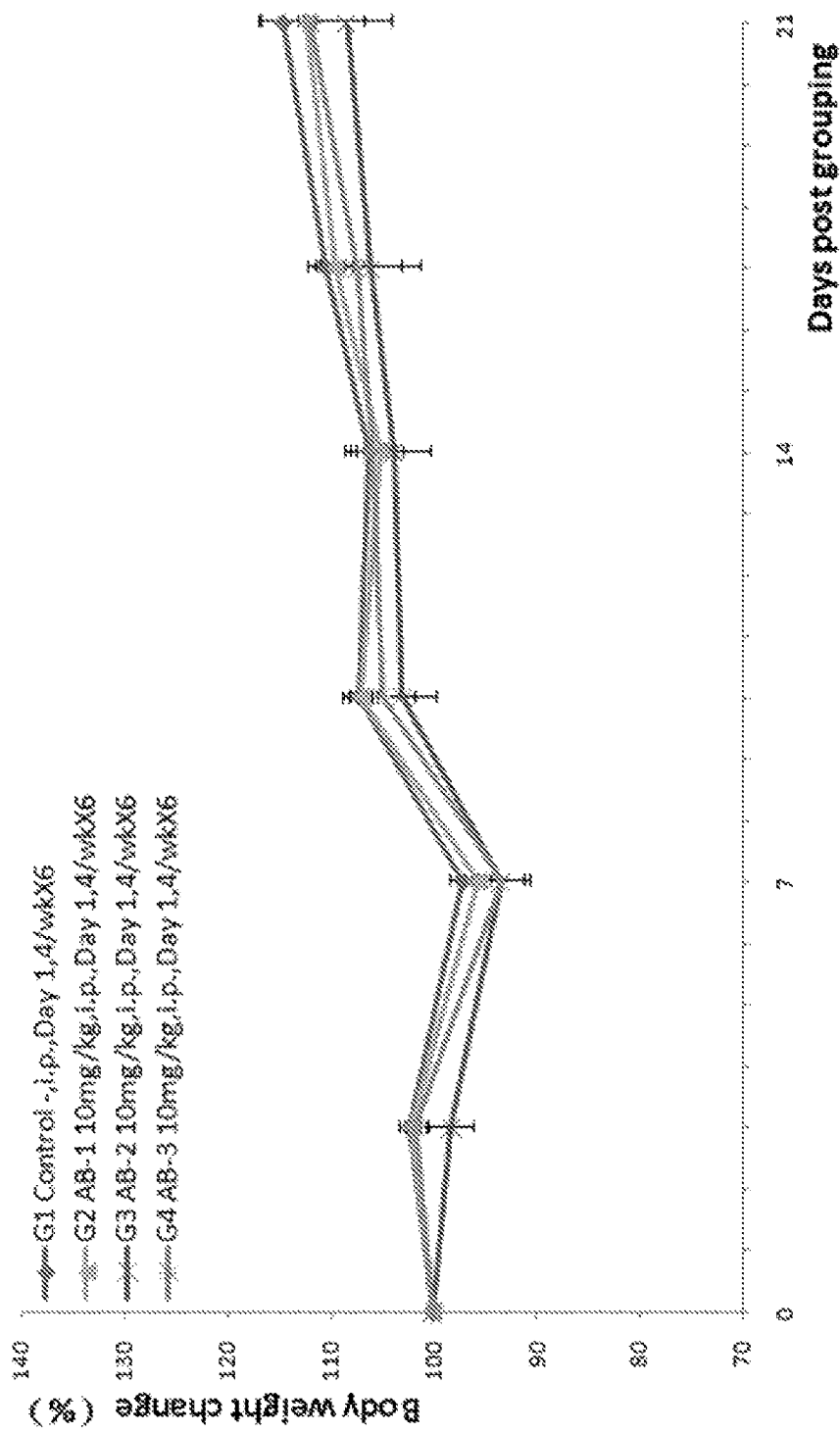
FIG. 18. Mouse colon cancer cells MC38 were injected into humanized CD27 homozygous mice. Antitumor efficacy studies were performed with three antibodies against human CD27 (AB-1, AB-2, and AB-3). The average weight change percentage of the G1 control group and the G2-G4 treatment groups are shown.

Overall, the animals in each group were healthy, and the body weights of all the treatment and control group mice slightly increased, and were not significantly different from each other (FIG. 17 and FIG. 18). The results indicated that the use of anti-human CD27 antibodies (AB-1, AB-2, and AB-3) were well tolerated and did not cause obvious toxic effects.

The tumor in the control group continued growing during the experimental period; when compared with the control started, the tumor volume was measured twice a week. Euthanasia was performed when the tumor reached 3000 mm$^3$.

Table 16 shows results for this experiment, including the tumor volumes at the day of grouping (day 0), 17 days after the grouping (day 17), and at the end of the experiment (day 20), the survival rate of the mice, the number of tumor-free mice (non-existence of tumor), and the statistical differences (P value) in mouse body weights and tumor volume between the treatment and control groups.

TABLE 16

| | | Tumor volume (mm³) | | | Non-existence | P value | |
| | | | | | | Body | Tumor |
| | | Day 0 | Day 17 | Day 20 | Survival | of tumor | weight | Volume |
|---|---|---|---|---|---|---|---|---|
| Control | G1 | 0 ± 0 | 50 ± 46 | 53 ± 53 | 5/5 | 4/5 | N/A | N/A |
| Treatment | G2 (Ab-4) | 0 ± 0 | 476 ± 134 | 562 ± 194 | 5/5 | 1/5 | 0.750 | 0.035 |

Figure 20:
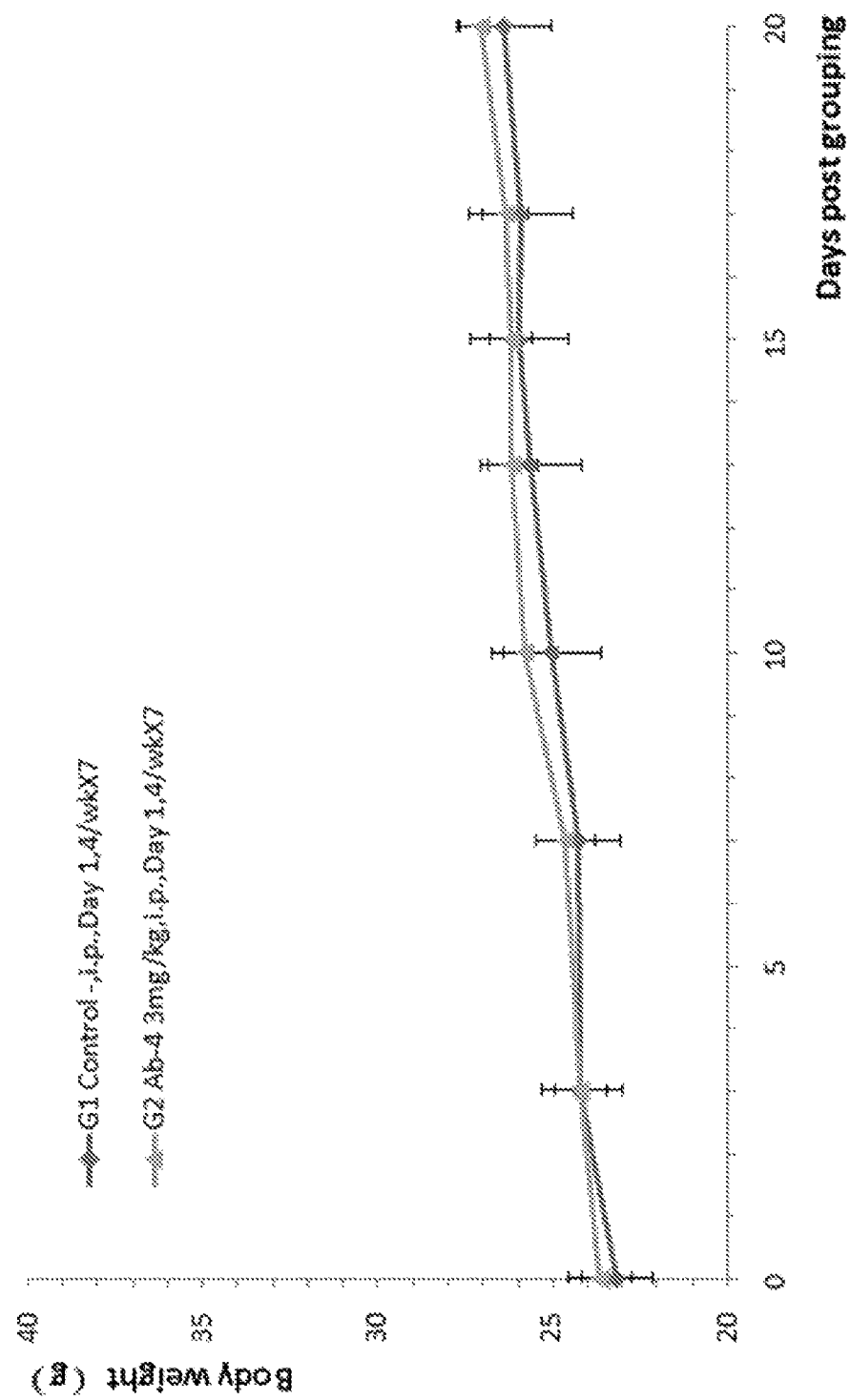
FIG. 20. Mouse colon cancer cells CT26 were injected into humanized CD27 homozygous mice. Antitumor efficacy studies were performed with an antibody against human CD27 (Ab-4, 3 mg/kg). The average weight of the G1 control group and the G2 treatment group are shown in this figure.
Figure 21:
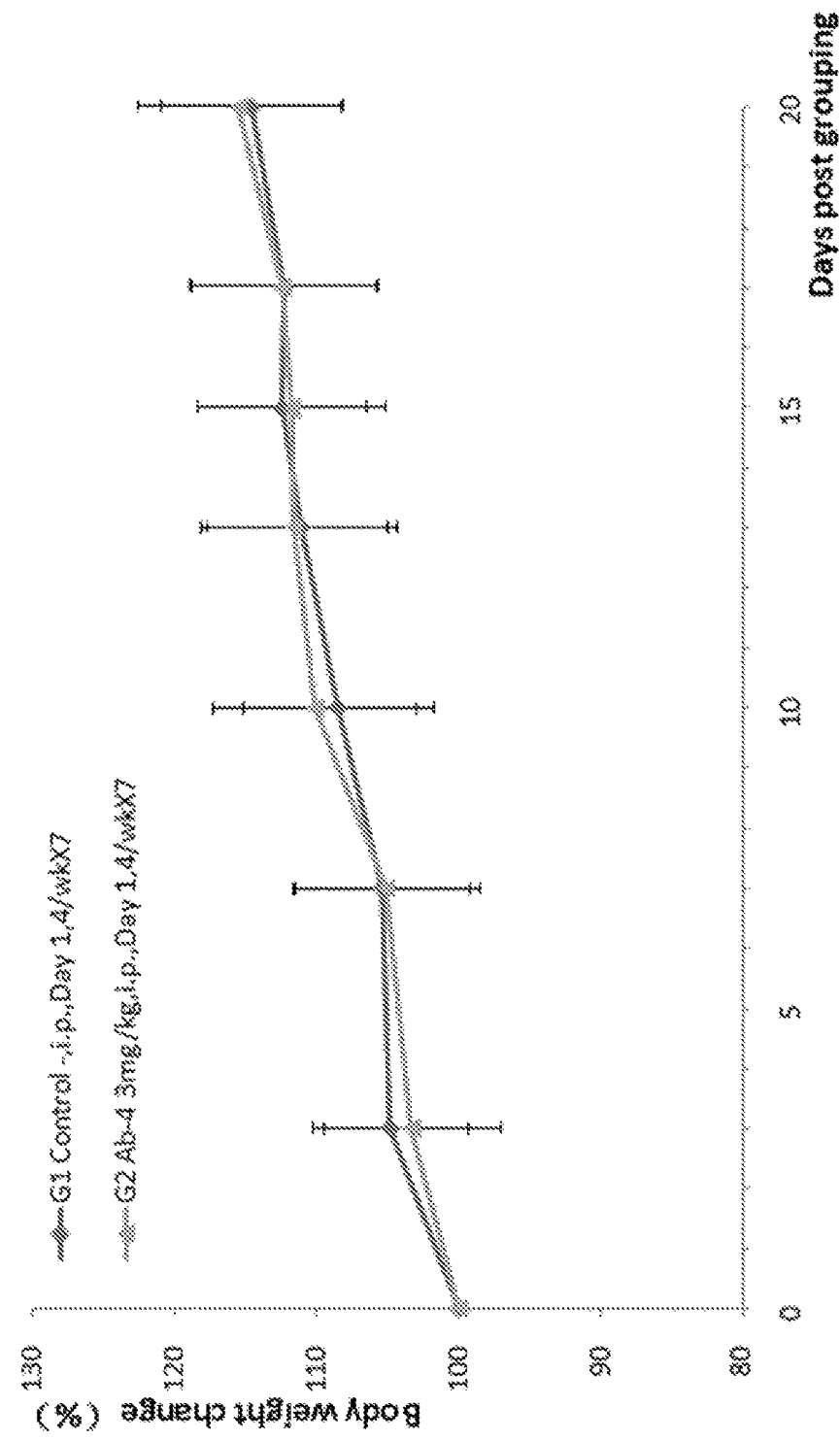
FIG. 21. Mouse colon cancer cells CT26 were injected into humanized CD27 homozygous mice. Antitumor efficacy studies were performed with an antibody against human CD27 (Ab-4, 3 mg/kg). The average weight change percentage of the G1 control group and the G2 treatment group are shown in this figure.
Figure 22:
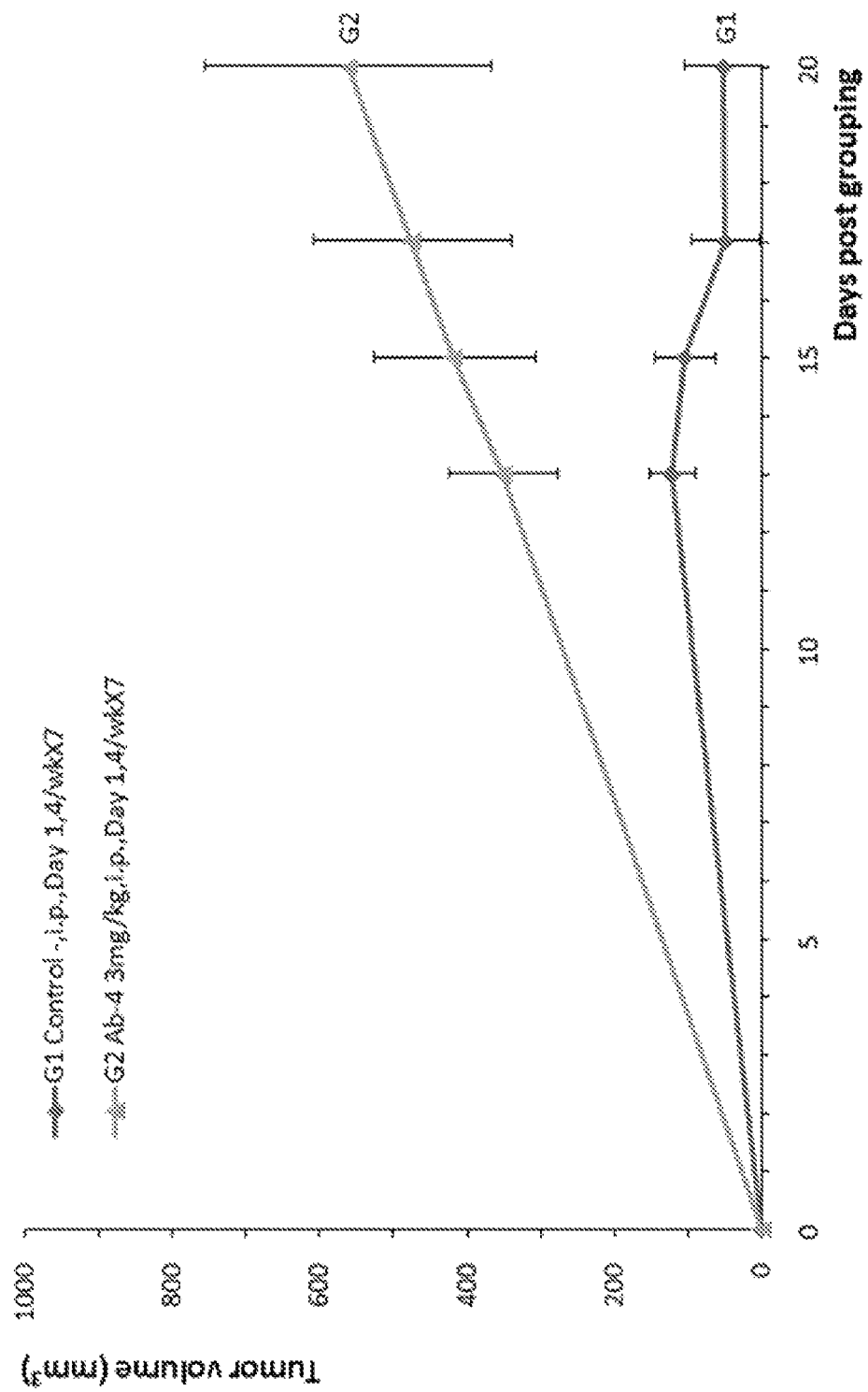
FIG. 22. Mouse colon cancer cells CT26 were injected into humanized CD27 homozygous mice. Antitumor efficacy studies were performed with an antibody against human CD27 (Ab-4, 3 mg/kg). The average volumes of tumors in the G1 control group and the G2 treatment group are shown in this figure.

Overall, the animals in each group were healthy, and the body weights of all the treatment and control group mice increased, and were not significantly different from each other (P>0.05) (FIG. 20 and FIG. 21). The results indicated that the use of anti-human CD27 antibody (Ab4) was well tolerated and did not cause obvious toxic effects.

At the end of the experiment, 4 mice (80%) in the control group had no tumor, and only 1 mouse (20%) in the treatment group was tumor-free. The average tumor volume in the control group was 53±53 mm³. The average tumor volume of in the treatment group was 562±194 mm³ (G2). There was a significant difference (P<0.05) between the tumor volume of the two groups, indicating that the human CD-27 monoclonal antibody Ab4 can inhibit immune response, and promote the growth of tumor cells.

In summary, the CD27 humanized mice can be used for screening human CD27 antibodies with immunosuppressive effects.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse whose genome comprises at least one chromosome comprising a nucleic acid sequence encoding a human or chimeric CD27, wherein the mouse expresses the human or chimeric CD27 on the surface of one or more spleen cells after the genetically modified mouse is stimulated by anti-CD3 antibody, and the mouse does not express endogenous CD27.

2. The mouse of claim 1, wherein the nucleic acid sequence encoding the human or chimeric CD27 is operably linked to an endogenous regulatory element at the endogenous CD27 gene locus in the at least one chromosome.

3. The mouse of claim 1, wherein the nucleic acid sequence encodes an amino acid sequence that is at least 70% identical to SEQ ID NO: 18.

4. The mouse of claim 1, wherein the nucleic acid sequence encodes an amino acid sequence that is at least 70% identical to SEQ ID NO: 24.

5. The mouse of claim 1, wherein the nucleic acid sequence encodes a human or chimeric CD27 comprising amino acids 1-183 of SEQ ID NO: 18.

6. The mouse of claim 1, wherein the genome of the mouse comprises a replacement of a sequence encoding a region of endogenous CD27 with a sequence encoding a corresponding region of human CD27 at an endogenous CD27 gene locus.

7. The mouse of claim 6, wherein the region of the endogenous CD27 is the extracellular region of CD27.

8. The mouse of claim 6, wherein the mouse has one or more spleen cells expressing a chimeric CD27 having an extracellular region, a transmembrane region, and a cytoplasmic region, wherein the extracellular region comprises a sequence that is at least 80% identical to the extracellular region of human CD27.

9. The mouse of claim 6, wherein the mouse is homozygous with respect to the replacement at the endogenous CD27 gene locus.

10. The mouse of claim 1, wherein the nucleic acid sequence encodes an amino acid sequence that is at least 90% identical to SEQ ID NO: 24.

11. The mouse of claim 1, wherein the nucleic acid sequence encodes an amino acid sequence that is at least 95% identical to SEQ ID NO: 24.

12. The mouse of claim 1, wherein the nucleic acid sequence encodes an amino acid sequence comprising SEQ ID NO: 24.

* * * * *

```
                        SEQUENCE LISTING

<160> NUMBER OF SEQ ID NOS: 48

<210> SEQ ID NO 1
<211> LENGTH: 44
<212> TYPE: DNA
<213> ORGANISM: Artificial
<220> FEATURE:
<223> OTHER INFORMATION: PCR primer

<400> SEQUENCE: 1
cgatctcgag atttaaataa tctgtaatct gctcctatct ggtc                44

<210> SEQ ID NO 2
<211> LENGTH: 39
<212> TYPE: DNA
<213> ORGANISM: Artificial
<220> FEATURE:
<223> OTHER INFORMATION: PCR primer

<400> SEQUENCE: 2
agggatgtgg ccgtgccata gctcctgccc agggagatc                     39

<210> SEQ ID NO 3
<211> LENGTH: 39
<212> TYPE: DNA
<213> ORGANISM: Artificial
<220> FEATURE:
<223> OTHER INFORMATION: PCR primer

<400> SEQUENCE: 3
gatctccctg ggcaggagct atggcacggc cacatccct                     39

<210> SEQ ID NO 4
<211> LENGTH: 43
<212> TYPE: DNA
<213> ORGANISM: Artificial
<220> FEATURE:
<223> OTHER INFORMATION: PCR primer
```

```
<400> SEQUENCE: 4
ggtaggagtg gggagtactg gttaacccgt caccagcctt gct                43

<210> SEQ ID NO 5
<211> LENGTH: 43
<212> TYPE: DNA
<213> ORGANISM: Artificial
<220> FEATURE:
<223> OTHER INFORMATION: PCR primer

<400> SEQUENCE: 5
agcaaggctg gtgacgggtt aaccagtact ccccactcct acc                43

<210> SEQ ID NO 6
<211> LENGTH: 45
<212> TYPE: DNA
<213> ORGANISM: Artificial
<220> FEATURE:
<223> OTHER INFORMATION: PCR primer

<400> SEQUENCE: 6
gatgcagtcc gagctgcaca gggatctttg ggctgtaata ggagg              45

<210> SEQ ID NO 7
<211> LENGTH: 45
<212> TYPE: DNA
<213> ORGANISM: Artificial
<220> FEATURE:
<223> OTHER INFORMATION: PCR primer

<400> SEQUENCE: 7
cctcctatta cagcccaaag atccctgtgc agctcggact gcatc              45

<210> SEQ ID NO 8
<211> LENGTH: 46
<212> TYPE: DNA
<213> ORGANISM: Artificial
<220> FEATURE:
<223> OTHER INFORMATION: PCR primer

<400> SEQUENCE: 8
cgatgaattc attaatgcat ttacactatc cttcttccta gttcac             46

<210> SEQ ID NO 9
<211> LENGTH: 51
<212> TYPE: DNA
<213> ORGANISM: Artificial
<220> FEATURE:
<223> OTHER INFORMATION: PCR primer

<400> SEQUENCE: 9
cgatggatcc aatattcaat tgtaacttca aatacgcaca cctacaactg a        51

<210> SEQ ID NO 10
<211> LENGTH: 37
<212> TYPE: DNA
<213> ORGANISM: Artificial
<220> FEATURE:
<223> OTHER INFORMATION: PCR primer

<400> SEQUENCE: 10
cgatgcggcc gcatttaaat cctttgggtc tgccctg                       37

<210> SEQ ID NO 11
<211> LENGTH: 47
```

```
<212> TYPE: DNA
<213> ORGANISM: Artificial
<220> FEATURE:
<223> OTHER INFORMATION: PCR primer

<400> SEQUENCE: 11
gctggtaccg gcgcgcctcg agaaggaatg tcaagtacca tggctgg          47

<210> SEQ ID NO 12
<211> LENGTH: 37
<212> TYPE: DNA
<213> ORGANISM: Artificial
<220> FEATURE:
<223> OTHER INFORMATION: PCR primer

<400> SEQUENCE: 12
ggagatctgg cagatatcac aggggacag cacttac                      37

<210> SEQ ID NO 13
<211> LENGTH: 33
<212> TYPE: DNA
<213> ORGANISM: Artificial
<220> FEATURE:
<223> OTHER INFORMATION: PCR primer

<400> SEQUENCE: 13
ccctgtgata tctgccagat ctccacctct ctg                         33

<210> SEQ ID NO 14
<211> LENGTH: 48
<212> TYPE: DNA
<213> ORGANISM: Artificial
<220> FEATURE:
<223> OTHER INFORMATION: PCR primer

<400> SEQUENCE: 14
tcctcttcag acctggcggc cgcttgggga taaatcgcct tgtatcag         48

<210> SEQ ID NO 15
<211> LENGTH: 1576
<212> TYPE: DNA
<213> ORGANISM: Mus musculus

<400> SEQUENCE: 15
cagccacaac tgccttcaaa ggtcggttta ccacccaagt ggagtcgcag tggctgctgc    60
ccagagcaca taggagccac cagtgactcg gtacaagcag ttggggctca gaaaagatct   120
ccctgggcag gagctatggc atggccacct ccctactggc tctgcatgct ggggaccttg   180
gtaggactct cagctaccct agccccaaac agctgtccag acaaacacta ctggactggg   240
ggaggactct gctgccggat gtgtgagcca ggtacattct ttgtgaagga ctgtgaacaa   300
gacagaacag ctgctcagtg tgatccctgt ataccaggca cctccttctc tccagactac   360
cacacccggc cccactgcga gagctgcagg cattgtaact ctggttttct tatccgcaac   420
tgcacagtca ctgccaatgc tgagtgcagc tgttccaaga ctggcagtg cagggaccag   480
gaatgtacag agtgtgaccc tcctctaaac cctgcactga ccagacagcc atctgagacc   540
ccgagcccac agccaccacc cacccactta cctcatggca cagagaagcc atcctggccc   600
ctacacaggc agcttcccaa ctcgactgtc tatagccagc ggtcatccca tagacccctg   660
tgcagctcgg actgcatccg gatctttgtg accttctcca gcatgtttct tatcttcgtc   720
ctgggtgcaa tcttgttctt ccatcaaaga agaaaccacg ggccaaatga agaccggcag   780
```

-continued

```
gcagtgcctg aagagccttg tccttacagc tgccccaggg aagaggaggg cagtgctatc    840
cctatccagg aggactaccg gaaacccgag cctgctttct acccttgacc gggtgctggt    900
ggggcccttt ctgacgaggg gccatccaca gagacctcaa tggtggcctg ctcccctgtc    960
atggtcatca gaacccttc ctgtgaatac tcaacaaact gcccttctga gaccaacagg    1020
gacaagagca ggatcccagt gtgtggccca gcaagctggg gagactcagg ctctagctat    1080
aaagcacact tactctaagt gaaaccgtcc agctgacaaa actacatgcc aggggtggaa    1140
atggctcacc aagggctcca gaggggggctt ggcagtgagg agcacgaagt gttcctccag    1200
aggaccagag tttgattccc agcactgtca aatggatcga aaccagctgt aactctactt    1260
tcagagggtc tgacaccttt gacctcctct ggcatctaca aacacaggac ggacacacac    1320
acacacacac acacacacac acacacacac acgattaaaa ataataattt ttttaaaaa    1380 aatggaatga gccaccggca ggtgccctgg taccagaagg actgactgcc gtgagagaca    1440
ctatctacag acacacagac ttcctggcct tggttctgtc ttctctgtaa gttgtgacag    1500
tgctgtggga aagctgaggc tgagactttc tctcagttga gctaaaacta taaataaatt    1560
catttgtcta cttcta                                                   1576
```

<210> SEQ ID NO 16
<211> LENGTH: 250
<212> TYPE: PRT
<213> ORGANISM: Mus musculus

<400> SEQUENCE: 16

```
Met Ala Trp Pro Pro Tyr Trp Leu Cys Met Leu Gly Thr Leu Val
1               5                   10                  15

Gly Leu Ser Ala Thr Leu Ala Pro Asn Ser Cys Pro Asp Lys His Tyr
            20                  25                  30

Trp Thr Gly Gly Gly Leu Cys Cys Arg Met Cys Glu Pro Gly Thr Phe
        35                  40                  45

Phe Val Lys Asp Cys Glu Gln Asp Arg Thr Ala Ala Gln Cys Asp Pro
    50                  55                  60

Cys Ile Pro Gly Thr Ser Phe Ser Pro Asp Tyr His Thr Arg Pro His
65                  70                  75                  80

Cys Glu Ser Cys Arg His Cys Asn Ser Gly Phe Leu Ile Arg Asn Cys
                85                  90                  95

Thr Val Thr Ala Asn Ala Glu Cys Ser Cys Ser Lys Asn Trp Gln Cys
            100                 105                 110

Arg Asp Gln Glu Cys Thr Glu Cys Asp Pro Pro Leu Asn Pro Ala Leu
        115                 120                 125

Thr Arg Gln Pro Ser Glu Thr Pro Ser Pro Gln Pro Pro Thr His
    130                 135                 140

Leu Pro His Gly Thr Glu Lys Pro Ser Trp Pro Leu His Arg Gln Leu
145                 150                 155                 160

Pro Asn Ser Thr Val Tyr Ser Gln Arg Ser His Arg Pro Leu Cys
                165                 170                 175

Ser Ser Asp Cys Ile Arg Ile Phe Val Thr Phe Ser Ser Met Phe Leu
            180                 185                 190

Ile Phe Val Leu Gly Ala Ile Leu Phe Phe His Gln Arg Arg Asn His
        195                 200                 205

Gly Pro Asn Glu Asp Arg Gln Ala Val Pro Glu Glu Pro Cys Pro Tyr
    210                 215                 220

Ser Cys Pro Arg Glu Glu Glu Gly Ser Ala Ile Pro Ile Gln Glu Asp
```

```
                225                 230                 235                 240

Tyr Arg Lys Pro Glu Pro Ala Phe Tyr Pro
                245                 250

<210> SEQ ID NO 17
<211> LENGTH: 1320
<212> TYPE: DNA
<213> ORGANISM: Homo sapiens

<400> SEQUENCE: 17
cggaagggga aggggtgga ggttgctgct atgagagaga aaaaaaaaac agccacaata     60
gagattctgc cttcaaaggt tggcttgcca cctgaagcag ccactgccca gggggtgcaa    120
agaagagaca gcagcgccca gcttggaggt gctaactcca gaggccagca tcagcaactg    180
ggcacagaaa ggagccgcct gggcagggac catggcacgg ccacatccct ggtggctgtg    240
cgttctgggg accctggtgg ggctctcagc tactccagcc cccaagagct gcccagagag    300
gcactactgg gctcagggaa agctgtgctg ccagatgtgt gagccaggaa cattcctcgt    360
gaaggactgt gaccagcata gaaaggctgc tcagtgtgat ccttgcatac cggggtctc    420
cttctctcct gaccaccaca cccggcccca ctgtgagagc tgtcggcact gtaactctgg    480
tcttctcgtt cgcaactgca ccatcactgc caatgctgag tgtgcctgtc gcaatggctg    540
gcagtgcagg gacaaggagt gcaccgagtg tgatcctctt ccaaaccctt cgctgaccgc    600
tcggtcgtct caggccctga gcccacaccc tcagcccacc cacttacctt atgtcagtga    660
gatgctggag gccaggacag ctgggcacat gcagactctg gctgacttca ggcagctgcc    720
tgcccggact ctctctaccc actggccacc ccaaagatcc ctgtgcagct ccgattttat    780
tcgcatcctt gtgatcttct ctggaatgtt ccttgttttc accctggccg ggcctgtt    840
cctccatcaa cgaaggaaat atagatcaaa caaggagaa agtcctgtgg agcctgcaga    900
gccttgtcgt tacagctgcc caggggagga ggagggcagc accatcccca tccaggagga    960
ttaccgaaaa ccggagcctg cctgctcccc ctgagccagc cctgcggga gctgcactac   1020
agccctggcc tccaccccca cccgccgac catccaaggg agagtgagac ctggcagcca   1080
caactgcagt cccatcctct tgtcagggcc ctttcctgtg tacacgtgac agagtgcctt   1140
ttcgagactg gcaggacga ggacaaatat ggatgaggtg gagagtggga agcaggagcc   1200
cagccagctg cgcctgcgct gcaggagggc gggggctctg gttgtaaaac acacttcctg   1260
ctgcgaaaga cccacatgct acaagacggg caaaataaag tgacagatga ccaccctgca   1320

<210> SEQ ID NO 18
<211> LENGTH: 260
<212> TYPE: PRT
<213> ORGANISM: Homo sapiens

<400> SEQUENCE: 18

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80
```

```
Cys Glu Ser Cys Arg His Cys Asn Ser Gly Leu Leu Val Arg Asn Cys
                 85                  90                  95
Thr Ile Thr Ala Asn Ala Glu Cys Ala Cys Arg Asn Gly Trp Gln Cys
            100                 105                 110
Arg Asp Lys Glu Cys Thr Glu Cys Asp Pro Leu Pro Asn Pro Ser Leu
        115                 120                 125
Thr Ala Arg Ser Ser Gln Ala Leu Ser Pro His Pro Gln Pro Thr His
    130                 135                 140
Leu Pro Tyr Val Ser Glu Met Leu Glu Ala Arg Thr Ala Gly His Met
145                 150                 155                 160
Gln Thr Leu Ala Asp Phe Arg Gln Leu Pro Ala Arg Thr Leu Ser Thr
                165                 170                 175
His Trp Pro Pro Gln Arg Ser Leu Cys Ser Ser Asp Phe Ile Arg Ile
            180                 185                 190
Leu Val Ile Phe Ser Gly Met Phe Leu Val Phe Thr Leu Ala Gly Ala
        195                 200                 205
Leu Phe Leu His Gln Arg Arg Lys Tyr Arg Ser Asn Lys Gly Glu Ser
    210                 215                 220
Pro Val Glu Pro Ala Glu Pro Cys Arg Tyr Ser Cys Pro Arg Glu Glu
225                 230                 235                 240
Glu Gly Ser Thr Ile Pro Ile Gln Glu Asp Tyr Arg Lys Pro Glu Pro
                245                 250                 255
Ala Cys Ser Pro
            260

<210> SEQ ID NO 19
<211> LENGTH: 4303
<212> TYPE: DNA
<213> ORGANISM: Mus musculus

<400> SEQUENCE: 19
aaggaatgtc aagtaccatg gctggggaca gcactgaatc cagaggcagc tgccaaggcg     60
ctgtcagcaa gcactgtcca gagcttcgct tacccagagt ctgagaaaga aaaccgttag    120
agctaccaga caggacactg acaataaat  cctcctaaat aaagtagaag ccttaaggga    180
atctaaacaa agagccggaa cctactcaac aattcagaag ctcagccatt tgtctgctcc    240
aaaaaatgtc ttcccagagg gcctcaaaac agcacctgct gtagccttgc tcctgctgtc    300
accacagtca gatgtgaaga ccctattgct gaaaacgtaa cacagtgtgg cagtgtggt    360 cgctagagag atagttctgg gttatataga aagcaggttg agcaagccag taagtgctgt    420
ccccctgtga tctctgcttc agttcctgcc tccaggttct gtaagtcaga agtctaaagg    480
aggcctcagc cagggatgca gctcacggcc tggcctcagc ccccaactca ttgccctcat    540
cttccttccg tcttgcaaat cagcaatgag tcctcatatg actgcttgtt tgttcttctg    600
cttccacttg agaccactta atatgccag  cagagctgtg cacctcttta atcccaagca    660
ttcaggtggc agaggcaggt ggatctcaga gtttgagacc agcatggtct acagatgtaa    720
acaacaccga gagacagggt cctcctggct ggcacaggct tcggcctttt ctttctccca    780
gcatgagatt cctggggaaa ttccagtttc ttggggacca tttttgcag tcatttctgt    840 agccaaagga tatcttcatt cctaccaggg caggagaata aaaacattca acacataaa    900 ataaacaaac cctttgaaat tattttaaaa tattttcaaa acatatttc taataagaga    960 ttagtatctg aaacagtaac taaaatcaag atgattagaa cagaagcaaa agacctaata   1020
```

-continued

```
aacatttctt cagagaagag gtacaattct cgataagcat gtgaaaggct aaggagagga   1080
gaattgggat ctcacggttt agcaggtatg gagtttgggg ttatattgct tgttcatgta   1140 tgaggggggag ggcgttggtc tcactgcttc tggccaggat ggtctcctgg acttaaatga  1200
cccctcccac tcaagctccc gaggaccaag aacctcagac aggcacatgt catcatgtcc   1260
agcttaagag ttccaatttt atagtataaa gagaatatac agatgaaagg tgatgcgttg   1320
gctgtcatgg ttacagcgaa actacttcag aagacaactt ggaaggagaa aggagttgac   1380
ttcggttcac agtgtcagag atgtcaacct ctgactgact agtgccattg cttctgggcc   1440
tgtggtgaag cagaacttta tggtgaaaag ggtgtggcag agtcctctca cttcacagca   1500
tctagaaagc agagacaccg agggagacgg agagaggaag gaaggccatg aggataagac   1560
acaccattca aaggcttgat tctagtgagc cactaattct aacttggccc cactgcctat   1620
ttagccatgt agtcatcaag ggagtacttc gtggatgaag cctgcttacc tccccatggc   1680
actgctgctc cagccatgag ccctctgcgg tacatcat atctaccttg ttagggtttc     1740
cattgctgtg aagagacacc atggccaggg caactcttat aaaggaaagc atttcattgg   1800
ggctggctta cagtttcaga ggtttagtcc attatcatca tggcaggaag catggcagtg   1860
tgaagaaggc acggtgcggg aggagatgag agatctacat cttgatccta aggcagccag   1920
gagactttca tccacactgg gtagagcctg agcattggag gaaaccttaa agccacaact   1980
atacacttct tccagcaaag ccatactcta accaggccac acctcctaaa aatgccactc   2040
cctgggccaa gcattcaagc acatgagtct atggggccca aatctattca aaccaccaca   2100
ttaggcaaac ctaacaccag tgttacttca ggagagccaa gcaggccctg tccctgtcct   2160
gagcctgtgg aggaagatag actttgaacc tagaggtgga ggctttagat gaggacacaa   2220
ctcatggtct ggccaagatg ttaagttctc tgtgcactca aagcctcttt ttagcaactt   2280
tctttctaca gttcttcaac gccaggtcct attcattcct acagggtcag ccgtcagctc   2340
cccgcaccca tgcatctgt cttcagattt atgactaacg gtgaagatgt tggagcctgg    2400
gaatgaggaa ggaaattcct tccgttgtaa agttgtcgcg gcctctgctg ggcatgtggt   2460
ggagggtggt ttccttaaa cagaacatgc tgcagctcct ggctcgagtg gacccttgaa    2520
gagctgtagt gggggctggg gaaagggagg agggtggaaa aaatgaagag acaggaagct   2580
gaagcatgag atagaaagaa cagatctaac atcccccagg tgcgaccaca gggctgtgac   2640
atttcaccaa cactatggaa acaactgtga agcccccaaa tgagacatat ccttgagata   2700
agtcagcagg ggaaagagtg gagggggttc aatggcccgt gcttctccag tgtagcaact   2760
ccagcatcct caaatcagaa ttcccagagg agcatgaggc ttaagatgat ggcccacgta   2820
ggtgcccacc ttcaatccca tgtgcccagg gccatgaaga gagatggctc aggtacctga   2880
agatactagt gaccaagcca gccagaagca ggaaggataa aaatgggatt aggtcaagaa   2940
ggaagtttgg caaagttcc cccaggcagt gggtcacatc tgtgtcacag gctggcatta    3000
agaagaaata aaaccaggct ggagtggtag ctcagtcagg aaagtacaag ggcctgagtc   3060
tgatcgccaa aacccagttt ttgagttcat ttctttgttt gtttgttttg ctaaaggatc   3120
ccagggtttg atggtcatcc agcctcctct actaggcaag ttgcaggcca gtgagaaata   3180
ataatctcca tcttctttat catcaccacc accatcatca tcatcatcga tgtccctgag   3240
gaatgaaacc aaggttgtcc cctgacctcc atacgcatga acctacac acacacacac     3300 acacacacac acacacacac acacacacac acacacatgt gcacacaagg attaaaggga   3360
cttgatatca cagaacagaa aaagacacag ggaacacagg gctaactctt gccctcaatt   3420
```

```
gtatgcaatg ttcaagagct tgtatagcca gaaactcaaa cctcagttat ataaggctgg   3480
ttgtcatgac tcctcccctt tatacatgca atagctttgc tgcgtgtgct gtgtccaagc   3540
tgggaatata gctcagacag cagtgtttgc ctaggatgca aaaagccctg ggtttcatcc   3600
ccagtaccac ataaacggga tgcggcagca cagcgctatg caccagcag cagtggcttg    3660 gtagcaaacc ctgcaacacc aggaacactc aggagaggga ggcagaaaga tcagaagtcc   3720
caagtcatcc tcagctacca agcaaccttg aggctacctt ggcatatata agaccgtctt   3780
ccaaactgtt gtgcttagcc gtgtcacccc acctctaatg gggtgttttg tggtactagt   3840
tttaggcaaa atctgaaaat gtcatgattt taaaactaac ctgcccctag gagcttcaga   3900
aataatctgt aatctgctcc tatctggtca cctctggaag ggctgggcta tgagagagga   3960
cacttgccag ggacagatga gggcacccag cgtccatccc tatcaacagg tccggcggct   4020
gtgggtattc attactgaga gaggtgccca agggggcac atgtctgtga agctcagcag    4080
agctgggttt accccttcat agtctctccg gagtgcggaa aagagaaggg ggtggaggct   4140
gctgagagag agacaaagaa aaccaaaaca gccacaactg ccttcaaagg tcggtttacc   4200
acccaagtgg agtcgcagtg gctgctgccc agagcacata ggagccacca gtgactcggt   4260
acaagcagtt ggggctcaga aaagatctcc ctgggcagga gct                    4303

<210> SEQ ID NO 20
<211> LENGTH: 4742
<212> TYPE: DNA
<213> ORGANISM: Mus musculus

<400> SEQUENCE: 20
taacttcaaa tacgcacacc tacaactgaa acaaacaaac aaacaatccc tcagtgtggc     60
cctgagcttg taattcaagg ggttaagtgg tgtgacaagg gcggggcttg gagtagagac    120
agcaggagat cactgctgtg cttgttggct accaaacaat tccaggttca gaaagagacc    180
ctgtctctga agaataaggt ggggtaatag agcaagacac ccagtgccct caccgagcct    240
ccacacacag gcagggctgg gcatactcac ccacacaagt gtatacaccg catatacaca    300
aatacaagtt aaaagtgaga cttcacatag ctgtccagcc tcctaaaatt ccaatcctag    360
aactaggcca caccccatct cgtctgttcg atcacagatc tgaacaggga gttgtcacca    420
gggcagaccc aaaggattta acatggactg aaaggaagaa gggtcagag taccggggaa     480 tctatcttct ggctccaccc cctctccagc cctctcatag ttgggctga tgggaaagct     540 gatgtggtga taccaggttt tgaaatcacc tggggatttc ttgggtgcgg ggtggacctt    600
agggagaaca gaaagcagag ctggctgcag ccattactgg cctcgggcgg gcggccacag    660
aggcagttga agtgaaagtg aaagagaaac gataagagaa cggagaccac aggtgctaag    720
tgagggtgct cacagaaccc cctcttcagc cagagatcac tagcagggga actgtggaga   780
aggcagccag caaggaagag cctgagagta gcctccatgg gcttggagcc cagctggtat   840
ctgctgctct gtttggctgt tctggggca gcagggactg gtgagtgcgg agaccaggct     900
ggggcctggg ggactggggg ggaggaagcg ccaagctaaa ggagcccag gaagccacct     960 tctcagaaca gcaccagctt gtctgctaag cccagcaaat gagtgcggca ctcacaacat   1020
gcggaaccag tttggagagg ggtacggcag agaactcaca gaaaagggg gcttcctcga    1080 tgggaaggca gggtgttagc attctgtggg acagctcact gccctgagtt gaatccttag   1140
aagaggaagg ggctccccag gctaagaaat cattggggttg gtgactcctg gtgggcgtgg   1200
```

```
ctatggcaga aagcagaggc ctctgggaaa gttgggtgat gagaaaaagg ttgtcaatgt    1260
ccctaggaac agcagtgtct tggctcctct ccctgtggc agtatttctt attccttttt    1320
tttttttttt tttttaacct gagaattcct ttccagaaat tcccttgcat cccacagctg    1380
agactcagaa atacaaagca taaacccctc tggctttgat caggacagat ctaggacttg    1440
aaataactca cagagccgct gcctgagtag caggtgcctc agcagaagct gggtttatag    1500
atgacaccag acagcggggg ctcagaaggc acctttacct gctgctcagc ccggggcttg    1560
gtgaaggggt gggaagagtg tggaggacga gggtgcttgt tccactttcc ctgcagaccc    1620
tcccacagcg cccaccacag cagaaagaca gcggcagccc acggacatca tcttagactg    1680
cttcttggtg acagaagaca ggcaccgcgg ggcttttgcc agcagtgggg acagggagag    1740
ggccttgctt gtgctgaagc aggtaccagt gctggatgat ggctccctgg aaggcatcac    1800
agatttccag gggagcactg agaccaaaca ggattcacct gttatctttg aggcctcagg    1860
taaaatctcc ccatcctagg cttcctccac aggaacagcc ccgttcccag ttctatctac    1920
ccacgcctgc ccccccccc cccggtctg gcgttgtcca tccaacatta cttctgtatg    1980
ctgcccttct ccccagtgga cttggtacag attccccagg cagaggcgtt gctccatgct    2040
gactgcagcg ggaaggcagt gacctgcgag atctccaagt atttcctcca ggccagacaa    2100
gaggccactt ttgagaaagc acattggttc atcagcaaca tgcaggtttc tagaggtggc    2160
cccagtgtct ccatggtgat gaagactcta agagatgctg aagttggagc tgtccggcac    2220
cctacactga acctacctct gagtgcccag ggcacagtga agactcaagg tgagaaaaca    2280
aaatgcagtg gcacaggaac attttgtatt attgtgtgtg tgtgtgtgtg tgcgcgtcca    2340
tgcgcacata cgtgtgcaca tgccacagca cataggtaga gatcagagga cagcttatag    2400
aacctaccat gtggtttcca gggattgaac tagttcacta tgcttggcag caagcacttt    2460
atgcactatg ccatctcaat agccccaaga tagttttttg gttttttggt tttggttttt    2520
tttttttttt gggggggggg ttgttgtttt tttaatttgt ttttttgtttg tttggttggt    2580 ttgttggttg gtatttttgtt ttcttttgtg gttagagatg ggatagaagg aagaaaacaa    2640
atatcccaca ggtcctcctg aggtacccat agagcttcat cttttctttc taaaatatcc    2700
tgagtcaaga agaggggatg ctaggagatc cttattcgag caagcatcaa aacataataa    2760
tcatcaggta ttttctccaa agtggggaag caacacatga ggacactgta gctacacatg    2820
tcactacact cttatttagc caaactcatg tttcctccca gggagaggga gtctggtctg    2880
gtgcttcatg gcaattacag cagagcacag ggagaaagaa gtgctcagta gctcttacta    2940
gtgagcccat tcctcattct ctcccactta gtacctccta ccaggttcaa aaccaagagg    3000
aaacatattg acaggcacct ggagagtcca gttcattatt ttgcctccaa aaaggagaaa    3060
atcaagtcca cagaagatga cgatgagggg gcccctctcc tatccctgca aaccccctaaa   3120 acattagcct ttagtattat gttgtcccat actgaggata gaacctagag ccttgtgcta    3180
aacacgagct ctactactaa actacagctt caattccttt ttcagtttta ttgtgaaaca    3240
ggggtctcac ccagatgccc tggcaggcct ggaaacttgt gattctgtca tgcctcctta    3300
gtagctgatg gtacaggcat atactaccac acctccggc tctacagtcc tttctgaatg    3360
tgccttgcca catcagaaaa gatgttcagc atctcctatc cttggccatg ggtagtttag    3420
tgcttctccc ttttgaact tattcagatc tacaaataaa tgaaacaaca tacccccacc    3480
cagccgtgac ttatttctga cctatttcgt cagctgtcat agttcctctc tacccgacta    3540
acatagatat cctcccctgg actgactagg ctgtagggac cacaacactt caccccccaaa   3600
```

```
tgctcccatg tgcagttagg gctgatagct gaaagtcaag gccactctgc ttcacaataa    3660
ccaaggatcc caaaagccta tcaaggctgg ggagtgctct actcacagta acaagggtcc    3720
agtgcacaca ggacttaaca gtatttcatt catggaaaga cgtgactatt gaagctggac    3780
gtactgtcca catctgcagt ccttgcactt ggagggactg aaccacgaag attgtgggtt    3840
taggctctca tgtgtgcctt gctgcaccat taatttatgg ctccactgga caggaaatga    3900
actcagtacc actgtccagg gaagggagcc ggagctgtct gtccatggct cagaggccag    3960
gtgaccttaa ggaagaaaca gtctgtaagt cacccttcct ttctctctac agtggagttc    4020
caggtgacat cagagaccca aaccctgaac cacctgctgg ggtcctctgt ctccctgcac    4080
tgcagtttct ccatggcacc aggcctggac ctcactggcg tggagtggcg gctgcagcat    4140
aaaggcagcg ccagctggt gtacagctgg aagacagggc aggggcaggc caagcgcaag    4200
ggcgctacac tggagcctga ggagctactc agggctggaa cgcctctct caccttaccc    4260 aacctcactc taaaggatga ggggaactac atctgccaga tctccacctc tctgtatcaa    4320
gctcaacaga tcatgccact taacatcctg gtaaggaca ggccttgggt tttctgggat    4380
aagggagagg gagatgccta tgggaatgtt tcccagacta gaatccaacc ccagagaaaa    4440
tttcctcaga gaaggaatgc attcccacaa cccaaacacc atcttcattc tggaggtgtg    4500
ggtgatcaga taaggcgtct cactgaatgc caagataata cccccaggaa ataactacat    4560
cagaataaaa accctgggct agctgtctgt aatttcagtc ccctggacca tttccttgag    4620
agggaccctg caggtgtcca ggcaaggaag tcaatcacag ggagaaagaa accttggttc    4680
agattaactt cttcaacctg gatccgactt gggaagtctg atacaaggcg atttatcccc    4740
aa                                                                   4742

<210> SEQ ID NO 21
<211> LENGTH: 5810
<212> TYPE: DNA
<213> ORGANISM: Homo sapiens

<400> SEQUENCE: 21
atggcacggc cacatccctg gtggctgtgc gttctgggga ccctggtggg gctctcagct      60
actccagccc ccaagagctg cccagagagg cactactggg ctcagggaaa gctgtgctgc     120
cagatgtgtg agccaggtaa gaggggggcct tggtaagggc caggtgagtg gcgaaagaga     180
gaggactggg gttaatacag taaataggcg caggtgagc ctgagctcaa gcaaggaggg      240
aaatcctgca gctgtgggga ggcaccacct tgaagagggc agagaaccag cccttctcag     300
gccttgatcc cttaccctct cctcccagga acattcctcg tgaaggactg tgaccagcat     360
agaaaggctc tcagtgtga tccttgcata ccggggggtct ccttctctcc tgaccaccac    420
acccggcccc actgtgagag ctgtcggcac tgtaactctg gtgaggtggg caagggtgtg     480
taggtgggga cgatggacaa gcatctgggg gagcaaggct ggtgacgggt ttggggggtgc     540 aaggaggatg acggggccaa agctttggcc ttcttcaagg ctcacagcaa gtggagccaa     600
tgctgggaaa tgcggcaccc taggtggggc atgaattaac gtgggcagac atctagtatt     660
ccaggaaagg gataaataga atttgaggga ttggtgagaa cggtctatg gataggatca      720 agacaataaa atgagagaag tggctctatg accccagatt tcgggcaagc aaccccccaac    780 caataaactg actgtgttcc cagagtgcac atgtgcaggt tggccattgg gaatttggaa     840
tacatctttc taaggaaata acaaagcaac ccaataggta acaacctttt tttgcacaaa     900
```

```
agccaatttg agaaaatgag tatgtatgta gcctgtgttt ttattttata gttccaaaaa    960
aaaaggtttt ttttaaacta agaagtataa tatctgcagt tgtgcttatg aatgctgtta   1020
ttatttctcc atcttcgcta caatttcaga aactacggcc agtatacact agaatagcag   1080
gctttaaagt ggcccctttg aacaaatgtt ctctagcaag acactttta gaaccaggta    1140
actgtaacta ttaaactacc tacttgcaaa acgtgtttgg tgtcactggg tctcttggta   1200
ctgggttttg ttttgtttag tttagagaca aggtctagct ctgtcaccca ggctggagtg   1260
cagtggtgca atcatagctc cccacagcct tgaactcctg ggctcaagca atcttctagt   1320
ctcagcctct gaaagtgcca ggattacagg tgtgagctgt agtgcctggt cccgtaaaaa   1380
caaaaacaaa aaccaacacc agatgtggtg gctcatgcct ataatcccag cacttgggag   1440
gccaaggcag aagggtattt gcatattttg tagagacttg agcccaggag cttgagacca   1500
gctgggcaac atagtgagac cttgtctcta aaaaaattgg ctggtcatgg tagtgcacct   1560
gcagtcccag ctacttggga ggctgagatg ggaagatcac ttgagcccaa gaggtcccca   1620
agaggtccag gctgctcaca tcactgcact ccagcctggg taacagagca aaacccttt    1680
tcacacacac acacacacac acacaaaaag ccagagcagt ggctcacact tgtaatccca   1740
gcactttagg aggccaaggc aggcggatcc cttgagccca ggagtttaag aacaccctgg   1800
gcaacatggc aaaaccctgt ctctactaaa aatacaaaaa gttagccagg cgtggtggca   1860
cgaacctgta gtcccagcta ctcagaaggc tgaagtgaga agatcacttg agtccaggaa   1920
gtggaggctg cagtgagccg tgactgtacc actgcactcc agcttgggag acagagtgag   1980
cagagtgaga ccctgtttcc aaaaaaaaaa agaaaacaaa agcttttcca ttgcaaatca   2040
accaaaaagg aacgtctttta atacacaaga aatattcttc agtctactta acttaaaaat   2100
gtaactgtaa tagatgcttt tctcttgaca gcggccccgg cagggttgga acttttccta   2160
gtcaaaaccc ccctactcac tctgcagacc cttcctgaag gtcttcgccc catactgagc   2220
ccatcttcag tcccttcact tgttccaaac tagcccaatc catgacccctt ctctgggagc   2280
tcagccaata gatcccaaag taccacagca gcacctggct gcagaaggac ccccgggaaa   2340
tgcagtcagg ggtgagaaga tgggtgggct gaatgagctc ggccctctct gggccttagt   2400
gctggcatct atgagatgag gacatgcctg aagtcagcct ggaattttga gcccaggtta   2460
tacctggtaa atagaactcc caggtctccg gatactcacc actaaaacaa tagcacctca   2520
ttgttttttgt tttgttttgt tttgtttttt aattatactt taagttctag ggtacatgta   2580
cacaatgtgc aggtttgtta cataggtata catgtgccat gttggtgtgc tgcacccatt   2640
aactcatcat ttacattagg tatatctcct aatgctatcc ctcctccctc cccacacccc   2700
acgacaggcc ccagtgtgtg atgttcccct tcctgtgtcc aagtgttctc attgttcaat   2760
tcccacctac gagtgagaac acattgtttt taaccctccc cagcagcttc tttaacccct   2820
ccatttccct tttggcggag acccttgtca tcactcctct ctaccaccag tgctctcccc   2880
tcctgcactg tcccaggctt cctcattctt cccttgcagg tccttatcca acatggctca   2940
caattcctgg gaagccacaa ggaaaccaaa ttctagtagc aactcagagt cagcattcat   3000
tagcaggtca cagggccata aggatgccaa gaaggaattt gtccctctcc ttgtcctgac   3060
aaaaggcata agtagaagaa aattgttagg tttggttatg acctttgaca ttctctcttt   3120
gacatcctcc ctttctgcac ccctcttcca cctgtcaggg cacctagggc tccccgggtc   3180
cccacaagtg tctgccctaa ggcccaccag gctttcttgc agcctgtccc acatctgggt   3240
gtcactgcct tcctctgaat caccctcctc tcaaaccagc cgccagcgag cccagcccag   3300
```

```
cccagctagt gccctaccac acccgccccc aggataatta acacccagcc acccagcatc   3360
ggacctctac acttgagcaa aatgtatatt ttaaaggcaa attctcacgc ctgtaatccc   3420
agcactttgg gaggccaagg cgggcggatc acgaggtcag gagattgaga ccatcctggc   3480
taacacggtg aaaccccgtc tctactaaaa atacaaaaaa ttagccaggt gtggtggcac   3540
acacctgtaa tcccagctac tagggaggct gaggcaggag aatcacttga actcaggagg   3600
cggaggttgc actgagccga gatcgtgcca ctgcactcca acctgggcga caaagcaaga   3660
ctctgtcaaa aacaaacaa acaaaataaa ggctaagtaa ctgtaatcaa gtaactattt    3720
attatttatt tattttagtg tatccacagg ttgtgcagcc atcaacacta tctaattcta   3780
taacattttc gttaccccag agaaacttgt accccttagc aatgactccc catttcttcc   3840
ccccaaccaa ccccagcccc agcccagccc ctgggaatc cctaatatac tttgttttgt    3900
ttttgttgg tggtgtttga cacaggatct cactctgtca cccaggctgg agcgcagtat    3960
catgatctca gctcactgta acctccacct cccgggctca gcgatcctc ccacctcagc    4020
ctccccagta gcttgggcct acaggtgtgc accaccacac ccagctaatt tttgtatttt   4080
ttgtagagac ggggttttcac catgttggcc aggctggtct caaactcctg agctcaagca   4140
atccacccac ctcaacctcc caaagtgctg ggattacagg cgtaagccac tgcacctggc   4200
tatttttcttt ctttctttc ttttttttttt ttttttgaga cggagtttca ctctgttgcc   4260
caggctggag tgcagtggcg tgatctcggc tcactgcaac ttccacctcc cgggttcaag   4320
caattccctg cctcacccgg ctatttata tttgttgatc tgctgctggt tatgcctgtg    4380
agccaaattt gtacaaattc ttaagcttta caatcatgcg tgcctctctg tacgtatatt   4440
atactttaat taaagttat taagtattg gggccgagca cagtggctca cgcctgtaat    4500
cccaacactt tgggaggctg aggctggtgc atcacctgag gtcaggagtt taataccagc   4560
ctggccaata cagtaaaacc ccgtctctac taaaaataca aaaaattagc cgggtgtggt   4620
ggcacacacc tgtaatccca gctacttggg aggctgaggc aggagaattg cttgaacccg   4680
ggaggcagag gttgcaacga gccaaggtca cgccattgca ctccagcctc ggcaacaaga   4740
gcgagactcc atctcaaaaa aataaataaa aaataaaaaa tgtatcaggg agtacaagag   4800
aaagtcatat aagctctttc tacttttcat ggtttctatg tctgaaccca tgaatcttcc   4860
ttctgaaagg tccaactttc ttcttaata acaataataa tggcaaaggc attggggac    4920
cgtgagcaaa gggcaggcct ttgcagggt gggaatggaa agggaagcac gtccctagag    4980
gtgggcctgg gatgggggtt gggggatgaa gcaagtggac cttgaaggtc tccacaggtc   5040
tgagtgtcct atgctccctg ggcctctctt cccccaggtc ttctcgttcg caactgcacc   5100
atcactgcca atgctgagtg tgcctgtcgc aatggctggc agtgcaggga caaggagtgc   5160
accgagtgtg atcctcttcc aaacccttcg ctgaccgctc ggtcgtctca ggccctgagc   5220
ccacaccctc agcccaccca cttacctat gtcagtggta agttccaggc aactctctgt    5280
gccatcacgt ggggtagcgg tgataccccca accagtactc cccactccta ccctagata    5340
aggtcagcct gtttctgcct tcccatccca tccagcacct ctcaggcctt cagatgtgcc   5400
ctatgggtc cctgctgct actcattctg tctctgtttt tccagagatg ctggaggcca    5460
ggacagctgg gcacatgcag actctggctg acttcaggca gctgcctgcc cggactctct   5520
ctacccactg gccacgtgag ttttctcctt aatcccacc gctagagaga atgcatacac    5580
gaggggccag gagggaagcc agacagaaag ctcctaggat tagggataag aggagggaa    5640
```

```
aaagcagagt ccactgttta ggagaggagt tggccaacgg tggcgggtgg gatagaataa    5700
ggtgggggaa aggggagagg caaggtgaca ggagggctgg gctgagggag ccaagggcta    5760
gaccctcccc taacccctgt gtgtcccctc ctattacagc ccaaagatcc                5810

<210> SEQ ID NO 22
<211> LENGTH: 780
<212> TYPE: DNA
<213> ORGANISM: Artificial
<220> FEATURE:
<223> OTHER INFORMATION: Homo sapiens and Mus musculus

<400> SEQUENCE: 22
atggcacggc cacatccctg gtggctgtgc gttctgggga ccctggtggg gctctcagct      60
actccagccc ccaagagctg cccagagagg cactactggg ctcagggaaa gctgtgctgc     120
cagatgtgtg agccaggaac attcctcgtg aaggactgtg accagcatag aaaggctgct     180
cagtgtgatc cttgcatacc gggggtctcc ttctctcctg accaccacac ccggccccac     240
tgtgagagct gtcggcactg taactctggt ctttctcgttc gcaactgcac catcactgcc     300
aatgctgagt gtgcctgtcg caatggctgg cagtgcaggg acaaggagtg caccgagtgt     360
gatcctcttc caaacccttc gctgaccgct cggtcgtctc aggccctgag cccacaccct     420
cagcccaccc acttacctta tgtcagtgag atgctggagg ccaggacagc tgggcacatg     480
cagactctgg ctgacttcag gcagctgcct gcccggactc tctctaccca ctggccaccc     540
caaagatccc tgtgcagctc ggactgcatc cggatctttg tgaccttctc agcatgtttt     600
cttatcttcg tcctgggtgc aatcttgttc ttccatcaaa gaagaaacca cgggccaaat     660
gaagaccggc aggcagtgcc tgaagagcct tgtccttaca gctgccccag ggaagaggag     720
ggcagtgcta tccctatcca ggaggactac cggaaacccg agcctgcttt ctacccttga     780

<210> SEQ ID NO 23
<211> LENGTH: 1603
<212> TYPE: DNA
<213> ORGANISM: Artificial
<220> FEATURE:
<223> OTHER INFORMATION: Homo sapiens and Mus musculus

<400> SEQUENCE: 23
cagccacaac tgccttcaaa ggtcggttta ccacccaagt ggagtcgcag tggctgctgc      60
ccagagcaca taggagccac cagtgactcg gtacaagcag ttggggctca gaaaagatct     120
ccctgggcag gagctatggc acggccacat ccctggtggc tgtgcgttct ggggaccctg     180
gtggggctct cagctactcc agcccccaag agctgcccag agaggcacta ctgggctcag     240
ggaaagctgt gctgccagat gtgtgagcca ggaacattcc tcgtgaagga ctgtgaccag     300
catagaaagg ctgctcagtg tgatccttgc ataccggggg tctccttctc tcctgaccac     360
cacacccggc ccactgtga gagctgtcgg cactgtaact ctggtcttct cgttcgcaac     420
tgcaccatca ctgccaatgc tgagtgtgcc tgtcgcaatg ctggcagtg cagggacaag     480 gagtgcaccg agtgtgatcc tcttccaaac ccttcgctga ccgctcggtc gtctcaggcc     540
ctgagcccac accctcagcc cacccactta ccttatgtca gtgagatgct ggaggccagg     600
acagctgggc acatgcagac tctggctgac ttcaggcagc tgcctgcccg gactctctct     660
acccactggc cacccaaag atccctgtgc agctcggact gcatccggat ctttgtgacc     720
ttctccagca tgtttcttat cttcgtcctg ggtgcaatct tgttcttcca tcaaagaaga     780
aaccacgggc caaatgaaga ccggcaggca gtgcctgaag agccttgtcc ttacagctgc     840
```

```
cccagggaag aggagggcag tgctatccct atccaggagg actaccggaa acccgagcct    900
gctttctacc cttgaccggg tgctggtggg gccctttctg acgagggggcc atccacagag   960
acctcaatgg tggcctgctc ccctgtcatg gtcatcagaa ccctttcctg tgaatactca  1020
acaaactgcc cttctgagac caacagggac aagagcagga tcccagtgtg tggcccagca  1080
agctggggag actcaggctc tagctataaa gcacacttac tctaagtgaa accgtccagc  1140
tgacaaaact acatgccagg ggtggaaatg gctcaccaag ggctccagag ggggcttggc  1200
agtgaggagc acgaagtgtt cctccagagg accagagttt gattcccagc actgtcaaat  1260
ggatcgaaac cagctgtaac tctactttca gagggtctga cacctttgac ctcctctggc  1320
atctacaaac acaggacgga cacacacaca cacacacaca cacacacaca cacacacacg  1380
attaaaaata taattttttt ttaaaaaaat ggaatgagcc accggcaggt gccctggtac  1440
cagaaggact gactgccgtg agagacacta tctacagaca cacagacttc ctggccttgg  1500
ttctgtcttc tctgtaagtt gtgacagtgc tgtgggaaag ctgaggctga gactttctct  1560
cagttgagct aaaactataa ataaattcat ttgtctactt cta                     1603
```

<210> SEQ ID NO 24
<211> LENGTH: 259
<212> TYPE: PRT
<213> ORGANISM: Artificial
<220> FEATURE:
<223> OTHER INFORMATION: Homo sapiens and Mus musculus

<400> SEQUENCE: 24

```
Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Cys Ile Arg Ile
            180                 185                 190

Phe Val Thr Phe Ser Ser Met Phe Leu Ile Phe Val Leu Gly Ala Ile
        195                 200                 205

Leu Phe Phe His Gln Arg Arg Asn His Gly Pro Asn Glu Asp Arg Gln
    210                 215                 220
```

```
Ala Val Pro Glu Glu Pro Cys Pro Tyr Ser Cys Pro Arg Glu Glu Glu
225                 230                 235                 240

Gly Ser Ala Ile Pro Ile Gln Glu Asp Tyr Arg Lys Pro Glu Pro Ala
            245                 250                 255

Phe Tyr Pro

<210> SEQ ID NO 25
<211> LENGTH: 9029
<212> TYPE: DNA
<213> ORGANISM: Artificial
<220> FEATURE:
<223> OTHER INFORMATION: Homo sapiens and Mus musculus

<400> SEQUENCE: 25
atggcacggc cacatccctg gtggctgtgc gttctgggga ccctggtggg gctctcagct      60
actccagccc ccaagagctg cccagagagg cactactggg ctcagggaaa gctgtgctgc     120
cagatgtgtg agccaggtaa gagggggcct tggtaagggc caggtgagtg gcgaaagaga     180
gaggactggg gttaatacag taaataggcg cagggtgaga ctgagctcaa gcaaggaggg     240
aaatcctgca gctgtgggga ggcaccacct tgaagagggc agagaaccag cccttctcag     300
gccttgatcc cttaccctct cctcccagga acattcctcg tgaaggactg tgaccagcat     360
agaaaggctg ctcagtgtga tccttgcata ccggggtctc ccttctctcc tgaccaccac     420
acccggcccc actgtgagag ctgtcggcac tgtaactctg gtgaggtggg caagggtgtg     480
taggtgggga cgatggacaa gcatctgggg gagcaaggct ggtgacgggt ttggggtgc      540
aaggaggatg acggggccaa agctttggcc ttcttcaagg ctcacagcaa gtggagccaa     600
tgctgggaaa tgcggcaccc taggtggggc atgaattaac gtgggcagac atctagtatt     660
ccaggaaagg gataaataga atttgaggga ttggtgagaa cgggtctatg gataggatca     720
agacaataaa atgagagaag tggctctatg accccagatt tcgggcaagc aaccccccaac    780
caataaactg actgtgttcc cagagtgcac atgtgcaggt tggccattgg gaatttggaa     840
tacatctttc taaggaaata caaagcaacc caataggta caaccttttt tttgcacaaa      900
agccaatttg agaaaatgag tatgtatgta gcctgtgttt ttattttata gttccaaaaa     960
aaaaggtttt ttttaaacta agaagtataa tatctgcagt tgtgcttatg aatgctgtta    1020
ttatttctcc atcttcgcta caatttcaga aactacggcc agtatacact agaatagcag    1080
gctttaaagt ggccccttg aacaaatgtt ctctagcaag acactttta gaaccaggta      1140
actgtaacta ttaaactacc tacttgcaaa acgtgtttgg tgtcactggg tctcttggta    1200
ctgggttttg ttttgtttag tttagagaca aggtctagct ctgtcaccca ggctggagtg    1260
cagtggtgca atcatagctc cccacagcct tgaactcctg ggctcaagca atcttctagt    1320
ctcagcctct gaaagtgcca ggattacagg tgtgagctgt agtgcctggt cccgtaaaaa    1380
caaaaacaaa aaccaacacc agatgtggtg gctcatgcct ataatcccag cacttgggag    1440
gccaaggcag aagggtattt gcatattttg tagagacttg agcccaggag cttgagacca    1500
gctgggcaac atagtgagac cttgtctcta aaaaaattgg ctggtcatgg tagtgcacct    1560
gcagtcccag ctactgggga ggctgagatg ggaagatcac ttgagcccaa gaggtcccca    1620
agaggtccag gctgctcaca tcactgcact ccagcctggg taacagagca aaccctttt     1680
tcacacacac acacacacac acacaaaaag ccagagcagt ggctcacact tgtaatccca    1740
gcactttagg aggccaaggc aggcggatcc cttgagccca ggagtttaag aacaccctgg    1800
gcaacatggc aaaaccctgt ctctactaaa aatacaaaaa gttagccagg cgtggtggca    1860
```

```
cgaacctgta gtcccagcta ctcagaaggc tgaagtgaga agatcacttg agtccaggaa   1920
gtggaggctg cagtgagccg tgactgtacc actgcactcc agcttgggag acagagtgag   1980
cagagtgaga ccctgtttcc aaaaaaaaaa agaaaacaaa agcttttcca ttgcaaatca   2040
accaaaaagg aacgtcttta atacacaaga aatattcttc agtctactta acttaaaaat   2100
gtaactgtaa tagatgcttt tctcttgaca gcggccccgg cagggttgga acttttccta   2160
gtcaaaaccc ccctactcac tctgcagacc cttcctgaag gtcttcgccc catactgagc   2220
ccatcttcag tcccttcact tgttccaaac tagcccaatc catgacccct ctctgggagc   2280
tcagccaata gatcccaaag taccacagca gcacctggct gcagaaggac ccccgggaaa   2340
tgcagtcagg ggtgagaaga tgggtgggct gaatgagctc ggccctctct gggccttagt   2400
gctggcatct atgagatgag gacatgcctg aagtcagcct ggaattttga gcccaggtta   2460
tacctggtaa atagaactcc caggtctccg gatactcacc actaaaacaa tagcacctca   2520 ttgttttttgt tttgttttgt tttgttttttt aattatactt taagttctag ggtacatgta   2580
cacaatgtgc aggtttgtta cataggtata catgtgccat gttggtgtgc tgcacccatt   2640
aactcatcat ttacattagg tatatctcct aatgctatcc ctcctccctc cccacacccc   2700
acgacaggcc ccagtgtgtg atgttcccct tcctgtgtcc aagtgttctc attgttcaat   2760
tcccacctac gagtgagaac acattgtttt taaccctccc cagcagcttc tttaacccct   2820
ccatttccct tttggcggag accttgtca tcactcctct ctaccaccag tgctctcccc   2880
tcctgcactg tcccaggctt cctcattctt cccttgcagg tccttatcca acatggctca   2940
caattcctgg gaagccacaa ggaaaccaaa ttctagtagc aactcagagt cagcattcat   3000
tagcaggtca cagggccata aggatgccaa gaaggaattt gtccctctcc ttgtcctgac   3060
aaaaggcata agtagaagaa aattgttagg tttggttatg acctttgaca ttctctcttt   3120
gacatcctcc ctttctgcac ccctcttcca cctgtcaggg cacctagggc tccccgggtc   3180
cccacaagtg tctgccctaa ggcccaccag gctttcttgc agcctgtccc acatctgggt   3240
gtcactgcct tcctctgaat caccctcctc tcaaaccagc cgccagcgag cccagcccag   3300
cccagctagt gccctaccac acccgccccc aggataatta acacccagcc acccagcatc   3360
ggacctctac acttgagcaa aatgtatatt ttaaaggcaa attctcacgc ctgtaatccc   3420
agcactttgg gaggccaagg cgggcggatc acgaggtcag gagattgaga ccatcctggc   3480
taacacggtg aaaccccgtc tctactaaaa atacaaaaaa ttagccaggt gtggtggcac   3540
acacctgtaa tcccagctac tagggaggct gaggcaggaa aatcacttga actcaggagg   3600
cggaggttgc actgagccga gatcgtgcca ctgcactcca acctgggcga caaagcaaga   3660
ctctgtcaaa aacaaacaa acaaaataaa ggctaagtaa ctgtaatcaa gtaactattt   3720
attatttatt tattttagtg tatccacagg ttgtgcagcc atcaacacta tctaattcta   3780
taacattttc gttaccccag agaaacttgt accccttagc aatgactccc catttcttcc   3840
ccccaaccaa ccccagcccc agccccagcc cctgggaatc cctaatatac tttgtttttgt   3900 tttttgttgg tggtgtttga gacaggatct cactctgtca cccaggctgg agcgcagtat   3960
catgatctca gctcactgta acctccacct cccgggctca agcgatcctc ccacctcagc   4020
ctccccagta gcttgggcct acaggtgtgc accaccacac ccagctaatt tttgtatttt   4080
ttgtagagac ggggtttcac catgttggcc aggctggtct caaactcctg agctcaagca   4140
atccacccac ctcaacctcc caaagtgctg ggattacagg cgtaagccac tgcacctggc   4200
```

```
tattttctttt ctttctttc tttttttttt tttttgaga cggagtttca ctctgttgcc    4260
caggctggag tgcagtggcg tgatctcggc tcactgcaac ttccacctcc cgggttcaag    4320
caattccctg cctcacccgg ctattttata tttgttgatc tgctgctggt tatgcctgtg    4380
agccaaattt gtacaaattc ttaagcttta caatcatgcg tgcctctctg tacgtatatt    4440
atactttaat taaaagttat taaagtattg gggccgagca cagtggctca cgcctgtaat    4500
cccaacactt tgggaggctg aggctggtgc atcacctgag gtcaggagtt taataccagc    4560
ctggccaata cagtaaaacc ccgtctctac taaaaataca aaaaattagc cgggtgtggt    4620
ggcacacacc tgtaatccca gctacttggg aggctgaggc aggagaattg cttgaacccg    4680
ggaggcagag gttgcaacga gccaaggtca cgccattgca ctccagcctc ggcaacaaga    4740
gcgagactcc atctcaaaaa aataaataaa aataaaaaa tgtatcaggg agtacaagag    4800
aaagtcatat aagctctttc tacttttcat ggtttctatg tctgaaccca tgaatcttcc    4860
ttctgaaagg tccaactttc ttctttaata acaataataa tggcaaaggc attggggac    4920
cgtgagcaaa gggcaggcct ttgcaggggt gggaatggaa agggaagcac gtccctagag    4980
gtgggcctgg gatgggggtt gggggatgaa gcaagtggac cttgaaggtc tccacaggtc    5040
tgagtgtcct atgctccctg ggcctctctt cccccaggtc ttctcgttcg caactgcacc    5100
atcactgcca atgctgagtg tgcctgtcgc aatggctggc agtgcaggga caaggagtgc    5160
accgagtgtg atcctcttcc aaacccttcg ctgaccgctc ggtcgtctca ggccctgagc    5220
ccacaccctc agcccaccca cttaccttat gtcagtggta agttccaggc aactctctgt    5280
gccatcacgt ggggtagcgg tgataccccca accagtactc ccactcccta cccctagata    5340
aggtcagcct gtttctgcct tcccatccca tccagcacct ctcaggcctt cagatgtgcc    5400
ctatgggtc ccctgctgct actcattctg tctctgtttt tccagagatg ctggaggcca    5460
ggacagctgg gcacatgcag actctggctg acttcaggca gctgctgcc cggactctct    5520
ctacccactg gccacgtgag ttttctcctt aatccccacc gctagagaga atgcatacac    5580
gaggggccag gagggaagcc agacagaaag ctcctaggat tagggataag aggaggggaa    5640
aaagcagagt ccactgttta ggagaggagt tggccaacgg tggcgggtgg gatagaataa    5700
ggtgggggaa agggagagg caaggtgaca ggagggctgg gctgagggag ccaagggcta    5760
gaccctcccc taaccctgt gtgtcccctc ctattacagc ccaaagatcc ctgtgcagct    5820
cggactgcat ccggatcttt gtgaccttct ccagcatgtt tcttatcttc gtcctgggtg    5880
caatcttgtt cttccatcaa agaagaaacc acgggccaag taagacacag gccttccctc    5940
ctgtctctca gctgtgctac ccacacctaa agcccccaca cctactccac ccacctactc    6000
tggctcctca agtgtccttc ccccagactc ccaagccccc cagctctca gccctccact    6060
tgggcttttc tcctcttttc tccccttcac ctttcttctc tccactgctg accgattgtg    6120
tttgcacaga tgaagaccgg caggcagtgc ctgaagagcc ttgtccttac agctgcccca    6180
gggaagagga gggcagtgct atccctatcc aggaggacta ccggaaaccc gagcctgctt    6240
tctacccttg accgggtgct ggtgggccc tttctgacga ggggccatcc acagagacct    6300
caatggtggc ctgctcccct gtcatggtca tcagaaccct ttcctgtgaa tactcaacaa    6360
actgcccttc tgagaccaac agggacaaga gcaggatccc agtgtgtggc ccagcaagct    6420
ggggagactc aggctctagc tataaagcac acttactcta agtgaaaccg tccagctgac    6480
aaaactacat gccaggggtg gaaatggctc accaagggct ccagagggg cttgcagtg    6540
aggagcacga agtgttcctc cagaggacca gagtttgatt cccagcactg tcaaatggat    6600
```

```
cgaaaccagc tgtaactcta ctttcagagg gtctgacacc tttgacctcc tctggcatct    6660
acaaacacag gacggacaca cacacacaca cacacacaca cacacgatta                6720
aaaataataa ttttttttaa aaaaatggaa tgagccaccg gcaggtgccc tggtaccaga    6780
aggactgact gccgtgagag acactatcta cagacacaca gacttcctgg ccttggttct    6840
gtcttctctg taagttgtga cagtgctgtg ggaaagctga ggctgagact ttctctcagt    6900
tgagctaaaa ctataaataa attcatttgt ctacttctat acacattgtc ccttctctct    6960
gtgcaggcaa acactggaac ccggagccaa gccttacggc ccagggactc tagtaacaag    7020
ccagctatgg acactctcca tgtgctattc cccttcctac agaatgaggg taggggaaca    7080
agaggaggag gaggaagaag aaaaaaaaga agggacagtg aactaggaag aaggatagtg    7140
taaatgcatt aatgaattcc gaagttccta ttctctagaa agtataggaa cttcaggtct    7200
gaagaggagt ttacgtccag ccaagctagc ttggctgcag gtcgtcgaaa ttctaccggg    7260
taggggaggc gcttttccca aggcagtctg gagcatgcgc tttagcagcc ccgctgggca    7320
cttggcgcta cacaagtggc ctctggcctc gcacacattc cacatccacc ggtaggcgcc    7380
aaccggctcc gttctttggt ggccccttcg cgccaccttc tactcctccc ctagtcagga    7440
agttcccccc cgccccgcag ctcgcgtcgt gcaggacgtg acaaatggaa gtagcacgtc    7500
tcactagtct cgtgcagatg gacagcaccg ctgagcaatg gaagcgggta ggcctttggg    7560
gcagcggcca atagcagctt tgctccttcg cttttctgggc tcagaggctg ggaaggggtg    7620
ggtccggggg cgggctcagg ggcgggctca ggggcggggc gggcgcccga aggtcctccg    7680
gaggcccggc attctgcacg cttcaaaagc gcacgtctgc cgcgctgttc tcctcttcct    7740
catctccggg cctttcgacc tgcagcctgt tgacaattaa tcatcggcat agtatatcgg    7800
catagtataa tacgacaagg tgaggaacta aaccatggga tcggccattg aacaagatgg    7860
attgcacgca ggttctccgg ccgcttgggt ggagaggcta ttcggctatg actgggcaca    7920
acagacaatc ggctgctctg atgccgccgt gttccggctg tcagcgcagg ggcgcccggt    7980 tcttttttgtc aagaccgacc tgtccggtgc cctgaatgaa ctgcaggacg aggcagcgcg    8040
gctatcgtgg ctggccacga cgggcgttcc ttgcgcagct gtgctcgacg ttgtcactga    8100
agcgggaagg gactggctgc tattgggcga agtgccgggg caggatctcc tgtcatctca    8160
ccttgctcct gccgagaaag tatccatcat ggctgatgca atgcggcggc tgcatacgct    8220
tgatccggct acctgcccat tcgaccacca agcgaaacat cgcatcgagc gagcacgtac    8280
tcggatggaa gccggtcttg tcgatcagga tgatctggac gaagagcatc aggggctcgc    8340
gccagccgaa ctgttcgcca ggctcaaggc gcgcatgccc gacggcgatg atctcgtcgt    8400
gacccatggc gatgcctgct tgccgaatat catggtggaa aatggccgct tttctggatt    8460
catcgactgt ggccggctgg gtgtggcgga ccgctatcag gacatagcgt tggctacccg    8520
tgatattgct gaagagcttg gcggcgaatg ggctgaccgc ttcctcgtgc tttacggtat    8580
cgccgctccc gattcgcagc gcatcgcctt ctatcgcctt cttgacgagt tcttctgagg    8640
ggatcaattc tctagagctc gctgatcagc ctcgactgtg ccttctagtt gccagccatc    8700
tgttgtttgc ccctccccg tgccttcctt gaccctggaa ggtgccactc ccactgtcct    8760
ttcctaataa aatgaggaaa ttgcatcgca ttgtctgagt aggtgtcatt ctattctggg    8820
gggtggggtg gggcaggaca gcaagggggga ggattgggaa gacaatagca ggcatgctgg    8880
ggatgcggtg ggctctatgg cttctgaggc ggaaagaacc agctggggct cgactagagc    8940
```

```
ttgcggaacc cttcgaagtt cctattctct agaaagtata ggaacttcat cagtcaggta    9000
cataattagg tggatccaat attcaattg                                      9029

<210> SEQ ID NO 26
<211> LENGTH: 1862
<212> TYPE: DNA
<213> ORGANISM: Artificial
<220> FEATURE:
<223> OTHER INFORMATION: Synthesized sequence

<400> SEQUENCE: 26
gaattccgaa gttcctattc tctagaaagt ataggaactt caggtctgaa gaggagttta      60
cgtccagcca agctagcttg gctgcaggtc gtcgaaattc taccgggtag gggaggcgct     120
tttcccaagg cagtctggag catgcgcttt agcagcccg ctgggcactt ggcgctacac      180
aagtggcctc tggcctcgca cacattccac atccaccggt aggcgccaac cggctccgtt     240
ctttggtggc cccttcgcgc cacctttctac tcctcccta gtcaggaagt tccccccgc     300 cccgcagctc gcgtcgtgca ggacgtgaca aatggaagta gcacgtctca ctagtctcgt     360
gcagatggac agcaccgctg agcaatggaa gcgggtaggc ctttggggca gcggccaata     420
gcagctttgc tccttcgctt tctgggctca gaggctggga aggggtgggt ccggggggcgg    480 gctcaggggc gggctcaggg gcggggcggg cgcccgaagg tcctccggag gcccggcatt     540
ctgcacgctt caaaagcgca cgtctgccgc gctgttctcc tcttcctcat ctccgggcct     600
ttcgacctgc agcctgttga caattaatca tcggcatagt atatcggcat agtataatac     660
gacaaggtga ggaactaaac catgggatcg gccattgaac aagatggatt gcacgcaggt     720
tctccggccg cttgggtgga gaggctattc ggctatgact gggcacaaca gacaatcggc     780
tgctctgatg ccgccgtgtt ccggctgtca gcgcaggggc gcccggttct ttttgtcaag     840
accgacctgt ccggtgccct gaatgaactg caggacgagg cagcgcggct atcgtggctg     900
gccacgacgg gcgttccttg cgcagctgtg ctcgacgttg tcactgaagc gggaagggac     960
tggctgctat tgggcgaagt gccggggcag gatctcctgt catctcacct tgctcctgcc    1020
gagaaagtat ccatcatggc tgatgcaatg cggcggctgc atacgcttga tccggctacc    1080
tgcccattcg accaccaagc gaaacatcgc atcgagcgag cacgtactcg gatggaagcc    1140
ggtcttgtcg atcaggatga tctggacgaa gagcatcagg ggctcgcgcc agccgaactg    1200
ttcgccaggc tcaaggcgcg catgcccgac ggcgatgatc tcgtcgtgac ccatggcgat    1260
gcctgcttgc cgaatatcat ggtggaaaat ggccgctttt ctggattcat cgactgtggc    1320
cggctgggtg tggcggaccg ctatcaggac atagcgttgg ctacccgtga tattgctgaa    1380
gagcttggcg gcgaatgggc tgaccgcttc ctcgtgcttt acggtatcgc cgctcccgat    1440
tcgcagcgca tcgccttcta tcgccttctt gacgagttct tctgagggga tcaattctct    1500
agagctcgct gatcagcctc gactgtgcct tctagttgcc agccatctgt tgtttgcccc    1560
tcccccgtgc cttccttgac cctggaaggt gccactccca ctgtcctttc ctaataaaat    1620
gaggaaattg catcgcattg tctgagtagg tgtcattcta ttctgggggg tggggtgggg    1680
caggacagca agggggagga ttgggaagac aatagcaggc atgctgggga tgcggtgggc    1740
tctatggctt ctgaggcgga aagaaccagc tggggctcga ctagagcttg cggaacccctt   1800 cgaagttcct attctctaga agtataggaa cttcatcag tcaggtacat aatggtggat    1860
cc                                                                    1862
```

-continued

```
<210> SEQ ID NO 27
<211> LENGTH: 24
<212> TYPE: DNA
<213> ORGANISM: Artificial
<220> FEATURE:
<223> OTHER INFORMATION: PCR primer

<400> SEQUENCE: 27
aagcttccag gtcagggagg aatc                                         24

<210> SEQ ID NO 28
<211> LENGTH: 24
<212> TYPE: DNA
<213> ORGANISM: Artificial
<220> FEATURE:
<223> OTHER INFORMATION: PCR primer

<400> SEQUENCE: 28
gtgtcttact tggcccgtgg tttc                                         24

<210> SEQ ID NO 29
<211> LENGTH: 24
<212> TYPE: DNA
<213> ORGANISM: Artificial
<220> FEATURE:
<223> OTHER INFORMATION: PCR primer

<400> SEQUENCE: 29
tggcgggtgg gatagaataa ggtg                                         24

<210> SEQ ID NO 30
<211> LENGTH: 25
<212> TYPE: DNA
<213> ORGANISM: Artificial
<220> FEATURE:
<223> OTHER INFORMATION: PCR primer

<400> SEQUENCE: 30
cttccacatg agcgtggtca gggcc                                        25

<210> SEQ ID NO 31
<211> LENGTH: 25
<212> TYPE: DNA
<213> ORGANISM: Artificial
<220> FEATURE:
<223> OTHER INFORMATION: PCR primer

<400> SEQUENCE: 31
ccttacggcc cagggactct agtaa                                        25

<210> SEQ ID NO 32
<211> LENGTH: 25
<212> TYPE: DNA
<213> ORGANISM: Artificial
<220> FEATURE:
<223> OTHER INFORMATION: PCR primer

<400> SEQUENCE: 32
cccttgtcac accacttaac ccctt                                        25

<210> SEQ ID NO 33
<211> LENGTH: 25
<212> TYPE: DNA
<213> ORGANISM: Artificial
<220> FEATURE:
<223> OTHER INFORMATION: PCR primer
```

<400> SEQUENCE: 33
gacaagcgtt agtaggcaca tatac                                       25

<210> SEQ ID NO 34
<211> LENGTH: 24
<212> TYPE: DNA
<213> ORGANISM: Artificial
<220> FEATURE:
<223> OTHER INFORMATION: PCR primer

<400> SEQUENCE: 34
gctccaattt cccacaacat tagt                                        24

<210> SEQ ID NO 35
<211> LENGTH: 22
<212> TYPE: DNA
<213> ORGANISM: Artificial
<220> FEATURE:
<223> OTHER INFORMATION: PCR primer

<400> SEQUENCE: 35
ctgcaggcat tgtaactctg gt                                          22

<210> SEQ ID NO 36
<211> LENGTH: 21
<212> TYPE: DNA
<213> ORGANISM: Artificial
<220> FEATURE:
<223> OTHER INFORMATION: PCR primer

<400> SEQUENCE: 36
catgaggtaa gtgggtgggt g                                           21

<210> SEQ ID NO 37
<211> LENGTH: 22
<212> TYPE: DNA
<213> ORGANISM: Artificial
<220> FEATURE:
<223> OTHER INFORMATION: PCR primer

<400> SEQUENCE: 37
ctactgggct cagggaaagc tg                                          22

<210> SEQ ID NO 38
<211> LENGTH: 21
<212> TYPE: DNA
<213> ORGANISM: Artificial
<220> FEATURE:
<223> OTHER INFORMATION: PCR primer

<400> SEQUENCE: 38
attggcagtg atggtgcagt t                                           21

<210> SEQ ID NO 39
<211> LENGTH: 25
<212> TYPE: DNA
<213> ORGANISM: Artificial
<220> FEATURE:
<223> OTHER INFORMATION: PCR primer

<400> SEQUENCE: 39
ccaagggact attttagatg ggcag                                       25

<210> SEQ ID NO 40
<211> LENGTH: 26

```
<212> TYPE: DNA
<213> ORGANISM: Artificial
<220> FEATURE:
<223> OTHER INFORMATION: PCR primer

<400> SEQUENCE: 40
gaagctacaa gctcctaggt aggggg                                          26

<210> SEQ ID NO 41
<211> LENGTH: 23
<212> TYPE: DNA
<213> ORGANISM: Artificial
<220> FEATURE:
<223> OTHER INFORMATION: PCR primer

<400> SEQUENCE: 41
acgggttggc tcaaaccatt aca                                             23

<210> SEQ ID NO 42
<211> LENGTH: 20
<212> TYPE: DNA
<213> ORGANISM: Artificial
<220> FEATURE:
<223> OTHER INFORMATION: PCR primer

<400> SEQUENCE: 42
cctggctcac agtgtcagag                                                 20

<210> SEQ ID NO 43
<211> LENGTH: 20
<212> TYPE: DNA
<213> ORGANISM: Artificial
<220> FEATURE:
<223> OTHER INFORMATION: PCR primer

<400> SEQUENCE: 43
cagggctctc ctcgattttt                                                 20

<210> SEQ ID NO 44
<211> LENGTH: 20
<212> TYPE: DNA
<213> ORGANISM: Artificial
<220> FEATURE:
<223> OTHER INFORMATION: PCR primer

<400> SEQUENCE: 44
ccctgctcgt ggtgaccgaa                                                 20

<210> SEQ ID NO 45
<211> LENGTH: 20
<212> TYPE: DNA
<213> ORGANISM: Artificial
<220> FEATURE:
<223> OTHER INFORMATION: PCR primer

<400> SEQUENCE: 45
gcaggctctc tttgatctgc                                                 20

<210> SEQ ID NO 46
<211> LENGTH: 25
<212> TYPE: DNA
<213> ORGANISM: Artificial
<220> FEATURE:
<223> OTHER INFORMATION: PCR primer

<400> SEQUENCE: 46
```

```
ccagggaggt ggcccactga taata                                              25

<210> SEQ ID NO 47
<211> LENGTH: 25
<212> TYPE: DNA
<213> ORGANISM: Artificial
<220> FEATURE:
<223> OTHER INFORMATION: PCR primer

<400> SEQUENCE: 47
cacccctgca tcctgcaatt tcaca                                              25

<210> SEQ ID NO 48
<211> LENGTH: 25
<212> TYPE: DNA
<213> ORGANISM: Artificial
<220> FEATURE:
<223> OTHER INFORMATION: PCR primer

<400> SEQUENCE: 48
actaacgcaa gcaggtccag ctccc                                              25
```